(12) United States Patent
Parker et al.

(10) Patent No.: US 7,179,895 B2
(45) Date of Patent: Feb. 20, 2007

(54) RAT CALCIUM CHANNEL SUBUNITS AND RELATED PROBES, CELL LINES AND METHODS

(75) Inventors: David Parker, Maple Ridge (CA);
Xianghong Xu, Vancouver (CA);
Afsheen Khawaja, Surrey (CA);
Terrance P. Snutch, Vancouver (CA)

(73) Assignee: Neuromed Pharmaceuticals Ltd., Vancouver (CA)

( * ) Notice: Subject to any disclaimer, the term of this patent is extended or adjusted under 35 U.S.C. 154(b) by 102 days.

(21) Appl. No.: 10/924,081

(22) Filed: Aug. 23, 2004

(65) Prior Publication Data

US 2005/0095678 A1     May 5, 2005

Related U.S. Application Data

(60) Provisional application No. 60/497,096, filed on Aug. 22, 2003.

(51) Int. Cl.
*C07H 21/02* (2006.01)
*C07K 1/00* (2006.01)
*G01N 33/53* (2006.01)

(52) U.S. Cl. .................. 536/23.1; 530/350; 435/7.1

(58) Field of Classification Search ............. 536/23.1; 530/350; 514/12; 435/7.1, 6
See application file for complete search history.

(56) References Cited

U.S. PATENT DOCUMENTS

| 5,386,025 A | 1/1995 | Jay et al. | |
|---|---|---|---|
| 6,441,156 B1 * | 8/2002 | Lerman et al. | 530/350 |

FOREIGN PATENT DOCUMENTS

| WO | WO 95/04144 | 2/1995 |
|---|---|---|
| WO | WO 96/39512 | 12/1996 |
| WO | WO-01/19870 | 3/2001 |
| WO | WO-03/062401 | 7/2003 |

OTHER PUBLICATIONS

Angelotti et al., FEBS Lett. (1996) 397:331-337.
Bourinet et al., EMBO J. (1994) 13:5032-5039.
Bourinet et al., Proc. Nat'l Acad. Sci. USA (1996) 93:1486-1491.
Brodbeck et al., J. Biol. Chem. (2002) 277:7684-7693.
Brust et al., Neuropharmacology (1993) 32(11):1089-1102.
Burgess et al., Cell (1997) 88:385-392.
Chu, J. Mol. Cell. Cardiology (2003) 35:207-215.
Dascal et al., Science (1986) 231:1147-1150.
Dunlap et al., Trends Neurosci. (1995) 18:89-98.
Ellis et al., Science (1988) 241:1661-1664.
Felix et al., J. Neuroscience (1997) 17(18):6884-6891.
Fletcher et al., Cell (1996) 87:607-617
Gao et al., J. Biol. Chem. (2000) 275(16):12237-12242.
Hobom et al., Eur. J. Neurosci. (2000) 12(4):1217-1226.
Klugbauer et al., J. Neuroscience (1999) 19(2):684-691.
Marais et al., Molec. Pharmacol. (2001) 59(5):1243-1248.
McCleskey et al., Curr. Topics Membr. (1991) 39:295-326.
Ophoff et al., Cell (1996) 87:543-552.
Qin et al., Mol. Pharmacol. (2002) 62(3):485-496.
Stea et al., Neuron (1995) 15:929-940.
Stea et al., "Voltage-gated calcium channels," in Handbook of Receptors and Channels, edited by North, CRC Press (1995) pp. 113-151.
Zhuchenko et al., Nature Genetics (1997) 15:62-69.
International Search Report for PCT/CA2004/001550, mailed on Jan. 7, 2005, 5 pages.
Chin, On the Preparation and Utilization of Isolated and Purified Oligonucleotides, unpublished document submitted to the public collection of the Kathrine R. Everett Law Library of the University of North Carolina on Mar. 14, 2002.

\* cited by examiner

*Primary Examiner*—Ponnathapu Achutamurthy
*Assistant Examiner*—Robert B. Mondesi
(74) *Attorney, Agent, or Firm*—Morrison & Foerster LLP

(57) ABSTRACT

Novel sequences for calcium channel $\alpha_2\delta$-2 and $\alpha_2\delta$-3 subunits are provided. Also provided are cell lines that express the novel calcium channel subunits of the invention. These cells may be used for identifying compounds capable of stimulating or inhibiting the activation of the calcium channels.

10 Claims, 7 Drawing Sheets

```
                         1                                                  50
AF486277      (1)    MAVPARTCGASWPGPVRTARPWPGRGPRPCPDPRGPASGPARPLLLLLPP
SEQ ID No 3   (1)    MAVPARTCGASWPGPVRTARPWPGRGPRPCPDPRGPASGPARPLLLLLPP
Consensus     (1)    MAVPARTCGASWPGPVRTARPWPGRGPRPCPDPRGPASGPARPLLLLLPP
                         51                                                 100
AF486277     (51)    LLLLPLLTAPGASAYSFPQQHTMQHWARRLEQEIDGVMRIFGGVQQLREI
SEQ ID No 3  (51)    LLLLPLLTAPGASAYSFPQQHTMQHWARRLEQEIDGVMRIFGGVQQLREI
Consensus    (51)    LLLLPLLTAPGASAYSFPQQHTMQHWARRLEQEIDGVMRIFGGVQQLREI
                         101                                                150
AF486277    (101)    YKDNRNLFDVQENEPQKLVEKVAGDIESLLDRKVQALKRLADAAENFQKA
SEQ ID No 3 (101)    YKDNRNLFDVQENEPQKLVEKVAGDIESLLDRKVQALKRLADAAENFQKA
Consensus   (101)    YKDNRNLFDVQENEPQKLVEKVAGDIESLLDRKVQALKRLADAAENFQKA
                         151                                                200
AF486277    (151)    HRWQDNIKEEDIMYYDAKADAELDDPESEDMERGSKTSALRLDFIEEPNF
SEQ ID No 3 (151)    HRWQDNIKEEDIMYYDAKADAELDDPESEDMERGSKTSALRLDFIEEPNF
Consensus   (151)    HRWQDNIKEEDIMYYDAKADAELDDPESEDMERGSKTSALRLDFIEEPNF
                         201                                                250
AF486277    (201)    KNKVNYSYTAVQIPTDIYKGSTVILNELNWTEALENVFIENRRQDPTLLW
SEQ ID No 3 (201)    KNKVNYSYTAVQIPTDIYKGSTVILNELNWTEALENVFIENRRQDPTLLW
Consensus   (201)    KNKVNYSYTAVQIPTDIYKGSTVILNELNWTEALENVFIENRRQDPTLLW
                         251                                                300
AF486277    (251)    QVFGSATGVTRYYPATPWRAPKKIDLYDVRRRPWYIQGASSPKDMVIIVD
SEQ ID No 3 (251)    QVFGSATGVTRYYPATPWRAPKKIDLYDVRRRPWYIQGASSPKDMVIIVD
Consensus   (251)    QVFGSATGVTRYYPATPWRAPKKIDLYDVRRRPWYIQGASSPKDMVIIVD
                         301                                                350
AF486277    (301)    VSGSVSGLTLKLMKTSVCEMLDTLSDDDYVNVASFNEKAQPVSCFTHLVQ
SEQ ID No 3 (301)    VSGSVSGLTLKLMKTSVCEMLDTLSDDDYVNVASFNEKAQPVSCFTHLVQ
Consensus   (301)    VSGSVSGLTLKLMKTSVCEMLDTLSDDDYVNVASFNEKAQPVSCFTHLVQ
                         351                                                400
AF486277    (351)    ANVRNKKVFKEAVQGMVAKGTTGYKAGFEYAFDQLQNSNITRANCNKMIM
SEQ ID No 3 (351)    ANVRNKKVFKEAVQGMVAKGTTGYKAGFEYAFDQLQNSNITRANCNKMIM
Consensus   (351)    ANVRNKKVFKEAVQGMVAKGTTGYKAGFEYAFDQLQNSNITRANCNKMIM
                         401                                                450
AF486277    (401)    MFTDGGEDRVQDVFEKYNWPNRTVRVFTFSVGQHNYDVTPLQWMACTNKG
SEQ ID No 3 (401)    MFTDGGEDRVQDVFEKYNWPNRTVRVFTFSVGQHNYDVTPLQWMACTNKG
Consensus   (401)    MFTDGGEDRVQDVFEKYNWPNRTVRVFTFSVGQHNYDVTPLQWMACTNKG
                         451                                                500
AF486277    (451)    YYFEIPSIGAIRINTQEYLDVLGRPMVLAGKDAKQVQWTNVYEDALGLGL
SEQ ID No 3 (451)    YYFEIPSIGAIRINTQEYLDVLGRPMVLAGKDAKQVQWTNVYEDALGLGL
Consensus   (451)    YYFEIPSIGAIRINTQEYLDVLGRPMVLAGKDAKQVQWTNVYEDALGLGL
                         501                                                550
AF486277    (501)    VVTGTLPVFNLTQDGPGDKKNQLILGVMGIDVALNDIKRLTPNYTLGANG
SEQ ID No 3 (501)    VVTGTLPVFNLTQDGPGDKKNQLILGVMGIDVALNDIKRLTPNYTLGANG
Consensus   (501)    VVTGTLPVFNLTQDGPGDKKNQLILGVMGIDVALNDIKRLTPNYTLGANG
                         551                                                600
AF486277    (551)    YVFAIDLNGYVLLHPNLKPQITNFREPVTLDFLDAELEDENKEEIRRSMI
SEQ ID No 3 (551)    YVFAIDLNGYVLLHPNLKPQTTNFREPVTLDFLDAELEDENKEEIRRSMI
Consensus   (551)    YVFAIDLNGYVLLHPNLKPQ TNFREPVTLDFLDAELEDENKEEIRRSMI
                         601                                                650
AF486277    (601)    DGDKGHKQIRTLVKSLDERYIDEVIRNYTWVPIRSTNYSLGLVLPPYSTY
SEQ ID No 3 (601)    DEDKGHKQIRTLVKSLDERYIDEVIRNYTWVPIRSTNYSLGLVLPPYSTY
Consensus   (601)    D DKGHKQIRTLVKSLDERYIDEVIRNYTWVPIRSTNYSLGLVLPPYSTY
                         651                                                700
AF486277    (651)    YLQANLSDQILQVKLPISKLKDFEFLLPSSFESEGHVFIAPREYCKDLNA
SEQ ID No 3 (651)    YLQANLSDQILQVKY-------FEFLLPSSFESEGHVFIAPREYCKDLNA
Consensus   (651)    YLQANLSDQILQVK        FEFLLPSSFESEGHVFIAPREYCKDLNA
                         701                                                750
AF486277    (701)    SDNNTEFLKNFIELMEKVTPDSKQCNNFLLHNLILDTGITQQLVERVWRD
SEQ ID No 3 (694)    SDNNTEFLKNFIELMEKVTPDSKQCNNFLLHNLILDTGITQQLVERVWRD
Consensus   (701)    SDNNTEFLKNFIELMEKVTPDSKQCNNFLLHNLILDTGITQQLVERVWRD
```

Figure 1A

```
             751                                                    800
AF486277    (751) QDLNTYSLLAVFAATDGGITRVFPNKAAEDWTENPEPFNASFYRRSLDNR
SEQ ID No 3 (744) QDLNTYSLLAVFAATDGAVTRVFPNKAAEDWTENPEPFNASFYRRSLDNR
Consensus   (751) QDLNTYSLLAVFAATDGAITRVFPNKAAEDWTENPEPFNASFYRRSLDNR
             801                                                    850
AF486277    (801) GYIFKPPHQDSLLRPLELENDTVGVLVSTAVELSLGRRTLRPAVVGVKLD
SEQ ID No 3 (794) GYIFKPPHQDSLLRPLELENDTVGVLVSTAVELSLGRRTLRPAVVGVKLD
Consensus   (801) GYIFKPPHQDSLLRPLELENDTVGVLVSTAVELSLGRRTLRPAVVGVKLD
             851                                                    900
AF486277    (851) LEAWAEKFKVLASNRTHQDQPQKQCGPSSHCEMDCEVNNEDLLCVLIDDG
SEQ ID No 3 (844) LEAWAEKFKVLASNRTHQDQPQKQCGPSSHCEMDCEVNNEDLLCVLIDDG
Consensus   (851) LEAWAEKFKVLASNRTHQDQPQKQCGPSSHCEMDCEVNNEDLLCVLIDDG
             901                                                    950
AF486277    (901) GFLVLSNQNHQWDQVGRFFSEVDANLMLALYNNSFYTRKESYDYQAACAP
SEQ ID No 3 (894) GFLVLSNQNHQWDQVGRFFSEVDANLMLALYNNSFYTRKESYDYQAACAP
Consensus   (901) GFLVLSNQNHQWDQVGRFFSEVDANLMLALYNNSFYTRKESYDYQAACAP
             951                                                   1000
AF486277    (951) QPPGNLGAAPRGVFVPTIADFLNLAWWTSAAAWSLFQQLLYGLIYHSWFQ
SEQ ID No 3 (944) QPPGNLGAAPRGVFVPTIADFLNLAWWTSAAAWSLFQQLLYGLIYHSWFQ
Consensus   (951) QPPGNLGAAPRGVFVPTIADFLNLAWWTSAAAWSLFQQLLYGLIYHSWFQ
            1001                                                   1050
AF486277   (1001) ADPAEAEGSPETRESSCVMKQTQYYFGSVNASYNAIIDCGNCSRLFHAQR
SEQ ID No 3 (994) ADPAEAEGSPETRESSCVMKQTQYYFGSVNASYNAIIDCGNCSRLFHAQR
Consensus  (1001) ADPAEAEGSPETRESSCVMKQTQYYFGSVNASYNAIIDCGNCSRLFHAQR
            1051                                                   1100
AF486277   (1051) LTNTNLLFVVAEKPLCSQCEVGRLLQKETHCPADGPEQCELVQRPRYRTG
SEQ ID No 3 (1044) LTNTNLLFVVAEKPLCSQCEVGRLLQKETHCPADGPEQCELVQRPRYRRG
Consensus  (1051) LTNTNLLFVVAEKPLCSQCEVGRLLQKETHCPADGPEQCELVQRPRYR G
            1101                                                   1150
AF486277   (1101) PHICFDYNATEDTSDCGRGASFPPSLGVLVSLQLLLLLGLPPRPQPQIHS
SEQ ID No 3 (1094) PHICFDYNATEDTSDCGRGTSFPPSLGVLVSLQLLLLLGLPPRPQPQIHS
Consensus  (1101) PHICFDYNATEDTSDCGRG SFPPSLGVLVSLQLLLLLGLPPRPQPQIHS
            1151
AF486277   (1151) FTPSRRL-
SEQ ID No 3 (1144) FAASRRL-
Consensus  (1151) F  SRRL
```

Amino acid sequence identity 98.5 %

Figure 1B

|            |       | 1                                                            60 |
|------------|-------|-----------------------------------------------------------------|
| AF486278   | (1)   | MAGPGSLCCASRGASALLATALLYAALGDVVRSEQQIPLSVVKLWASAFGGEIKSIAAKY |
| SEQ ID NO 6 | (1)  | MAGPGSLCCASRGASALLATALLYAALGDVVRSEQQIPLSVVKLWASAFGGEIKSIAAKY |
| Consensus  | (1)   | MAGPGSLCCASRGASALLATALLYAALGDVVRSEQQIPLSVVKLWASAFGGEIKSIAAKY |
|            |       | 61                                                          120 |
| AF486278   | (61)  | SGSQLLQKKYKEYEKDVAIEEIDGLQLVKKLAKNMEEMFHKKSEAVRRLVEAAEEAHLKH |
| SEQ ID NO 6 | (61) | SGSQLLQKKYKEYEKDVAIEEIDGLQLVKKLAKNMEEMFHKKSEAVRRLVEAAEEAHLKH |
| Consensus  | (61)  | SGSQLLQKKYKEYEKDVAIEEIDGLQLVKKLAKNMEEMFHKKSEAVRRLVEAAEEAHLKH |
|            |       | 121                                                         180 |
| AF486278   | (121) | EFDADLQYEYFNAVLINERDKDGNFLELGKEFILAPNDHFNNLPVNISLSDVQVPTNMYN |
| SEQ ID NO 6 | (121)| EFDADLQYEYFNAVLINERDKDGNFLELGKEFILAPNDHFNNLPVNISLSDVQVPTNMYN |
| Consensus  | (121) | EFDADLQYEYFNAVLINERDKDGNFLELGKEFILAPNDHFNNLPVNISLSDVQVPTNMYN |
|            |       | 181                                                         240 |
| AF486278   | (181) | KDPAIVNGVYWSESLNKVFVDNFDRDPSLIWQYFGSAKGFFRQYPGIKWEPDENGVIAFD |
| SEQ ID NO 6 | (181)| KDPAIVNGVYWSESLNKVFVDNFDRDPSLIWQYFGSAKGFFRQYPGIKWEPDENGVIAFD |
| Consensus  | (181) | KDPAIVNGVYWSESLNKVFVDNFDRDPSLIWQYFGSAKGFFRQYPGIKWEPDENGVIAFD |
|            |       | 241                                                         300 |
| AF486278   | (241) | CRNRKWYIQAATSPKDVVILVDVSGSMKGLRLTIAKQTVSSILDTLGDDDFFNIITYNEE |
| SEQ ID NO 6 | (241)| CRNRKWYIQAATSPKDVVILVDVSGSMKGLRLTIAKQTVSSILDTLGDDDFFNIITYNEE |
| Consensus  | (241) | CRNRKWYIQAATSPKDVVILVDVSGSMKGLRLTIAKQTVSSILDTLGDDDFFNIITYNEE |
|            |       | 301                                                         360 |
| AF486278   | (301) | LHYVEPCLNGTLVQADRTNKEHFREHLDKLFAKGIGMLDIALNEAFNVLSDFNHTGQGSI |
| SEQ ID NO 6 | (301)| LHYVEPCLNGTLVQADRTNKEHFREHLDKLFAKGIGMLDIALNEAFNVLSDFNHTGQGSI |
| Consensus  | (301) | LHYVEPCLNGTLVQADRTNKEHFREHLDKLFAKGIGMLDIALNEAFNVLSDFNHTGQGSI |
|            |       | 361                                                         420 |
| AF486278   | (361) | CSQAIMLITDGAVDTYDTIFAKYNWPERKVRIFTYLIGREAAFADNLKWMACANKGFFTQ |
| SEQ ID NO 6 | (361)| CSQAIMLITDGAVDTYDTIFAKYNWPERKVRIFTYLIGREAAFADNLKWMACANKGFFTQ |
| Consensus  | (361) | CSQAIMLITDGAVDTYDTIFAKYNWPERKVRIFTYLIGREAAFADNLKWMACANKGFFTQ |
|            |       | 421                                                         480 |
| AF486278   | (421) | ISTLADVQENVMEYLHVLSRPKVIDQEHDVVWTEAYIDS-------LADDQGLVLMTTVA |
| SEQ ID NO 6 | (421)| ISTLADVQENVMEYLHVLSRPKVIDQEHDVVWTEAYIDSTLPQAQKLADDQGLVLMTTVA |
| Consensus  | (421) | ISTLADVQENVMEYLHVLSRPKVIDQEHDVVWTEAYIDS        LADDQGLVLMTTVA |
|            |       | 481                                                         540 |
| AF486278   | (475) | MPVFSKQNETRSKGILLGVVGTDVPVKELLKTIPKYKLGIHGYAFAITNNGYILTHPELR |
| SEQ ID NO 6 | (481)| MPVFSKQNETRSKGILLGVVGTDVPVKELLKTIPKYKLGIHGYAFAITNNGYILTHPELR |
| Consensus  | (481) | MPVFSKQNETRSKGILLGVVGTDVPVKELLKTIPKYKLGIHGYAFAITNNGYILTHPELR |
|            |       | 541                                                         600 |
| AF486278   | (535) | PLYEEGKKRRKPNYSSVDLSEVEWEDRDDVLRNAMVNRKTGKFSMEVKKTVDKGKRVLVM |
| SEQ ID NO 6 | (541)| PLYEEGKKRRKPNYSSVDLSEVEWEDRDDVLRNAMVNRKTGKFSMEVKKTVDKGKRVLVM |
| Consensus  | (541) | PLYEEGKKRRKPNYSSVDLSEVEWEDRDDVLRNAMVNRKTGKFSMEVKKTVDKGKRVLVM |
|            |       | 601                                                         660 |
| AF486278   | (595) | TNDYYYTDIKGAPFSLGVALSRGHGKYFFRGNVTIEEGLHDLEHPDVSLADEWSYCNTDL |
| SEQ ID NO 6 | (601)| TNDYYYTDIKGAPFSLGVALSRGHGKYFFRGNVTIEEGLHDLEHPDVSLADEWSYCNTDL |
| Consensus  | (601) | TNDYYYTDIKGAPFSLGVALSRGHGKYFFRGNVTIEEGLHDLEHPDVSLADEWSYCNTDL |
|            |       | 661                                                         720 |
| AF486278   | (655) | HPEHRHLSQLEAIKLYLKGKEPLLQCDKELIQEVLFDAVVSAPIEAYWTSLALNKSENSD |
| SEQ ID NO 6 | (661)| HPEHRHLSQLEAIKLYLKGKEPLLQCDKELIQEVLFDAVVSAPIEAYWTSLALNKSENSD |
| Consensus  | (661) | HPEHRHLSQLEAIKLYLKGKEPLLQCDKELIQEVLFDAVVSAPIEAYWTSLALNKSENSD |
|            |       | 721                                                         780 |
| AF486278   | (715) | KGVEVAFLGTRTGLSRINLFVGAEQLTNQDFLKARDKENIFNADHFPLWYRRAAEQIPGS |
| SEQ ID NO 6 | (721)| KGVEVAFLGTRTGLSRINLFVGAEQLTNQDFLKARDKENIFNADHFPLWYRRAAEQIPGS |
| Consensus  | (721) | KGVEVAFLGTRTGLSRINLFVGAEQLTNQDFLKARDKENIFNADHFPLWYRRAAEQIPGS |
|            |       | 781                                                         840 |
| AF486278   | (775) | FVYSIPFSTGTVNKSNVVTASTSIQLLDERKSPVVAAVGIQMKLEFFQRKFWTASRQCAS |
| SEQ ID NO 6 | (781)| FVYSIPFSTGTVNKSNVVTASTSIQLLDERKSPVVAAVGIQMKLEFFQRKFWMASRQCAS |
| Consensus  | (781) | FVYSIPFSTGTVNKSNVVTASTSIQLLDERKSPVVAAVGIQMKLEFFQRKFW ASRQCAS |
|            |       | 841                                                         900 |
| AF486278   | (835) | LDGKCSISCDDETVNCYLIDNNGFILVSEDYTQTGDFFGEVEGAVMNKLLTMGSFKRITL |
| SEQ ID NO 6 | (841)| LDGKCSISCDDETVNCYLIDNNGFILVSEDYTQTGDFFGEVEGAVMNKLLTMGSFKRITL |
| Consensus  | (841) | LDGKCSISCDDETVNCYLIDNNGFILVSEDYTQTGDFFGEVEGAVMNKLLTMGSFKRITL |
|            |       | 901                                                         960 |
| AF486278   | (895) | YDYQAMCRANKESSDSAHGLLDPYKAFLSAAKWIVTELVLFLVEFNLCSWWHSDMTAKAQ |
| SEQ ID NO 6 | (901)| YDYQAMCRANKESSDSAHGLLDPYKAFLSAAKWIVTELVLFLVEFNLCSWWHSDMTAKAQ |
| Consensus  | (901) | YDYQAMCRANKESSDSAHGLLDPYKAFLSAAKWIVTELVLFLVEFNLCSWWHSDMTAKAQ |
|            |       | 961                                                        1020 |

Figure 2A

```
AF486278   (955) KLKQTLEPCDTEYPAFVSERTIKETTGNIACEDCSKSFVIQQIPSSNLFMVVDSSCLCE
SEQ ID NO 6 (961) KLKQTLEPCDTEYPAFVSERTIKETTGNIACEDCSKSFVIQQIPSSNLFMVVDSSCLCE
 Consensus  (961) KLKQTLEPCDTEYPAFVSERTIKETTGNIACEDCSKSFVIQQIPSSNLFMVVDSSCLCE
                  1021                                                     1080
AF486278  (1015) SVAPITMAPIEIRYNESLKCERLKAQKIRRRPESCHGFHPEENARECGGASSLQAQVALL
SEQ ID NO 6 (1021) SVAPITMAPIEIRYNESLKCERLKAQKIRRRPESCHGFHPEENARECGGASSLQAQVALL
 Consensus (1021) SVAPITMAPIEIRYNESLKCERLKAQKIRRRPESCHGFHPEENARECGGASSLQAQVALL
                  1081    1092
AF486278  (1075) LLPLVSSLFSR-
SEQ ID NO 6 (1081) LLPLVSSLFSR-
 Consensus (1081) LLPLVSSLFSR
```

Amino Acid Identity: 99.2%

Figure 2B

```
              1                                                            60
AF486278    (1) MAGPGSLCCASRGASALLATALLYAALGDVVRSEQQIPLSVVKLWASAFGGEIKSIAAKY
SEQ ID 9    (1) MAGPGSLCCASRGASALLATALLYAALGDVVRSEQQIPLSVVKLWASAFGGEIKSIAAKY
Consensus   (1) MAGPGSLCCASRGASALLATALLYAALGDVVRSEQQIPLSVVKLWASAFGGEIKSIAAKY
              61                                                          120
AF486278   (61) SGSQLLQKKYKEYEKDVAIEEIDGLQLVKKLAKNMEEMFHKKSEAVRRLVEAAEEAHLKH
SEQ ID 9   (61) SGSQLLQKKYKEYEKDVAIEEIDGLQLVKKLAKNMEEMFHKKSEAVRRLVEAAEEAHLKH
Consensus  (61) SGSQLLQKKYKEYEKDVAIEEIDGLQLVKKLAKNMEEMFHKKSEAVRRLVEAAEEAHLKH
             121                                                          180
AF486278  (121) EFDADLQYEYFNAVLINERDKDGNFLELGKEFILAPNDHFNNLPVNISLSDVQVPTNMYN
SEQ ID 9  (121) EFDADLQYEYFNAVLINERDKDGNFLELGKEFILAPNDHFNNLPVNISLSDVQVPTNMYN
Consensus (121) EFDADLQYEYFNAVLINERDKDGNFLELGKEFILAPNDHFNNLPVNISLSDVQVPTNMYN
             181                                                          240
AF486278  (181) KDPAIVNGVYWSESLNKVFVDNFDRDPSLIWQYFGSAKGFFRQYPGIKWEPDENGVIAFD
SEQ ID 9  (181) KDPAIVNGVYWSESLNKVFVDNFDRDPSLIWQYFGSAKGFFRQYPGIKWEPDENGVIAFD
Consensus (181) KDPAIVNGVYWSESLNKVFVDNFDRDPSLIWQYFGSAKGFFRQYPGIKWEPDENGVIAFD
             241                                                          300
AF486278  (241) CRNRKWYIQAATSPKDVVILVDVSGSMKGLRLTIAKQTVSSILDTLGDDDFFNIITYNEE
SEQ ID 9  (241) CRNRKWYIQAATSPKDVVILVDVSGSMKGLRLTIAKQTVSSILDTLGDDDFFNIITYNEE
Consensus (241) CRNRKWYIQAATSPKDVVILVDVSGSMKGLRLTIAKQTVSSILDTLGDDDFFNIITYNEE
             301                                                          360
AF486278  (301) LHYVEPCLNGTLVQADRTNKEHFREHLDKLFAKGIGMLDIALNEAFNVLSDFNHTGQGSI
SEQ ID 9  (301) LHYVEPCLNGTLVQADRTNKEHFREHLDKLFAKGIGMLDIALNEAFNVLSDFNHTGQGSI
Consensus (301) LHYVEPCLNGTLVQADRTNKEHFREHLDKLFAKGIGMLDIALNEAFNVLSDFNHTGQGSI
             361                                                          420
AF486278  (361) CSQAIMLITDGAVDTYDTIFAKYNWPERKVRIFTYLIGREAAFADNLKWMACANKGFFTQ
SEQ ID9   (361) CSQAIMLITDGAVDTYDTIFAKYNWPERKVRIFTYLIGREAAFADNLKWMACANKGFFTQ
Consensus (361) CSQAIMLITDGAVDTYDTIFAKYNWPERKVRIFTYLIGREAAFADNLKWMACANKGFFTQ
             421                                                          480
AF486278  (421) ISTLADVQENVMEYLHVLSRPKVIDQEHDVVWTEAYIDST------LADDQGLVLMTTVA
SEQ ID 9  (421) ISTLADVQENVMEYLHVLSRPKVIDQEHDVVWTEAYIDSTLPQAQKLADDQGLVLMTTVA
Consensus (421) ISTLADVQENVMEYLHVLSRPKVIDQEHDVVWTEAYIDS      LADDQGLVLMTTVA
             481                                                          540
AF486278  (475) MPVFSKQNETRSKGILLGVVGTDVPVKELLKTIPKYKLGIHGYAFAITNNGYILTHPELR
SEQ ID 9  (481) MPVFSKQNETRSKGILLGVVGTDVPVKELLKTIPKYKLGIHGYAFAITNNGYILTHPELR
Consensus (481) MPVFSKQNETRSKGILLGVVGTDVPVKELLKTIPKYKLGIHGYAFAITNNGYILTHPELR
             541                                                          600
AF486278  (535) PLYEEGKKRRKPNYSSVDLSEVEWEDRDDVLRNAMVNRKTGKFSMEVKKTVDKGKRVLVM
SEQ ID 9  (541) PLYEEGKKRRKPNYSSVDLSEVEWEDRDDVLRNAMVNRKTGKFSMEVKKTVDKGKRVLVM
Consensus (541) PLYEEGKKRRKPNYSSVDLSEVEWEDRDDVLRNAMVNRKTGKFSMEVKKTVDKGKRVLVM
             601                                                          660
AF486278  (595) TNDYYYTDIKGAPFSLGVALSRGHGKYFFRGNVTIEEGLHDLEHPDVSLADEWSYCNTDL
SEQ ID 9  (601) TNDYYYTDIKGAPFSLGVALSRGHGKYFFRGNVTIEEGLHDLEHPDVSLADEWSYCNTDL
Consensus (601) TNDYYYTDIKGAPFSLGVALSRGHGKYFFRGNVTIEEGLHDLEHPDVSLADEWSYCNTDL
             661                                                          720
AF486278  (655) HPEHRHLSQLEAIKLYLKGKEPLLQCDKELIQEVLFDAVVSAPIEAYWTSLALNKSENSD
SEQ ID 9  (661) HPEHRHLSQLEAIKLYLKGKEPLLQCDKELIQEVLFDAVVSAPIEAYWTSLALNKSENSD
Consensus (661) HPEHRHLSQLEAIKLYLKGKEPLLQCDKELIQEVLFDAVVSAPIEAYWTSLALNKSENSD
             721                                                          780
AF486278  (715) KGVEVAFLGTRTGLSRINLFVGAEQLTNQDFLKARDKENIFNADHFPLWYRRAAEQIPGS
SEQ ID 9  (721) KGVEVAFLGTRTGLSRINLFVGAEQLTNQDFLKARDKENIFNADHFPLWYRRAAEQIPGS
Consensus (721) KGVEVAFLGTRTGLSRINLFVGAEQLTNQDFLKARDKENIFNADHFPLWYRRAAEQIPGS
             781                                                          840
AF486278  (775) FVYSIPFSTGTVNKSNVVTASTSIQLLDERKSPVVAAVGIQMKLEFFQRKFWTASRQCAS
SEQ ID 9  (781) FVYSIPFSTGTVNKSNVVTASTSIQLLDERKSPVVA------------------------
Consensus (781) FVYSIPFSTGTVNKSNVVTASTSIQLLDERKS
             841                                                          900
AF486278  (835) LDGKCSISCDDETVNCYLIDNNGFILVSEDYTQTGDFFGEVEGAVMNKLLTMGSFKRITL
SEQ ID 9  (813) ------------------------------------------------------------
Consensus (841)
             901                                                          960
AF486278  (895) YDYQAMCRANKESSDSAHGLLDPYKAFLSAAKWIVTELVLFLVEFNLCSWWHSDMTAKAQ
SEQ ID 9  (814) ---------------------------------------------------------AQ
Consensus (901)                                                          AQ
             961                                                         1020
```

Figure 3A

```
AF486278    (955)  KLKQTLEPCDTEYPAFVSERTIKETTGNIACEDCSKSFVIQQIPSSNLFMVVVDSSCLCE
SEQ ID 9    (819)  KLKQTLEPCDTEYPAFVSERTIKETTGNIACEDCSKSFVIQQIPSSNLFMVVVDSSCLCE
Consensus   (961)  KLKQTLEPCDTEYPAFVSERTIKETTGNIACEDCSKSFVIQQIPSSNLFMVVVDSSCLCE
                   1021                                                     1080
AF486278   (1015)  SVAPITMAPIEIRYNESLKCERLKAQKIRRRPESCHGFHPEENARECGGASSLQAQVALL
SEQ ID 9    (879)  SVAPITMAPIEIRYNESLKCERLKAQKIRRRPESCHGFHPEENARECGGASSLQAQVALL
Consensus  (1021)  SVAPITMAPIEIRYNESLKCERLKAQKIRRRPESCHGFHPEENARECGGASSLQAQVALL
                   1081      1091
AF486278   (1075)  LLPLVSSLFSR
SEQ ID 9    (939)  LLPLVSSLFSR
Consensus  (1081)  LLPLVSSLFSR
```

Sequence identity 86.0%

Figure 3B

RAT CALCIUM CHANNEL SUBUNITS AND RELATED PROBES, CELL LINES AND METHODS

CROSS-REFERENCE TO RELATED APPLICATION

This application claims benefit of U.S. provisional application No. 60/497,096 filed 22 Aug. 2003. The contents of this document is incorporated herein by reference in its entirety.

TECHNICAL FIELD

The present invention relates to novel calcium channel $\alpha_2\delta$-2 and $\alpha_2\delta$-3 DNA and protein compositions, and to the expression of these compositions in cell lines for use in evaluating calcium channel function and in screening for agonists/antagonists for these channels.

BACKGROUND ART

Voltage-gated calcium channels are a heterogeneous family of membrane proteins, which respond to depolarization by opening a calcium-selective pore through the plasma membrane. The influx of calcium into cells mediates a wide variety of cellular and physiological responses including excitation-contraction coupling, hormone secretion and gene expression. In neurons, calcium entry directly affects membrane potential and contributes to electrical properties such as excitability, repetitive firing patterns and pacemaker activity. Calcium entry further affects neuronal function by directly regulating calcium-dependent ion channels and modulating the activity of enzymes such as protein kinase C and calcium-dependent calmodulin-dependent protein kinase II. Furthermore, an increase in calcium concentration at the presynaptic nerve terminal triggers the release of neurotransmitters. Calcium entry also plays a role in neurite outgrowth and growth cone migration in developing neurons and is implicated in long-term changes in neuronal activity. In addition to the variety of normal physiological functions mediated by calcium channels, they are also implicated in a number of human disorders. Recently, mutations identified in human and mouse calcium channel genes were found to account for several disorders including, familial hemiplegic migraine, episodic ataxia type 2, cerebellar ataxia, absence epilepsy and seizures. (See, for example, Fletcher, C. F., et al., *Cell* (1996) 87:607–617; Burgess, D. L., et al., *Cell* (1997) 88:385–392; Ophoff, R. A., et al., *Cell* (1996) 87:543–552; Zhuchenko, O., et al., *Nature Genetics* (1997) 15:62–69. The clinical treatment of some disorders has been aided by the development of therapeutic calcium channel modulators or blockers. Janis, R. J. and Triggle, D. J. (1991) in *Calcium Channels: Their Properties, Functions, Regulation and Clinical Relevance*, CRC Press, London).

Native calcium channels are classified by their electrophysiological and pharmacological properties as either high voltage-activated (L, N, P, and Q types) or low voltage-activated channels (T-type). R-type channels have biophysical properties similar to both high and low voltage-activated channels. (For reviews see McCleskey, E. W. and Schroeder, J. E., *Curr. Topics Membr.* (1991) 39:295–326, and Dunlap, K., et al., *Trends Neurosci.* (1995) 18:89–98.) T-type channels are a broad class of molecules that transiently activate at negative potentials and are highly sensitive to changes in resting potential. The L, N, P and Q-type channels activate at more positive potentials and display diverse kinetics and voltage-dependent properties. There is some overlap in biophysical properties among the high voltage-activated channels, consequently pharmacological profiles are useful to further distinguish them. L-type channels are sensitive to dihydropyridine (DHP) blockers, N-type channels are blocked by the *Conus geographus* peptide toxin, ω-conotoxin GVIA, and P-type channels are blocked by the peptide ω-agatoxin IVA from the venom of the funnel web spider, *Agelenopsis aperta*. A fourth type of high voltage-activated $Ca^{2+}$ channel (Q-type) has been described, although whether the Q- and P-type channels are distinct molecular entities is controversial. Conductance measurements of several types of calcium channels have not always fallen neatly into any of the above classes and there is variability of properties even within a class, suggesting that additional calcium channels subtypes remain to be classified.

Biochemical analyses show that neuronal calcium channels are heterooligomeric complexes consisting of three distinct subunits ($\alpha_1$, $\alpha_2\delta$ and $\beta$) (reviewed by De Waard, M., et al., in *Ion Channels, Volume 4*, (1997) edited by Narahashi, T., Plenum Press, New York). The $\alpha$1 subunit is the major pore-forming subunit and contains the voltage sensor and binding sites for calcium channel blockers. The mainly extracellular $\alpha$2 is disulphide-linked to the transmembrane $\delta$ subunit and both are derived from the same gene and are proteolytically cleaved in vivo. The $\beta$ subunit is a non-glycosylated, hydrophilic protein with a high affinity of binding to a cytoplasmic region of the $\alpha$1 subunit. A fourth subunit, $\gamma$, is unique to L-type calcium channels expressed in skeletal muscle T-tubules. The isolation and characterization of $\gamma$-subunit-encoding cDNA's is described in U.S. Pat. No. 5,386,025, which is incorporated herein by reference.

The DNA's encoding the amino acid sequences of seven different types of $\alpha$1 subunits ($\alpha_1$A, $\alpha_1$B, $\alpha_1$C, $\alpha_1$D, $\alpha_1$E, $\alpha_1$F and $\alpha_1$S) and four types of $\beta$ subunits ($\beta_1$, $\beta_2$, $\beta_3$ and $\beta_4$) have been cloned. (Reviewed in Stea, A., et al., "Voltage-gated calcium channels" in *Handbook of Receptors and Channels* (1994) Edited by R. A. North, CRC Press). PCT Patent Publication WO 95/04144, which is incorporated herein by reference, discloses the sequence and expression of $\alpha_1$E calcium channel subunits.

In some expression systems the a, subunits alone can form functional calcium channels although their electrophysiological and pharmacological properties can be differentially modulated by coexpression with any of the four $\beta$ subunits. Until recently, the reported modulatory affects of $\beta$ subunit coexpression were to mainly alter kinetic and voltage-dependent properties. It has now been shown that $\beta$ subunits also play crucial roles in modulating channel activity by protein kinase A, protein kinase C and direct G-protein interaction. (Bourinet, E., et al., *EMBO J.* (1994)13: 5032–5039; Stea, A., etal., *Neuron* (1995) 15:929–940; Bourinet, E., et al., *Proc. Natl. Acad. Sci.* (*USA*) (1996) 93:1486–1491.)

The $\alpha_2\delta$ subunits comprise at least four types encoded by different genes. The first subunit identified was $\alpha2\delta$-1 from rabbit skeletal muscle (Ellis, et al., *Science* (1988) 241: 1661–1664). Five tissue-specific splice variants exist (Angelotti, T. and Hofmann, F., *FEBS Lett.* (1996) 397:331–337). $\alpha_2\delta$-2, -3 and -4 have been identified recently in human and mouse (Klugbauer, N., et al., *J. Neuroscience* (1999) 19:684–691; Qin, N., et al., *Mol. Pharmacol.* (2002) 62:485–496). These $\alpha_2\delta$ subunits share 30% to 56% amino acid identity with the $\alpha_2\delta$-1 subunit as well as several structural motifs, such as similar hydrophobicity profiles, glycosylation sites and cysteine residues. $\alpha_2\delta$-1 and $\alpha_2\delta$-2 subunits are expressed in many tissues including the brain and heart, while $\alpha_2\delta$-3 is found only in the brain (Klugbauer, et al., 1999 (supra)). A recent report showed that IGF-1 stimulates $\alpha_2\delta$-3 expression in cultured rat atrial myocytes. (Chu, P.-J., *J. Mol. Cell. Cardiology* (2003) 35:207–215.) The $\alpha_2\delta$-4 subunit is distributed in certain cell types of the pituitary, adrenal gland, colon and fetal liver (Qin, et al., 2002 (supra)).

A number of physiological roles have been proposed for the $\alpha_2\delta$-2 subunit, including acting as a tumor suppressor gene, and a mutation in the mouse homolog, resulting in a truncated $\alpha_2\delta$-2 has been identified as a contributing factor to the ducky epileptic phenotype (Gao, B., et al., *J. Biol. Chem.* (2000) 275:12237–12242; Brodbeck, J., et al., *J. Biol. Chem.* (2002) 277:7684–7693). The antiepileptic gabapentin binds to the $\alpha_2\delta$-1 and -2 subunits, but not to $\alpha_2\delta$-3 (Marais, E., et al., *Molec. Pharmacol.* (2001) 59:1243–1248).

$\alpha_2\delta$-1 increases the current density of calcium channels by increasing the amount of functional channel at the cell surface and enhances dihydropyridine binding to L-type channels and $\omega$-conotoxin GVIA to N-type channels (Brust, P. F., et al., *Neuropharmacology* (1993) 32:1089–1102; Felix, R., et al., *J. Neurosci.* (1997) 17:6884–6891). $\alpha_2\delta$-2 and $\alpha_2\delta$-3 significantly enhance and modulate the $Ca^{2+}$ current through a number of HVA and LVA channels (Klugbauer, et al. (1999) (supra); Gao, et al. (2000) (supra); Hobom, M., et al., *Eur. J. Neurosci.* (2000) 12:1217–1226).

Recently, the molecular cloning of $\alpha_2\delta$-2 and $\alpha_2\delta$-3 subunits from rat atria was reported. (Chu, P-.J., et al., 2003 (supra)). Cloning of rat $\alpha_2\delta$-2 and $\alpha_2\delta$-3 subunits from rat brain tissue has not been previously disclosed.

DISCLOSURE OF THE INVENTION

The materials and methods of the present invention add to the repertoire of rat $\alpha_2\delta$-2 and $\alpha_2\delta$-3 calcium channel subunits previously known. Also provided are cell lines that express the novel calcium channels of the invention. These cells may be used for identifying compounds capable of acting as agonists or antagonists to the calcium channels.

Thus, in one aspect, the invention is directed to isolated nucleic acid molecules which contain a nucleotide sequence that encodes a protein having the amino acid sequence that is shown in SEQ. ID. NO:3, 6, 9 or 11, or a functional portion thereof. In another aspect, the invention relates to the $\alpha_2\delta$-2 and $\alpha_2\delta$-3 subunits themselves in isolated form that have an amino acid sequence that is shown in SEQ. ID. NO:3, 6, 9 or 11, or fragment of said sequence which retains the activity of this subunit. The invention is also directed to recombinant materials and methods for production of these proteins and displaying them on cells. When displayed on cells which also produce, contain and display at least an $\alpha_1$ subunit, the $\alpha_2\delta$-2 and $\alpha_2\delta$-3 subunits of the invention in combination with the a, subunit provide active calcium ion channels which can be used to identify agonists and antagonists of calcium ion channel activity.

In other aspects, the invention is directed to nucleic acid probes that are specific for the particular $\alpha_2\delta$-2 and $\alpha_2\delta$-3 subunit mRNA's of the invention which permit the detection of expressed mRNA encoding the $\alpha_2\delta$-2 or $\alpha_2\delta$-3 protein. In addition, antibodies which are immunospecific for the particular $\alpha_2\delta$-2 and $\alpha_2\delta$-3 proteins of the invention can be used to map the distribution of the protein in cells and tissues.

BRIEF DESCRIPTION OF THE DRAWINGS

The data in FIGS. 1A and 1B show a comparison of the amino acid sequence of the rat brain $\alpha_2\delta$-2 calcium channel subunit (SEQ. ID. NO:3) to that of the rat atria $\alpha_2\delta$-2 calcium channel subunit (AF486277; SEQ. ID. NO:1).

The data in FIGS. 2A and 2B show a comparison of the amino acid sequence of the rat brain $\alpha_2\delta$-3 calcium channel subunit (SEQ. ID. NO:6) to that of the rat atria $\alpha_2\delta$-3 calcium channel subunit (AF486278; SEQ. ID. NO:4).

Figure 4:
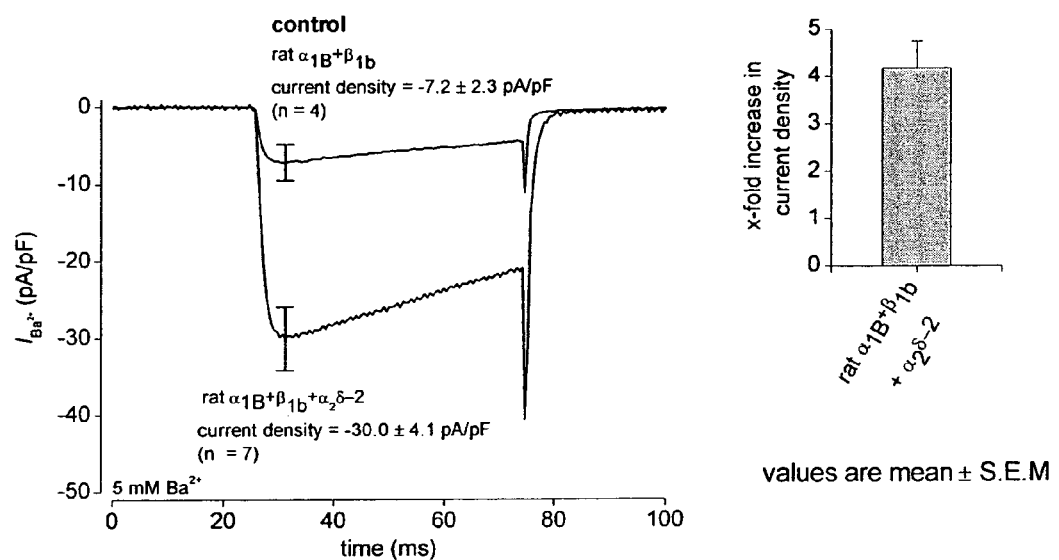

The data in FIGS. 3A and 3B show a comparison of the amino acid sequence of the rat brain $\alpha_2\delta$-3 calcium channel subunit splice variant (SEQ. ID. NO:9) to that of the rat atria $\alpha_2\delta$-3 calcium channel subunit (AF486278 SEQ. ID. NO:4).

The data in FIG. 4 show rat $\alpha_{1B}+\beta_{1b}$ $Ca^{2+}$ channel current density when tested in the presence and absence of rat $\alpha_2\delta$-2.

MODES FOR CARRYING OUT THE INVENTION

The present invention provides amino acid sequences for novel rat calcium channel $\alpha_2\delta$-2 and $\alpha_2\delta$-3 subunits, as well as nucleic acid sequences which encode these subunits. As described in the Background section above, it is understood that $\alpha_2\delta$ subunits alone do not mediate transport calcium across the cellular membrane; however, they increase the current density of calcium channels by increasing the amount of functional channel at the cell surface and enhancing binding of certain ligands. Typically, the $\alpha_2\delta$ subunits require the presence of an $\alpha_1$ subunit, and are preferably expressed or assessed in the additional presence of $\beta$ type subunits. If the $\alpha_1$ subunit employed is from an L-type channel, the additional presence of a $\gamma$ subunit is also desirable.

As described in the Background section above, there appear to be four specific types of this subunit, $\alpha_2\delta$-1, $\alpha_2\delta$-2, $\alpha_2\delta$-3 and $\alpha_2\delta$-4. While in their native expression, each of these types may preferentially be associated with a particular class of calcium ion channel (e.g., L, P/Q, N, T and the like), each of these subunits is functional when in association with any $\alpha_1$ subunit with the optional addition of any type of $\beta$ subunit. Although the text herein refers to $\alpha_2\delta$ because this is the protein encoded by a single gene, the encoded protein is hydrolyzed after translation into the $\alpha_2$ and $\delta$ portions; the $\alpha_2$ portion is mostly extracellular and is disulfide linked to the $\delta$ subunit which remains in the cell membrane. By "functional $\alpha_2\delta$ subunit" is meant the entire amino acid sequence encoded by the gene or any portion thereof which, when associated with an $\alpha_1$ subunit and optionally a $\beta$ subunit enhances the density of current flow in the calcium ion channel thus created. Thus, is it understood that small numbers of amino acids, e.g., 10–15 or 20 amino acids might be removed from each of the $\alpha_2$ and/or $\delta$ portions while the remainder of the sequence retains functionality as described above. Thus, a "functional portion of the $\alpha_2\delta$ subunit" refers to these truncated forms.

A compound, such as a nucleic acid molecule or a protein is referred to as "isolated" when it is removed from its natural environment. It may or may not be pure. "Isolated" simply means that the molecule is in a context where it is not found in nature. For example, a nucleic acid comprising a particular nucleotide sequence is "isolated" when contained in a recombinant DNA molecule coupled to additional nucleotide sequences with which it is not normally associated. Similarly, the "protein" is isolated when it is not in the context of its native cell. "Isolated" $\alpha_2\delta$-2 and $\alpha_2\delta$-3 subunits, for example, are frequently found in the context of a displayed calcium ion channel in a heterologous cell which has been modified to produce this protein.

Although in some instances, an $\alpha_1$ subunit displayed at a cellular surface may be functional at some level in the absence of additional subunit types, the presence of the $\alpha_2\delta$ subunit greatly enhances the current density when the channel is activated. Accordingly, the production of $\alpha_2\delta$-2 and/or $\alpha_2\delta$-3 subunits for display on cells which also display at least $\alpha_1$ subunits is important for use in screening assays to identify compounds that modulate the activity of the calcium ion channel.

The particular $\alpha_2\delta$-2 and $\alpha_2\delta$-3 subunits that constitute the present invention were isolated and identified from rat brain. The amino acid sequence set forth as SEQ. ID. NO:3 is an $\alpha_2\delta$-2 calcium channel subunit which is present in rat brain. SEQ. ID. NO:3 is 1,150 amino acids in length and has a molecular weight of 130 kDa. It is encoded by a nucleotide sequence containing 3,450 base pairs (bp) which is contained in the 4,993 bp sequence shown as SEQ. ID. NO:2. A full-length cDNA clone of 4,993 bp was constructed using a PCR fragment of 556 bp amplified from brain total RNA and a 4,507 bp fragment obtained from a brain cDNA library.

There is 95.5% and 90.5% nucleotide sequence identity of the rat $\alpha_2\delta$-2 cDNA coding region compared to that of the mouse and human $\alpha_2\delta$-2 subunits, respectively. A conceptual translation of the cDNA sequence shows that the rat $\alpha_2\delta$-2 amino acid sequence shares 97.9% and 95.7% identity compared to the mouse and human $\alpha_2\delta$-2 subunits, respectively.

It will be appreciated that polymorphic variations may be made or may exist in the $\alpha_2\delta$-2 and $\alpha_2\delta$-3 DNA of some individuals leading to minor deviations in the DNA or amino acids sequences from those shown which do not lead to any substantial alteration in the function of the calcium channel. Such variants, including variations that lead to substitutions of amino acids having similar properties are considered to be within the scope of the present invention.

An examination of the nucleotide sequence contained in SEQ. ID. NO:2 shows a Kozak consensus translation initiation sequence at the second start (AUG) codon. The encoded protein is predicted to have six N-glycosylated asparagines and a hydrophobicity profile similar to that of the rat $\alpha_2\delta$-1 subunit. There are 15 conserved cysteine residues in the rat $\alpha_2\delta$-2 protein, which correspond to those in the other mammalian $\alpha_2\delta$-2 proteins.

The $\alpha_2\delta$-2 subunit of SEQ. ID. NO:3 is 98.5% identical to the rat atrial $\alpha_2\delta$-2 subunit previously described (Accession Number AF486277, SEQ. ID. NO:1). See FIG. 1 for comparative alignment of these sequences. There are several single point amino acid differences between the brain and atrial subunits. The atrial $\alpha_2\delta$-2 also contains an eight amino acid insert of LPISKLKD (SEQ. ID. NO:7) at residues 665–672, suggesting that the brain and atrial subunits are splice variants. The $\alpha_2\delta$-2 subunits expressed in human and mouse brain also lack this insert.

The amino acid sequence set forth as SEQ ID NO:11 is an $\alpha_2\delta$-2 calcium channel variant which is present in rat brain. Without being bound by theory, this $\alpha_2\delta$-2 subunit appears to be a splice variant of the $\alpha_2\delta$-2 subunit of SEQ ID NO:3. The rat $\alpha_2\delta$-2 variant nucleotide sequence (SEQ ID NO:10) contains an insertion of 21 bases in comparison to the $\alpha_2\delta$-2 subunit nucleotide sequence SEQ ID NO:2. The insertion is found at nucleotides 1,994 to 2,014 in SEQ ID NO:10 (see nucleotides underlined and in bold in SEQ ID NO:10 sequence below).

The variant brain $\alpha_2\delta$-2 subunit contains an insertion of eight amino acids, LIPSKLKD (SEQ ID NO:7) at residues 665–672 in comparison to the $\alpha_2\delta$-2 subunit SEQ ID NO:3 (see amino acids underlined and in bold in SEQ ID NO:11 sequence below). This rat brain $\alpha_2\delta$-2 subunit variant protein sequence is 99.2% identical to the rat atrial $\alpha_2\delta$-2 subunit previously described (AF486277, SEQ ID NO:1).

This eight amino acid insertion is also found in the rat atrial $\alpha_2\delta$-2 subunit (see SEQ ID NO:1). The variant brain $\alpha_2\delta$-2 subunit is also expressed in human and mouse brain.

The amino acid sequence set forth as SEQ. ID. NO:6 is an $\alpha_2\delta$-3 calcium channel subunit which is present in rat brain. SEQ. ID. NO:6 is 1,091 amino acids in length and has a molecular weight of 123 kDa. It is encoded by a nucleotide sequence containing 3,273 bp which is contained in the 3,598 bp sequence shown in SEQ. ID. NO:5. A full-length cDNA clone of 3,598 bp was constructed using a PCR fragment of 1,618 bp amplified from rat brain total RNA and a 1,981 bp fragment isolated from a rat brain cDNA library.

An examination of the encoded protein in SEQ. ID. NO:6 shows a signal peptide cleavage site between residues 33 and 34, VRS-EQ. There are also four highly predictable N-glycosylation sites and 19 conserved cysteine residues between the rat, mouse and human protein sequences.

The rat brain $\alpha_2\delta$-3 DNA sequence has 86.5% and 95.9% identity to the human and mouse $\alpha_2\delta$-3 sequences, respectively. A conceptual translation of the cDNA sequence shows that the rat $\alpha_2\delta$-3 amino acid sequence shares 89.5% and 99.2% identity compared to the human and mouse, respectively.

The rat brain $\alpha_2\delta$-3 subunit cDNA sequence of SEQ. ID. NO:5 and protein sequence of SEQ. ID. NO:6 is 91.0% and 99.4%, respectively, identical to that of the rat atrial $\alpha_2\delta$-3 subunit previously described (AF486278, SEQ. ID. NO:4). See FIG. 2 for alignment of these sequences. The human $\alpha_2\delta$-3 subunit is 997 amino acids while the rat brain $\alpha_2\delta$-3 sequence (SEQ. ID. NO:6) is 1, 91 amino acids. The longer 5' region in the rat accounts for the 94 amino acid difference between human and rat.

The amino acid sequence set forth as SEQ. ID. NO:9 is an $\alpha_2\delta$-3 calcium channel subunit variant which is present in rat brain. Without being bound by theory, this $\alpha_2\delta$-3 subunit appears to be a splice variant of the full-length $\alpha_2\delta$-3 subunit. This variant $\alpha_2\delta$-3 sequence contains a 142 amino acid deletion of amino acid residues 817–958 in comparison to the full-length $\alpha_2\delta$-3 amino acid sequence (SEQ. ID. NO:6). This rat brain $\alpha_2\delta$-3 subunit variant protein sequence is 86% identical to the rat atrial $\alpha_2\delta$-3 subunit previously described (AF486278, SEQ. ID. NO:4). See FIG. 3 for comparison.

Both the full-length and variant brain $\alpha_2\delta$-3 subunits contain an insertion of six amino acids, LPQAQK (SEQ ID NO:22), in comparison to the atrial $\alpha_2\delta$-3 subunit. Both human and mouse subunits contain the identical six residue sequence found in rat brain $\alpha_2\delta$-3. The full-length brain $\alpha_2\delta$-3 subunit also contains a single residue change in comparison to the atrial $\alpha_2\delta$-3 subunit.

When the $\alpha_2\delta$ protein is displayed on cells in the presence of or coexpressed with the $\alpha_1$ subunit of any calcium ion channel and optionally as well, a $\beta$ subunit, the resulting cells are useful in identifying compounds that modulate the activity of the channel. The nature of the channel is effectively determined by the nature of the $\alpha_1$ subunit but, in all cases, the $\alpha_2\delta$ subunit enhances current flux so that a more accurate measurement can be made. A malfunction of calcium ion channels is associated with a number of conditions; depending on the nature of the channel. For example, defects in calcium channels are associated with conditions including, but not limited to: epilepsy, migraine, ataxia, schizophrenia, hypertension, arrhythmia, angina, depression, small lung carcinoma, Lambert-Eaton syndrome.

Compounds identified that agonize or antagonize the various calcium ion channels are thus suitable drug candidates for treatment of these conditions. It is understood that not all agonists and antagonists thus identified will ultimately become successful drugs; however, the identification of a subpopulation of the millions of molecules that would otherwise be candidates represents a giant step toward development of a suitable drug.

While the required display of the calcium ion channels which include the $\alpha_2\delta$ subunits of the invention may be effected in a variety of animal cells, exemplary cells include *Xenopus* oocytes or mammalian cells such as human embryonic kidney (HEK 293) cells as described in PCT Publication No. WO 96/39512, incorporated herein by reference, and Ltk cells as described in U.S. Pat. No. 5,386,025, incorporated herein by reference. Transfection into host cells is accomplished by, for example, microinjection, lipofection, electroporation, calcium phosphate (glycerol shock) or particle-mediated gene transfer.

Mammalian cell lines stably expressing rat brain $\alpha_2\delta$-2 or $\alpha_2\delta$-3 calcium channels are, for example, prepared by transfecting an expression vector containing the $\alpha_2\delta$-2 calcium channel cDNA or the $\alpha_2\delta$-3 calcium channel cDNA into mammalian cells, such as HEK 293 cells, and selecting for cells containing the expression vector, for example, by selecting for the antibiotic resistance encoded by the expression vector, for example, pBK-RSV or pcDNA with a selectable marker (Invitrogen, San Diego, Calif.). The vectors are transfected into HEK 293 cells by calcium phosphate coprecipitation or lipofection or electroporation or any other method according to well known procedures (Methods in Enzymologzy Volume 185, "Gene Expression Technology" (1990) Edited by Goeddel, D. V.). The rat brain $\alpha_2\delta$-2 or $\alpha_2\delta$-3 calcium channel subunit cDNA expression vector may be transfected alone, or in combination with other rat, human or other mammalian or other animal calcium channel subunit cDNA's, such as the $\alpha_{1B}$ and $\beta_{1b}$ subunit cDNA's, either in a similar expression vector or other type of vector using different selectable markers. Transfected cells are typically incubated for 4–16 hours under transfection conditions at 37° C., 5% $CO_2$, then placed in nonselective medium for an additional 24 hours. The cells are trypsinized and plated at low density in selective medium containing, for example, Geneticin (G418) between 600 to 800 µg/ml or Zeocin between 25–200 µg/ml, depending upon the particular vector. After 10–16 days in selective medium, cells that are resistant to G418 or zeocin grow as visible colonies and isolated colonies are harvested by the pipet technique or using standard cloning rings. Isolated cell colonies are then expanded to make frozen stocks of cells and to determine the level of rat $\alpha_2\delta$-2 or $\alpha_2\delta$-3 subunit expression. Southern blotting can be used to detect the integration of the subunit nucleotide sequence into the cell genome, the presence of the plasmid episomally, and the number of copies present. Rat $\alpha_2\delta$-2 and $\alpha_2\delta$-3 expression levels for the cell lines are determined using standard gene expression methods such as Northern blotting, RNase protection, reverse-transcriptase PCR, and Western blotting.

The functional detection of calcium channels containing the rat $\alpha_2\delta$-2 or $\alpha_2\delta$-3 subunit of the invention in stably transfected cells can be examined electrophysiologically, such as by whole cell patch clamp or single channel analysis, as described herein, for example. Other means of detecting functional calcium channels include the use of radiolabeled $^{45}Ca$ uptake, or fluorescence spectroscopy using calcium sensitive dyes, such as FURA-2.

The resulting cell lines expressing functional calcium channels comprising the $\alpha_2\delta$ subunit of the invention and at least an $\alpha_1$ subunit can then be used as test compounds for pharmacological activity with respect to these calcium channels as set forth above.

Compounds to be tested as agonists or antagonists of the calcium channels are combined with cells that are stably or transiently transformed with a cDNA sequence encoding the rat $\alpha_2\delta$-2 or the $\alpha_2\delta$-3 subunit of the invention with $\alpha_1$ and, optionally, $\beta$ subunits and monitored for pharmacological activity, if any, with respect to these calcium channels. Thus, the cell lines are useful for screening compounds for pharmaceutical utility.

Such screening can be carried out using several available methods for evaluation of the interaction, if any, between the test compound and the calcium channel. One such method involves the binding of radiolabeled agents that interact with the calcium channel and subsequent analysis of equilibrium binding measurements including, but not limited to, on rates, off rates, Kd values and competitive binding by other molecules. Another method involves screening for the effects of compounds by electrophysiological assay whereby individual cells are impaled with a microelectrode and currents through the calcium channel are recorded before and after application of the compound of interest. Another method, high-throughput spectro-photometric assay, utilizes loading the cell lines with a fluorescent dye sensitive to intracellular calcium concentration and subsequent examination of the effects of compounds on the ability of depolarization by potassium chloride or other means to alter intracellular calcium levels.

Compounds that are found to modulate the calcium ion channels, wherein the rat $\alpha_2\delta$-2 or the $\alpha_2\delta$-3 subunit of the invention is used to enhance the signal, and thereby increase the accuracy and reproducibility of results, are useful in treating conditions associated with defects in performance of these channels. The nature of these conditions depends on the type of calcium ion channel involved; but since the $\alpha_2\delta$ subunit of the invention enhances the signal for all types of calcium ion channels, it is useful in detecting compounds for a wide variety of conditions. Defects in calcium channels are associated with conditions including, but not limited to: epilepsy, migraine, ataxia, schizophrenia, hypertension, arrhythmia, angina, depression, small lung carcinoma, Lambert-Eaton syndrome.

Detection of Calcium Ion Channel Expression

Expression of the $\alpha_2\delta$-2 and $\alpha_2\delta$-3 subunits of the invention, and of calcium ion channels that contain the $\alpha_2\delta$ subunits of the invention, can be detected at the mRNA or protein level. Accordingly, in some embodiments, methods of the invention involve assaying biological samples for the presence, absence and/or level of the $\alpha_2\delta$-2 or $\alpha_2\delta$-3 subunit probe target of the invention, such as rat brain $\alpha_2\delta$-2 or $\alpha_2\delta$-3 subunit RNA and/or rat brain $\alpha_2\delta$-2 or $\alpha_2\delta$-3 subunit polypeptide.

It will be readily apparent upon reading of the present specification that the expression detection assays can be conducted as, or modified to be conducted as, in vitro or in vivo assays, and may be either cell-free (e.g., in vitro binding assays using polynucleotides isolated from or produced from nucleic acid of a biological sample) or cell-based (e.g., screening of whole cells for expressing the $\alpha_2\delta$-2 and $\alpha_2\delta$-3 subunits of the invention). In general, all assays are conducted under conditions, and for a period of time, sufficient to allow for specific binding of a rat brain $\alpha_2\delta$-2 or $\alpha_2\delta$-3 subunit-specific probe (e.g., nucleic acid probe, antibody probe) to a rat brain $\delta_2\delta$-2 and/or $\alpha_2\delta$-3 subunit probe target, e.g., to provide for detection of rat brain $\alpha_2\delta$-2 and/or $\alpha_2\delta$-3 subunit probe target at a detectable level above background. The assays can include various positive and/or negative controls, the nature of which will be readily apparent to the ordinarily skilled artisan upon reading the present specification.

Any suitable qualitative or quantitative methods known in the art for detecting specific $\alpha_2\delta$-2 and $\alpha_2\delta$-3 mRNA's can be used to detect or quantitate expression of the $\alpha_2\delta$-2 and $\alpha_2\delta$-3 mRNA of the invention. For example, rat brain $\alpha_2\delta$-2 and $\alpha_2\delta$-3 mRNA in cells can be measured by various techniques known in the art including, but not limited to, S1 nuclease analysis, ribonuclease protection assay, primer extension assay, RNA blot analysis (e.g., northern and/or slot blot hybridization) and amplification techniques including reverse transcriptase-PCR (RT-PCR). In addition, expression can be assessed in histological assays, for example the $\alpha_2\delta$-2 and/or $\alpha_2\delta$-3 RNA of the invention can be detected by in situ hybridization in tissue sections, using methods that detect single base pair differences between hybridizing nucleic acid and other methods well known in the art.

Typically northern blot of total mRNA or fractionated RNA or RT-PCR are employed. The northern blot or RT-PCR product is probed under conditions of high stringency with a fragment of SEQ. ID. NO:2, 5, 8 or 10, or the complement thereof, whichever is appropriate. Typically, the probes contain at least 12 consecutive nucleotides derived from SEQ. ID. NO:2, 5, 8 or 10, or the complement thereof. Conditions of high stringency are defined as wash conditions of 1×SSC, 0.1 SDS, and 60° C. When mRNA encoding the $\alpha_2\delta$ subunits of the invention is present, its presence and amount can thus be detected.

To differentially detect the rat brain $\alpha_2\delta$-2 and $\alpha_2\delta$-3 mRNA's of the invention from their rat atrial counterparts (and likely other $\alpha_2\delta$ mRNA's), probes containing nucleotide sequences which encode the polypeptide regions which differ between the $\alpha_2\delta$-2 and $\alpha_2\delta$-3 proteins of the invention and those known in the art may be used. For example, to specifically detect rat brain $\alpha_2\delta$-2 mRNA from rat atrial $\alpha_2\delta$-2 mRNA, a probe can be used which contains the nucleotide sequence that flanks and includes base pairs 2,015–2,021 of SEQ ID NO:2, for example, a probe containing base pairs 2,011–2,023 of SEQ. ID. NO:2. To specifically detect rat brain $\alpha_2\delta$-2 variant mRNA from rat brain $\alpha_2\delta$-2 mRNA for SEQ ID NO:3 and from rat atrial $\alpha_2\delta$-2 mRNA, a probe can be used which contains the nucleotide sequence that flanks and includes base pairs 1,994 to 2,014 of SEQ ID NO:10 in conjunction a second probe which detects the sequence differences between brain and atrial $\alpha_2\delta$-2, as indicated, for example, in FIGS. 1A and 1B. To specifically detect rat brain $\alpha_2\delta$-3 mRNA from rat atrial $\alpha_2\delta$-3 mRNA, a probe can be used which contains the nucleotide sequence that flanks and includes base pairs 1,381 to 1,398 of SEQ ID NO:5. To differentiate between rat brain $\alpha_2\delta$-3 full-length mRNA and $\alpha_2\delta$-3 variant mRNA, a probe can be used which contains portions of the nucleotide sequence contained only in the $\alpha_2\delta$-3 full-length mRNA SEQ. ID. NO:5 and not is SEQ. ID. NO:8, for example, nucleotide sequences between about base pair 2,449 and about base pair 2,874 of SEQ. ID. NO:5. Alternatively, a probe to specifically detect the $\alpha_2\delta$-3 variant mRNA from the $\alpha_2\delta$-3 full-length mRNA can be generated to include nucleotide sequence that flanks and includes base pairs 2,448 and 2,449 of SEQ. ID. NO:9, for example, nucleotide sequences from about base pair 2,442 to about 2,455 of SEQ ID NO:9. The mRNA's of the $\alpha_2\delta$-2 and $\alpha_2\delta$-3 subunits of the invention can also be distinguished from each other by length.

Nucleic acid probes can be prepared using routine methods, including automated oligonucleotide synthetic methods. For use of such probes, the biological sample to be analyzed may be treated, if desired, to extract the RNA contained therein. The resulting RNA from the sample may be subjected to gel electrophoresis or other size separation techniques; alternatively, the RNA sample may be dot blotted without size separation. The probes are usually labeled with a detectable label. Suitable labels, and methods for labeling probes are known in the art, and include, for example, radioactive labels incorporated by nick translation or kinasing, biotin, fluorescent probes, and chemiluminescent probes. The RNA extracted from the sample is then treated with the labeled probe under hybridization conditions of suitable stringencies.

In addition to detecting mRNA production, the probes of the invention, as described above, can be used to recover nucleotide sequences encoding $\alpha_2\delta$-2 and $\alpha_2\delta$-3 subunits from other animals. The probes may be used with respect to cDNA libraries or genomic libraries derived from other species, and are tested for hybridization under the high stringency conditions described above.

In one embodiment, the invention features methods for detecting expression of rat brain $\alpha_2\delta$-2 and/or $\alpha_2\delta$-3 subunits through detection of the $\alpha_2\delta$-2 and/or $\alpha_2\delta$-3 polypeptides in a biological sample. Polypeptide-based detection can be accomplished by use of an antibody (including antigen-binding antibody fragments) or a receptor (including ligand-binding receptor fragments) that specifically binds the target $\alpha_2\delta$-2 and/or $\alpha_2\delta$-3 polypeptides (e.g., an anti-rat brain $\alpha_2\delta$-2 polypeptide antibody and anti-rat brain $\alpha_2\delta$-3 polypeptide antibody). For example, the presence of target $\alpha_2\delta$-2 and/or $\alpha_2\delta$-3 polypeptides in a sample can be determined using a target $\alpha_2\delta$-2 and/or $\alpha_2\delta$-3-specific probe using various techniques known in the art including, but not limited to, quantitative immunoassays, such as, radioimmunoassay, immunofluorescent assay, enzyme immunoassay, chemiluminescent assay, ELISA, western blot assay, immunocytochemistry assay or immunohistochemistry assay.

For detection at the protein level, it is convenient to produce antibodies to $\alpha_2\delta$-2 and $\alpha_2\delta$-3 proteins of the invention. The antibodies are immunospecific to these proteins if they immunoreact detectably more strongly to the $\alpha_2\delta$-2 and $\alpha_2\delta$-3 subunits of the invention as compared to other proteins, including $\alpha_2\delta$-2 and $\alpha_2\delta$-3 proteins of the prior art. The antibodies may be polyclonal, monoclonal, single-chain recombinant, and the like. Methods for preparation of such antibodies, including antibodies designed to be compatible with individual species such as humanized antibodies are well known. It is also understood that the term "antibodies" includes immunospecific fragments thereof, such as $F_{ab}$, $F_{ab'}$, and the like. As mentioned above, single-chain $F_v$ antibodies also represent useful fragments. The rat brain $\alpha_2\delta$-2, $\alpha_2\delta$-3 full length and $\alpha_2\delta$-3 variant proteins can also be distinguished from each other by differences in molecular weight.

To differentially detect the rat brain $\alpha_2\delta$-2 and $\alpha_2\delta$-3 proteins of the invention from their rat atrial counterparts (and likely other $\alpha_2\delta$ proteins), antibodies specific to the polypeptide regions in which the $\alpha_2\delta$-2 and $\alpha_2\delta$-3 proteins of the invention differ from those known in the art can be produced. For example, to specifically detect rat brain $\alpha_2\delta$-2 protein, an antibody can be produced to the polypeptide region that flanks and includes amino acids 664–666, such as a polypeptide comprising the amino acid sequence from about 660 to about 670 of SEQ. ID. NO:3. To specifically detect rat brain $\alpha_2\delta$-3 protein from rat atrial $\alpha_2\delta$-3 protein, an antibody can be produced to the polypeptide region that flanks and includes amino acids 461 to 466, such as a polypeptide comprising the amino acid sequence from about 457 to about 470 of SEQ. ID. NO:6.

To differentiate between rat brain $\alpha_2\delta$-3 full-length protein (SEQ. ID. NO:6) and the $\alpha_2\delta$-3 variant (SEQ. ID. NO:9), antibodies can be produced directed to a portion of the full-length protein missing from the variant, for example from about amino acid 817 to about amino acid 958 of SEQ. ID. NO:6. Such an antibody would likely also distinguish between the rat atrial $\alpha_2\delta$-3 full-length protein (SEQ. ID. NO:4) and the rat brain $\alpha_2\delta$-3 variant (SEQ. ID. NO:9). In addition, or alternatively, to specifically detect the rat brain $\alpha_2\delta$-3 variant (SEQ. ID. NO:9), antibodies can be generated directed to a polypeptide spanning the portion missing relative to the full-length protein. For example, an antibody specific for a polypeptide that includes amino acids flanking amino acids 816 and 817 of SEQ. ID. NO:9, such as a polypeptide comprising the amino acid sequence from about 810 to about 824 of SEQ. ID. NO:9, would allow specific detection of the $\alpha_2\alpha$-3 variant polypeptide.

A combination of antibodies may also be used to identify and/or quantitate the $\alpha_2\delta$-3 variant from the full length $\alpha_2\delta$-3 polypeptide. In such a case, one antibody which recognizes the shared portion of the two polypeptides, i.e., a section of the N-terminal portion from amino acid 1 to about amino acid 817, and the other antibody which recognizes the portion of the full-length protein missing from the variant, for example from about amino acid 817 to about amino acid 958 of SEQ. ID. NO:6, can be used. Detection of differences in binding of the two antibodies could be used to distinguish rat brain $\alpha_2\delta$-3 full length from rat brain $\alpha_2\delta$-3 variant.

These antibodies can be used to detect the production of any calcium channel which includes the $\alpha_2\delta$ calcium ion channels on histological sections or tissue extracts. Expression and display on recombinant cells can also be detected using these antibodies. Standard methods for labeling and detecting the antibody complexes are employed.

Complexes formed comprising the $\alpha_2\delta$-2 or $\alpha_2\delta$-3 polypeptides of the invention and the anti-$\alpha_2\delta$-2 or $\alpha_2\delta$-3 subunit antibody are detected by any of a number of known techniques, depending on the format. The antibody in the immunoassays for detection of the $\alpha_2\delta$-2 and $\alpha_2\delta$-3 polypeptides of the invention may be provided on a support (e.g., solid or semi-solid); alternatively, the polypeptides in the sample can be immobilized on a support. Examples of supports that can be used are nitrocellulose (e.g., in membrane or microtiter well form), polyvinyl chloride (e.g., in sheets or microtiter wells), polystyrene latex (e.g., in beads or microtiter plates), polyvinylidene fluoride, diazotized paper, nylon membranes, activated beads, and Protein A beads. Bead-based supports are generally more useful for immobilization of the antibody in the assay.

In one embodiment, the biological sample contains cells (i.e., whole cells) and detection is by reacting the sample with labeled antibodies, performed in accordance with conventional methods. In general, antibodies that specifically bind a $\alpha_2\delta$-2 or $\alpha_2\delta$-3 polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g., fluorescein, rhodamine, Texas red, and others). The absence or presence of antibody binding can be determined by various methods, including, but not limited to, flow cytometry of dissociated cells, microscopy, radiography, and scintillation counting. Any suitable alternative methods of qualitative or quantitative detection of levels or amounts of differentially expressed polypeptide can be used, for example ELISA, Western blot, immunoprecipitation, radioimmunoassay, and the like.

The following examples are offered to illustrate but not to limit the invention.

EXAMPLE 1

Novel $\alpha_2\delta$-2 subunits of the invention were identified using RT-PCR of rat brain total RNA and screening of a rat brain cDNA library. Screening of the cDNA library followed standard methods and included infecting bacteria with recombinant lambda phage and immobilizing lambda DNA on to nylon filters (Hybond-N, Amersham Pharmacia biotech).

A rat $\alpha_2\delta$-2 cDNA probe of 313 bp (1,368–1,680) was amplified from rat brain total RNA using One-Step RT-PCR (Superscript, Invitrogen) with primers designed to conserved regions of the mouse and human $\alpha_2\delta$-2 genes as follows:

F1368, 5'-AGCCATCCGCATCAACACACAG- (SEQ ID NO:12)
3';

R1680, 5'-AGCAACACGTAGCCGTTCAGGTC- (SEQ ID NO:13)
3'.

The resulting probe was radiolabeled with $[\alpha^{32}P]$ dCTP using the Multi-Prime DNA labeling System (Amersham) and the free $\alpha^{32}P$ removed using a Centri Spin-20 column (Princeton Separations). Approximately 300,000 plaque forming units (pfus) were screened with the radiolabeled probe using moderate hybridization (55° C.) in Church and Gilbert's solution and moderate to high wash conditions (55° C., 0.2×SSC/0.1% SDS). Bacteriophage that hybridized to the rat $\alpha_2\delta$-2 radiolabeled probe were detected by exposing the membranes to autoradiography. Positive clones were purified by sequential rounds of screening and the phagemid cDNA (pBluescript SK+) isolated by in vivo excision using the ExAssist helper phage with SOLR Strain *E. coli* according to the manufacturer's instructions (Stratagene).

Ten positive clones were sequenced and found to contain cDNA fragments of the rat $\alpha_2\delta$-2 subunit (4.0 Kb >). Two clones were completely sequenced of which one clone, rat library clone 11-1-2, contained a sequence of 4,507 base pairs (bp). This clone was missing 487 bp of the 5' open reading frame (ORF). In order to obtain the 5' end of the rat $\alpha_2\delta$-2 cDNA, antisense primers were made to the rat $\alpha_2\delta$-2 sequence and sense primers were designed to consensus sequence of the human and mouse subunits.

Primer 591R: 5'-GCTCCTCGATGAAGTCCAGCCTTA-3' (SEQ ID NO:14), was used in the reverse transcriptase (RT) reaction of rat brain total RNA (60° C., 90 min). A 561 bp 5' fragment of the rat $\alpha_2\delta$-2 mRNA, including 24 base pairs of the 5' untranslated sequence, was amplified using PCR from the RT reaction using Hot Star Taq plus Q-solution (Qiagen) with a sense primer designed to the human and mouse 5' UTR sequence:

F-24: 5'-CGGCGCCGCATCTTGAATGGAAAC- (SEQ ID NO:15)
3', and an antisense primer to the rat $\alpha_2\delta$-2 library clone.

The $\alpha_2\delta$-2 PCR fragment was subsequently inserted into pGEM-T (Promega). In order to make a full-length rat $\alpha_2\delta$-2 cDNA, subunit primers were designed with the restriction enzyme sites, Hind III (F-5:5'-GCGAAGCTTGAAACATG-GCGGTGC-3' (SEQ ID NO:16)), which removes the first AUG, and BamH I (557R: 5'-TGGATCCCCTCTCCATATCCTCACTC-3' (SEQ ID NO:17)).

The PCR was done using Pfu (Stratagene) and the cDNA products were cloned into pGEM-T. The full-length rat $\alpha_2\delta$-2 sequence was constructed in the mammalian expression vector pBK-RSV (-lac p) using a three way ligation of the Hind III/BamH I 5' PCR fragment and the BamH I/Xba 1 region of the rat library clone 11-1-2.

The full-length rat brain $\alpha_2\delta$-2 cDNA clone has the nucleic acid SEQ. ID. NO:2: Full-length rat brain $\alpha_2\delta$-2 calcium channel subunit nucleotide sequence (SEQ. ID. NO:2)

```
   1 CGGCGCCGCA TCTTGAATGG AAACATGGCG GTGCCGGCTC GGACCTGCGG CGCTTCTTGG
  61 CCCGGCCCGG TGCGGACCGC TCGCCCCTGG CCCGGTCGCG GTCCCCGGCC CTGCCCTGAC
 121 CCCCGGGGCC CAGCGTCCGG GCCCGCACGC CCGCTCTTGC TACTGCTGCC GCCTCTGCTG
 181 CTTTTACCGC TGCTCACCGC CCCCGGCGCC TCTGCCTACA GCTTCCCCCA GCAGCACACG
 241 ATGCAGCACT GGGCCCGGCG CCTGGAGCAG GAGATTGACG GTGTGATGCG GATTTTTGGA
 301 GGCGTGCAGC AGCTCCGAGA GATCTACAAG GACAATCGGA ACCTGTTTGA TGTGCAGGAG
 361 AATGAACCAC AGAAACTAGT GGAGAAGGTG GCAGGGGACA TTGAGAGCCT GCTGGACAGA
 421 AAGGTCCAGG CCTTGAAGAG ACTGGCTGAC GCTGCAGAGA ATTTCCAGAA AGCCCACCGC
 481 TGGCAAGACA ACATCAAGGA GGAAGACATC ATGTACTATG ACGCCAAGGC TGACGCCGAG
 541 CTGGATGATC CTGAGAGTGA GGATATGGAG AGGGGATCCA AGACCAGCGC CTTAAGGCTG
 601 GACTTCATCG AGGAGCCAAA CTTCAAGAAC AAAGTCAACT ATTCATACAC GGCGGTGCAG
 661 ATCCCCACAG ATATCTACAA AGGCTCTACC GTCATCCTCA ATGAGCTTAA CTGGACGGAG
 721 GCCCTGGAGA ATGTCTTCAT TGAGAACCGT AGGCAAGACC CTACACTGTT GTGGCAAGTC
 781 TTCGGCAGTG CCACGGGAGT CACCCGCTAT TACCCAGCCA CACCGTGGCG AGCCCCCAAG
 841 AAGATTGACC TGTACGATGT CAGAAGACGA CCCTGGTATA TACAGGGGGC CTCATCACCC
 901 AAGGACATGG TCATCATTGT GGATGTGAGT GGCAGTGTGA GCGGCCTGAC GCTGAAGCTG
 961 ATGAAGACGT CTGTCTGTGA GATGCTAGAC ACACTCTCCG ATGATGACTA TGTGAATGTG
1021 GCCTCATTCA ACGAGAAGGC GCAGCCTGTG TCTTGCTTCA CACACCTGGT GCAGGCCAAT
1081 GTGCGGAACA AGAAGGTGTT CAAGGAAGCT GTGCAGGGCA TGGTGGCCAA GGGCACCACA
1141 GGCTACAAGG CTGGCTTTGA GTATGCCTTT GACCAGCTAC AGAATTCCAA CATCACCCGT
1201 GCTAACTGCA ATAAGATGAT CATGATGTTC ACGGACGGGG GAGAGGATCG CGTGCAGGAC
1261 GTCTTTGAAA AGTATAATTG GCCCAATCGG ACGGTACGCG TCTTCACGTT CTCCGTAGGA
1321 CAGCATAACT ATGATGTCAC ACCCCTGCAG TGGATGGCTT GTACTAACAA AGGTTACTAT
1381 TTTGAGATCC CTTCCATCGG AGCCATCCGC ATCAACACAC AGGAATACCT GGATGTGCTG
1441 GGTAGGCCCA TGGTCCTGGC AGGCAAGGAC GCCAAGCAAG TGCAATGGAC AAACGTGTAT
1501 GAAGATGCGC TGGGGCTGGG GTTGGTGGTA ACAGGGACTC TCCCTGTTTT CAACCTGACA
1561 CAGGATGGCC CTGGGGAAAA GAAGAACCAG CTAATCCTGG GTGTCATGGG CATAGATGTG
1621 GCCCTGAATG ACATCAAAAG GCTGACTCCC AACTACACAC TTGGCGCCAA TGGCTACGTG
1681 TTCGCCATCG ACCTGAATGG CTATGTGTTG CTACATCCCA ATCTCAAGCC CCAGACTACC
1741 AACTTCCGGG AGCCTGTGAC CTTGGACTTC CTGGATGCAG AGCTGGAAGA TGAGAACAAG
1801 GAGGAGATCC GTCGTAGTAT GATTGACGAA GACAAAGGCC ACAAGCAGAT CAGAACCTTG
1861 GTCAAATCCC TGGATGAGAG GTACATAGAT GAAGTGATTC GGAACTACAC CTGGGTGCCT
1921 ATAAGGAGTA CCAACTACAG CCTGGGGCTG GTGCTCCCAC CCTACAGCAC CTACTACCTC
```

-continued

```
1981 CAAGCCAACC TCAGCGACCA GATCCTGCAG GTCAAGTATT TTGAGTTCCT GCTCCCCAGC

2041 AGCTTTGAGT CTGAAGGACA TGTTTTCATT GCTCCCAGAG AGTATTGCAA GGATTTGAAT

2101 GCCTCAGACA ACAACACCGA GTTCCTGAAA AACTTCATTG AGCTCATGGA GAAAGTGACT

2161 CCGGACTCCA AGCAGTGCAA TAACTTCCTT CTGCATAACT TGATTTTGGA CACGGGCATT

2221 ACGCAGCAGT TAGTGGAACG CGTCTGGCGG GACCAAGATC TCAACACGTA CAGCCTGCTA

2281 GCTGTATTTG CTGCCACTGA CGGTGCAGTC ACACGTGTCT TCCCGAACAA GGCAGCTGAA

2341 GACTGGACAG AAAACCCTGA ACCCTTCAAT GCCAGCTTCT ACCGCCGCAG CCTGGATAAC

2401 CGTGGTTATA TCTTCAAGCC CCCGCACCAG GACTCCCTGT TAAGGCCACT GGAGCTGGAG

2461 AATGACACAG TAGGCGTCCT CGTCAGCACA GCTGTAGAGC TCAGTCTGGG TCGCCGCACA

2521 CTGAGGCCAG CAGTGGTGGG TGTCAAACTG GACCTAGAGG CTTGGGCTGA AAAGTTCAAG

2581 GTGCTTGCCA GCAACCGTAC CCATCAGGAC CAACCTCAGA AGCAGTGCGG CCCCAGCAGC

2641 CACTGTGAGA TGGACTGCGA GGTAAACAAC GAGGACCTAC TCTGTGTCCT CATTGATGAC

2701 GGGGGATTCC TGGTGCTGTC AAACCAGAAC CACCAGTGGG ACCAGGTTGG CAGATTCTTC

2761 AGTGAGGTGG ATGCCAACCT GATGCTGGCA CTGTACAATA ACTCCTTCTA CACCAGAAAG

2821 GAGTCCTATG ACTATCAGGC AGCTTGTGCC CCTCAGCCTC CTGGCAACCT GGGTGCTGCA

2881 CCCAGGGGTG TCTTTGTGCC CACCATTGCA GATTTCCTTA ACTTGGCCTG GTGGACCTCT

2941 GCTGCCGCCT GGTCCTTATT CCAGCAACTA CTTTATGGTC TCATCTATCA CAGCTGGTTC

3001 CAGGCAGACC CGGCAGAAGC CGAGGGCAGC CCCGAGACGC GCGAGAGCAG CTGCGTCATG

3061 AAACAAACCC AGTACTACTT CGGCTCGGTG AACGCGTCCT ATAACGCCAT CATCGACTGC

3121 GGAAACTGCA GCAGGCTGTT CCACGCGCAG AGACTGACCA ACACCAACCT TCTGTTCGTG

3181 GTGGCGGAGA AGCCGCTGTG CAGCCAGTGC GAGGTCGGCC GGCTGCTACA AAAGGAGACA

3241 CACTGCCCAG CGGACGGCCC GGAGCAGTGT GAGCTGGTGC AGAGACCGCG ATACCGAAGA

3301 GGCCCGCACA TCTGTTTTGA CTACAATGCG ACGGAAGATA CCTCAGACTG TGGCCGCGGC

3361 ACGTCCTTCC CTCCGTCGCT GGGCGTCTTG GTTTCCCTGC AGCTGTTGCT CCTCCTAGGC

3421 CTGCCACCTC GGCCGCAGCC TCAAATCCAT TCCTTCGCTG CCTCTCGCCG CCTCTGAACT

3481 ACCCACACAC ACACATCATA GCCCCCACCC CCACCCCGCC TTGGCCTCCT AGCCTTTTCG

3541 CTCACCCTCC CATGCCACAT TCCCCAATCT AGATCCTTGG CCAGTCTCTC CTGAAGGAAC

3601 TGGGCCCCTT CCCCGGAGCC TGTGCCTTGG GGCAGGGGAG CCAAAGTAAG GTGCCATGGT

3661 GTTTGGCACT CAAGATTTAT CTCACCCTTG AACTGTCCAA GTGCCCACAG TCCCTGGACT

3721 CACCCCTGTG GTTGGGACAG GAGGCCACTA GTACCGATGC CAAACCAGGC CTCCACCAAC

3781 CCACCTGCCT GGAGATTTTC TCTATGTAGG CAACCCTGCC ACTGCTGGGC GCCTCTAACT

3841 GGCCCTTTGC CCCACCCAGG CCCAAACTTA CCTTCTCTGG GGAAAAAACT AGGAGAGATG

3901 GNTAGTGGTG AGAGAGATTC TGGGGGCACC CCTTCCCCAT AGCCTCGGGC CGTTCCAGGC

3961 TACACCACAA ACCCACACCT CGGCTTGCAG GTATCAGGAC AGCCTCACGA TGACATCAGC

4021 TTAGGCACAC CCCACAGACA CCTGGACCTC AGAGAGCAGA AACTGGACTC TCACTAGACA

4081 TGCCCGAGAG GGAACACACA AACAGACACA CACCATGGGG GACCCACAAA GCCTTACACA

4141 GGGCGAGAGG TCAGTGAAGG GGCTGACCTG TGTGTTCCTT CTCCGCTCAC CTCTGCCTCC

4201 ACTCTGAGAT GCAGCCTGGC AGGCCCTCCC ATCTCTAGAA CTGAATGTCA GACCGTGCCA

4261 AATGCTAGGG GAAGGCCTCT GTTTCGCCCC TAGCCACCAG TGTCCCCAAA TGCCCCTCAC

4321 CCTGCCAGGT GCTCATTGTA ACCATTGCTC ACTAGTGTCA GGCCCCTAGT AGGACCACAT
```

```
-continued
4381 GTCACTGCCT GAACCCCTTT GGCAGAAGAA CCCCGCCAGA CATTGTACTT TGCCTTAGCA

4441 GGGGTGACTT GGTCTCTCCT GGCTGGGCCA TCCCATCCCC AATCTGGTTC TTACATACTC

4501 AGGCCTAATT CCCTCTTCAC ACACACACAC ACACACACAC ACACACACAC ACACACACAG

4561 TCCCTGCCCC TAGGAGGCCA TATTGCCCCT CCCTTGCTGA ACACACACTT GCACCAAGCA

4621 CATGTGTAGT CAACCATACT GCACACACAG AGGCTGGGCC TGGGACACAT CTCTTCACAC

4681 CATTCATTCT GTCATTTCTC CCAAAGGCAT CGTAACCTGG GGGCCAGGCG GGGACTGAGG

4741 GCAGGGTGGG GGGGTGTGTG GCCATGAGGC TCAGATGGAC TGGGAGGAGG GTGGGAGGGT

4801 GGTACATTAA TTAATGGCTC CGTTAATTAA TGTCATGTTG CGTGTTGCTT TCTCAGTGTG

4861 TGTATGGTCC ATGCCCAATG CTGGTGGCAG GGTGGGTGTC CATGATGTGT GCCCAGCCTG

4921 GATGTCAGCT GTGTCCTGTG GGGGCGTGTG TGTAACTGTA GTGTAGTCAG GTGCTCAACG

4981 GAGAATACAA ACG
``` and the deduced amino acid sequence of rat brain $\alpha_2\delta$-2 cDNA is SEQ. ID. NO:3.

Translated rat brain $\alpha_2\delta$-2 amino acid sequence (SEQ. ID. NO:3):

```
   1 MAVPARTCGA SWPGPVRTAR PWPGRGPRPC PDPRGPASGP ARPLLLLLPP

51 LLLLPLLTAP GASAYSFPQQ HTMQHWARRL EQEIDGVMRI FGGVQQLREI

101 YKDNRNLFDV QENEPQKLVE KVAGDIESLL DRKVQALKRL ADAAENFQKA

151 HRWQDNIKEE DIMYYDAKAD AELDDPESED MERGSKTSAL RLDFIEEPNF

201 KNKVNYSYTA VQIPTDIYKG STVILNELNW TEALENVFIE NRRQDPTLLW

251 QVFGSATGVT RYYPATPWRA PKKIDLYDVR RRPWYIQGAS SPKDMVIIVD

301 VSGSVSGLTL KLMKTSVCEM LDTLSDDDYV NVASFNEKAQ PVSCFTHLVQ

351 ANVRNKKVFK EAVQGMVAKG TTGYKAGFEY AFDQLQNSNI TRANCNKMIM

401 MFTDGGEDRV QDVFEKYNWP NRTVRVFTFS VGQHNYDVTP LQWMACTNKG

451 YYFEIPSIGA IRINTQEYLD VLGRPMVLAG KDAKVQWTN  VYEDALGLGL

501 VVTGTLPVFN LTQDGPGEKK NQLILGVMGI DVALNDIKRL TPNYTLGANG

551 YVFAIDLNGY VLLHPNLKPQ TTNFREPVTL DFLDAELEDE NKEEIRRSMI

601 DEDKGHKQIR TLVKSLDERY IDEVIRNYTW VPIRSTNYSL GLVLPPYSTY

651 YLQANLSDQI LQVKYFEFLL PSSFESEGHV FIAPREYCKD LNASDNNTEF

701 LKNFIELMEK VTPDSKQCNN FLLHNLILDT GITQQLVERV WRDQDLNTYS

751 LLAVFAATDG AVTRVFPNKA AEDWTENPEP FNASFYRRSL DNRGYIFKPP

801 HQDSLLRPLE LENDTVGVLV STAVELSLGR RTLRPAVVGV KLDLEAWAEK

851 FKVLASNRTH QDQPQKQCGP SSHCEMDCEV NNEDLLCVLI DDGGFLVLSN

901 QNHQWDQVGR FFSEVDANLM LALYNNSFYT RKESYDYQAA CAPQPPGNLG

951 AAPRGVFVPT IADFLNLAWW TSAAAWSLFQ QLLYGLIYHS WFQADPAEAE

1001 GSPETRESSC VMKQTQYYFG SVNASYNAII DCGNCSRLFH AQRLTNTNLL

1051 FVVAEKPLCS QCEVGRLLQK ETHCPADGPE QCELVQRPRY RRGPHICFDY

1101 NATEDTSDCG RGTSFPPSLG VLVSLQLLLL LGLPPRPQPQ IHSFAASRRL

1151 *
```

The rat brain α₂δ-2 variant cDNA clone was also identified and has SEQ ID NO:10: Rat brain α₂δ-2 variant calcium channel subunit nucleotide sequence (SEQ. ID. NO:10)

```
   1 ATGGCGGTGC CGGCTCGGAC CTGCGGCGCT TCTTGGCCCG GCCCGGTGCG GACCGCTCGC
     CCCTGGCCCG GTCGCGGTCC

81 CCGGCCCTGC CCTGACCCCC GGGGCCCAGC GTCCGGGCCC GCACGCCCGC TCTTGCTACT
     GCTGCCGCCT CTGCTGCTTT

161 TACCGCTGCT CACCGCCCCC GGCGCCTCTG CCTACAGCTT CCCCCAGCAG CACACGATGC
     AGCACTGGGC CCGGCGCCTG

241 GAGCAGGAGA TTGACGGTGT GATGCGGATT TTTGGAGGCG TGCAGCAGCT CCGAGAGATC
     TACAAGGACA ATCGGAACCT

321 GTTTGATGTG CAGGAGAATG AACCACAGAA ACTAGTGGAG AAGGTGGCAG GGGACATTGA
     GAGCCTGCTG GACAGAAAGG

401 TCCAGGCCTT GAAGAGACTG GCTGACGCTG CAGAGAATTT CCAGAAAGCC CACCGCTGGC
     AAGACAACAT CAAGGAGGAA

481 GACATCATGT ACTATGACGC CAAGGCTGAC GCCGAGCTGG ATGATCCTGA GAGTGAGGAT
     ATGGAGAGGG GATCCAAGAC

561 CAGCGCCTTA AGGCTGGACT TCATCGAGGA GCCAAACTTC AAGAACAAAG TCAACTATTC
     ATACACGGCG GTGCAGATCC

641 CCACAGATAT CTACAAAGGC TCTACCGTCA TCCTCAATGA GCTTAACTGG ACGGAGGCCC
     TGGAGAATGT CTTCATTGAG

721 AACCGTAGGC AAGACCCTAC ACTGTTGTGG CAAGTCTTCG GCAGTGCCAC GGGAGTCACC
     CGCTATTACC CAGCCACACC

801 GTGGCGAGCC CCCAAGAAGA TTGACCTGTA CGATGTCAGA AGACGACCCT GGTATATACA
     GGGGGCCTCA TCACCCAAGG

881 ACATGGTCAT CATTGTGGAT GTGAGTGGCA GTGTGAGCGG CCTGACGCTG AAGCTGATGA
     AGACGTCTGT CTGTGAGATG

961 CTAGACACAC TCTCCGATGA TGACTATGTG AATGTGGCCT CATTCAACGA GAAGGCGCAG
     CCTGTGTCTT GCTTCACACA

1041 CCTGGTGCAG GCCAATGTGC GGAACAAGAA GGTGTTCAAG GAAGCTGTGC AGGGCATGGT
     GGCCAAGGGC ACCACAGGCT

1121 ACAAGGCTGG CTTTGAGTAT GCCTTTGACC AGCTACAGAA TTCCAACATC ACCCGTGCTA
     ACTGCAATAA GATGATCATG

1201 ATGTTCACGG ACGGGGGAGA GGATCGCGTG CAGGACGTCT TGAAAAGTA TAATTGGCCC
     AATCGGACGG TACGCGTCTT

1281 CACGTTCTCC GTAGGACAGC ATAACTATGA TGTCACACCC CTGCAGTGGA TGGCTTGTAC
     TAACAAAGGT TACTATTTTG

1361 AGATCCCTTC CATCGGAGCC ATCCGCATCA ACACACAGGA ATACCTGGAT GTGCTGGGTA
     GGCCCATGGT CCTGGCAGGC

1441 AAGGACGCCA AGCAAGTGCA ATGGACAAAC GTGTATGAAG ATGCGCTGGG GCTGGGGTTG
     GTGGTAACAG GGACTCTCCC

1521 TGTTTTCAAC CTGACACAGG ATGGCCCTGG GGAAAAGAAG AACCAGCTAA TCCTGGGTGT
     CATGGGCATA GATGTGGCCC

1601 TGAATGACAT CAAAAGGCTG ACTCCCAACT ACACACTTGG CGCCAATGGC TACGTGTTCG
     CCATCGACCT GAATGGCTAT

1681 GTGTTGCTAC ATCCCAATCT CAAGCCCCAG ACTACCAACT TCCGGGAGCC TGTGACCTTG
     GACTTCCTGG ATGCAGAGCT

1761 GGAAGATGAG AACAAGGAGG AGATCCGTCG TAGTATGATT GACGAAGACA AAGGCCACAA
     GCAGATCAGA ACCTTGGTCA

1841 AATCCCTGGA TGAGAGGTAC ATAGATGAAG TGATTCGGAA CTACACCTGG GTGCCTATAA
     GGAGTACCAA CTACAGCCTG

1921 GGGCTGGTGC TCCCACCCTA CAGCACCTAC TACCTCCAAG CCAACCTCAG CGACCAGATC
     CTGCAGGTCA AGTTGCCAAT
```

-continued

```
2001 CAGCAAACTG AAGGATTTTG AGTTCCTGCT CCCCAGCAGC TTTGAGTCTG AAGGACATGT
     TTTCATTGCT CCCAGAGAGT

2081 ATTGCAAGGA TTTGAATGCC TCAGACAACA ACACCGAGTT CCTGAAAAAC TTCATTGAGC
     TCATGGAGAA AGTGACTCCG

2161 GACTCCAAGC AGTGCAATAA CTTCCTTCTG CATAACTTGA TTTTGGACAC GGGCATTACG
     CAGCAGTTAG TGGAACGCGT

2241 CTGGCGGGAC CAAGATCTCA ACACGTACAG CCTGCTAGCT GTATTTGCTG CCACTGACGG
     TGCAGTCACA CGTGTCTTCC

2321 CGAACAAGGC AGCTGAAGAC TGGACAGAAA ACCCTGAACC CTTCAATGCC AGCTTCTACC
     GCCGCAGCCT GGATAACCGT

2401 GGTTATATCT TCAAGCCCCC GCACCAGGAC TCCCTGTTAA GGCCACTGGA GCTGGAGAAT
     GACACAGTAG GCGTCCTCGT

2481 CAGCACAGCT GTAGAGCTCA GTCTGGGTCG CCGCACACTG AGGCCAGCAG TGGTGGGTGT
     CAAACTGGAC CTAGAGGCTT

2561 GGGCTGAAAA GTTCAAGGTG CTTGCCAGCA ACCGTACCCA TCAGGACCAA CCTCAGAAGC
     AGTGCGGCCC CAGCAGCCAC

2641 TGTGAGATGG ACTGCGAGGT AAACAACGAG GACCTACTCT GTGTCCTCAT TGATGACGGG
     GGATTCCTGG TGCTGTCAAA

2721 CCAGAACCAC CAGTGGGACC AGGTTGGCAG ATTCTTCAGT GAGGTGGATG CCAACCTGAT
     GCTGGCACTG TACAATAACT

2801 CCTTCTACAC CAGAAAGGAG TCCTATGACT ATCAGGCAGC TTGTGCCCCT CAGCCTCCTG
     GCAACCTGGG TGCTGCACCC

2881 AGGGGTGTCT TTGTGCCCAC CATTGCAGAT TTCCTTAACT TGGCCTGGTG GACCTCTGCT
     GCCGCCTGGT CCTTATTCCA

2961 GCAACTACTT TATGGTCTCA TCTATCACAG CTGGTTCCAG GCAGACCCGG CAGAAGCCGA
     GGGCAGCCCC GAGACGCGCG

3041 AGAGCAGCTG CGTCATGAAA CAAACCCAGT ACTACTTCGG CTCGGTGAAC GCGTCCTATA
     ACGCCATCAT CGACTGCGGA

3121 AACTGCAGCA GGCTGTTCCA CGCGCAGAGA CTGACCAACA CCAACCTTCT GTTCGTGGTG
     GCGGAGAAGC CGCTGTGCAG

3201 CCAGTGCGAG GTCGGCCGGC TGCTACAAAA GGAGACACAC TGCCCAGCGG ACGGCCCGGA
     GCAGTGTGAG CTGGTGCAGA

3281 GACCGCGATA CCGAAGAGGC CCGCACATCT GTTTTGACTA CAATGCGACG GAAGATACCT
     CAGACTGTGG CCGCGGCACG

3361 TCCTTCCCTC CGTCGCTGGG CGTCTTGGTT TCCCTGCAGC TGTTGCTCCT CCTAGGCCTG
     CCACCTCGGC CGCAGCCTCA

3441 AATCCATTCC TTCGCTGCCT CTCGCCGCCT CTGA
``` and the deduced amino acid sequence of rat brain $\alpha_2\delta$-2 variant is SEQ ID NO:11.

Translated rat brain $\alpha_2\delta$-2 variant amino acid (SEQ ID NO:11):

```
  1 MAVPARTCGA SWPGPVRTAR PWPGRGPRPC PDPRGPASGP ARPLLLLLPP LLLLPLLTAP
    GASAYSFPQQ HTMQHWARRL

81 EQEIDGVMRI FGGVQQLREI YKDNRNLFDV QENEPQKLVE KVAGDIESLL DRKVQALKRL
    ADAAENFQKA HRWQDNIKEE

161 DIMYYDAKAD AELDDPESED MERGSKTSAL RLDFIEEPNF KNKVNYSYTA VQIPTDIYKG
    STVILNELNW TEALENVFIE

241 NRRQDPTLLW QVFGSATGVT RYYPATPWRA PKKIDLYDVR RRPWYIQGAS SPKDMVIIVD
    VSGSVSGLTL KLMKTSVCEM

321 LDTLSDDDYV NVASFNEKAQ PVSCFTHLVQ ANVRNKKVFK EAVQGMVAKG TTGYKAGFEY
    AFDQLQNSNI TRANCNKMIM
```

```
-continued
 401 MFTDGGEDRV QDVFEKYNWP NRTVRVFTFS VGQHNYDVTP LQWMACTNKG YYFEIPSIGA
     IRINTQEYLD VLGRPMVLAG 481 KDAKQVQWTN VYEDALGLGL VVTGTLPVFN LTQDGPGEKK NQLILGVMGI DVALNDIKRL
     TPNYTLGANG YVFAIDLNGY 561 VLLHPNLKPQ TTNFREPVTL DFLDAELEDE NKEEIRRSMI DEDKGHKQIR TLVKSLDERY
     IDEVIRNYTW VPIRSTNYSL 641 GLVLPPYSTY YLQANLSDQI LQVKLPISKL KDFEFLLPSS FESEGHVFIA PREYCKDLNA
     SDNNTEFLKN FIELMEKVTP 721 DSKQCNNFLL HNLILDTGIT QQLVERVWRD QDLNTYSLLA VFAATDGAVT RVFPNKAAED
     WTENPEPFNA SFYRRSLDNR 801 GYIFKPPHQD SLLRPLELEN DTVGVLVSTA VELSLGRRTL RPAVVGVKLD LEAWAEKFKV
     LASNRTHQDQ PQKQCGPSSH 881 CEMDCEVNNE DLLCVLIDDG GFLVLSNQNH QWDQVGRFFS EVDANLMLAL YNNSFYTRKE
     SYDYQAACAP QPPGNLGAAP 961 RGVFVPTIAD FLNLAWWTSA AAWSLFQQLL YGLIYHSWFQ ADPAEAEGSP ETRESSCVMK
     QTQYYFGSVN ASYNAIIDCG 1041 NCSRLFHAQR LTNTNLLFVV AEKPLCSQCE VGRLLQKETH CPADGPEQCE LVQRPRYRRG
     PHICFDYNAT EDTSDCGRGT

1121 SFPPSLGVLV SLQLLLLLGL PPRPQPQIHS FAASRRL*
```

EXAMPLE 2

Heterologous Expression of Rat $\alpha_2\delta$-2 Calcium Channel Subunits in Cells A. Transient Transfection in Mammalian Cells Human embryonic kidney cells, HEK 293 (ATCC# CRL 1573) or HEK 293 tsA 201, were grown in standard DMEM medium supplemented with 4 mM glutamine and 10% fetal bovine serum. The rat $\alpha_2\delta$-2 construct was transfected into HEK 293 or HEK 293 tsA 201 cells with equimolar concentration of the subunits $\alpha_{1B}$ (N-type calcium channel) and $\beta_{1b}$, using lipofectamine (Gibco/Invitrogen) according to the manufacturer's instructions. pEGFP was included in the transfected cDNA at 3–5 times less the molar concentration to detect transfected cells and to determine the efficiency of transfection. Transfected cells were incubated at 37° C., 5% $CO_2$, for 6–24 hours and then placed at 29° C., 5% $CO_2$.

After an incubation period of 24 to 72 hours, the culture medium was removed and replaced with an external recording solution containing (in mM) 5 $BaCl$, 129 CsCl, 1 $MgCl_2$, 10 HEPES, 10 glucose, pH 7.4 with CsOH. Whole-cell patch clamp recordings were made with an Axopatch 200B amplifier (Axon Instruments, USA). Recording electrodes with typical resistances of 4–8 MΩ were backfilled with (in mM) 108 caesium-methansulfonate, 2 $MgCl_2$, 10 HEPES, 11 EGTA, 2 ATP, pH 7.2 with some CsOH. To create command potentials and acquire data, Clampex 8.2 software (Axon Instruments, USA) and a Digidata 1322A A/D converter interface (Axon Instruments, USA) were used. Currents were elicited at test potential of +20 mV (50 ms duration) from a holding potential of −80 mV. Leak and capacitance currents were subtracted on-line with a standard P/4 protocol. Evoked currents were filtered by a low-pass Bessel filter set at 1 kHz. Signals were acquired at 2.02 kHz and analyzed offline using pClamp 8.2 (Axon Instruments, USA) and Origin (OriginLab Corporation, USA) software. The effects of coexpressing the rat $\alpha_2\delta$-2 auxiliary subunit of Example 1 with the rat $\alpha_{1B}+\beta_{1b}$ calcium channel subunits were tested by comparing average current density ($I_{peak}$/cell capacitance) with and without $\alpha_2\delta$-2.

Mean current density was recorded for 4 cells transfected with rat $\alpha_{1B}+\beta_{1b}$ only and for 7 cells that were also cotransfected with rat brain $\alpha_2\delta$-2 subunit. The rat $\alpha_{1B}+\beta_{1b}$ current density was increased by ~4 fold from −7.2±2.3 pA/pF to −30.0±4.1 pA/pF when coexpressed with the rat brain $\alpha_2\delta$-2 subunit. P=0.01, Student's unpaired t-test. Values are the mean±S.E.M (FIG. 4).

B. Transient Transfection in Xenopus Oocytes

Stage V and VI Xenopus oocytes are prepared as described by Dascal, et al., Science (1986) 231:1147–1150. After enzymatic dissociation with collagenase, oocyte nuclei are microinjected with the rat $\alpha_2\delta$-2 subunit cDNA expression vector construct (approximately 10 ng DNA per nucleus) using a Drummond nanoject apparatus, alone, or in combination with other rat, human or other mammalian or animal calcium channel subunit cDNA's, such as the $\alpha_1$ and $\beta_{1b}$ subunit cDNA. After incubation from 48 to 96 hours macroscopic currents are recorded using a standard two microelectrode voltage-clamp (Axoclamp 2A, Axon Instruments, Burlingame, Calif.) in a bathing medium containing (in mM): 40 $Ba(OH)_2$, 25 TEA-OH, 25 NaOH, 2 CsOH, 5 HEPES (pH titrated to 7.3 with methan-sulfonic acid). Pipettes of typical resistance ranging from 0.5 to 1.5 mΩ are filled with 2.8M CsCl, 0.2M CsOH, 10 mM HEPES, 10 mM BAPTA free acid. Endogenous Ca (and Ba)—activated Cl currents are suppressed by systematically injecting 10–30 nl of a solution containing 100 mM BAPTA-free acid, 10 mM HEPES (pH titrated to 7.2 with CsOH) using a third pipette connected to a pneumatic injector. Leak currents and capacitive transients are subtracted using a standard P/5 procedure.

EXAMPLE 3

Construction of Stable Cell Lines Expressing Rat $\alpha_2\delta$-2 Calcium Channels Mammalian cell lines stably expressing the rat brain $\alpha_2\delta$-2 calcium channel were made by transfecting an expression vector containing the $\alpha_2\delta$-2 calcium channel cDNA plus the rat β1b cDNA into HEK 293F cells, and selecting for cells resistant to Zeocin. Briefly, the full-length rat $\alpha_2\delta$-2 subunit cDNA (clone 27) was excised from the pBK-RSV vector by digestion with Hind III followed by treatment with the Klenow fragment of DNA polymerase I to generate a blunt end and subsequent digestion with Kpn I. The mammalian expression vector pBud CE 4 rat β1b clone 3 was digested with Not I followed by Klenow treatment and digestion with Kpn I. The rat $\alpha_2\delta$-2 fragment was ligated (blunt/sticky) into pBud CE4 rat β1b to give a final construct pBud rat $\alpha_2\delta$-2/rat β1b clone 3. Prior to making stable cell lines expressing the two subunits, the expression and activity of the subunits were tested by transient transfection and patch clamp analysis (see protocol Example 2). The pBud rat $\alpha_2\delta$-2/rat β1b construct was linearized with Pvu I and transfected into HEK 293F cells using lipofectamine. The transfected cells are incubated for 16 hours at 37° C., 5% $CO_2$, then placed in nonselective medium for an additional 24 hours. The cells were trypsinized and plated at low density in selective medium containing Zeocin at 250 μg/ml. After 14–16 days in selective medium, cells that were resistant to Zeocin grew as visible colonies which were harvested by the pipet technique. Cell colonies were expanded to make frozen stocks of cells and to determine the level of rat $\alpha_2\delta$-2 subunit expression. Rat $\alpha_2\delta$-2 subunit expression levels for the cell lines were determined by Northern blotting and reverse-transcriptase PCR. Detection of functional calcium channels containing the rat $\alpha_2\delta$-2 subunit in stably transfected cells is examined electrophysiologically, such as by whole cell patch clamp or single channel analysis (see above). Other means of detecting functional calcium channels include the use of radiolabeled $^{45}$Ca uptake, or fluorescence spectroscopy using calcium sensitive dyes such as FURA-2.

EXAMPLE 4

Novel $\alpha_2\delta$-3 subunits of the invention were identified using RT-PCR of rat brain total RNA and by screening a rat brain cDNA library. Screening of the cDNA library followed standard methods and included infecting bacteria with recombinant lambda phage and immobilizing lambda DNA onto nylon filters (Hybond-N, Amersham Pharmacia Biotech).

A rat $\alpha_2\delta$-3 cDNA probe of 470 bp (1789–2258) was amplified from rat brain total RNA using One-Step RT-PCR (Superscript, Invitrogen) with primers designed to a conserved region of the mouse and human $\alpha_2\delta$-3 genes as follows:

```
1789F  5'-GTGTCCTTGGCAGATGAATGGTCCTA  (SEQ ID NO:18)
       C-3';

2258R  5'-GATGTACTTGCTGTCACCACATTGC  (SEQ ID NO:19)
       T-3'.
```

The resulting rat $\alpha_2\delta$-3 PCR product was ligated into pGEM-T easy (Promega) (clone 1) and sequenced. The rat $\alpha_2\delta$-3 cDNA fragment was excised from the pGEM vector with Not I and radiolabeled with [$\alpha^{32}$P] dCTP using the Multi-Prime DNA Labeling System (Amersham). Free $\alpha^{32}$P dCTP was removed by passage through a Centri Spin-20 column (Princeton Separations). Approximately 300,000 plaque forming units (pfus) were screened with the radiolabeled probe using moderate hybridization (55° C.) in Church and Gilbert's solution and a final high stringency wash condition of 0.2×SSC/0.1% SDS (60° C., 30 min). Bacteriophage that hybridized to the rat $\alpha_2\delta$-3 radiolabeled probe were purified by sequential rounds of screening and the phagemid cDNA (pBluescript SK+) isolated by in vivo excision using the ExAssist helper phage with SOLAR Strain E. coli according to the manufacturer's instructions (Stratagene).

Four positive clones were purified by excision, sequenced and found to contain cDNA fragments of the rat $\alpha_2\delta$-3 mRNA. Two different size cDNA fragments were obtained, two of 1,625 bp and two of 1,407 bp, of which one clone from each size was completely sequenced. Both clones were missing approximately 1,500 bp of 5' ORF. Clone 7-2-1-4 (1,625 bp) had more 5' region, but truncated approximately 70 bp before the stop codon. Clone 7-3-1-1 (1,407 bp) starts at 1,766 bp and includes the stop signal and a portion of the 3' UTR, but is missing approximately 426 bp (2,451–2,877) of coding sequence in the 3' region of rat $\alpha_2\delta$-3 mRNA. Translation of clone 7-3-1-1 into the protein sequence revealed that this clone is a splice variant with a deletion of 142 amino acids (FIG. 3). In order to obtain the 5' region of the rat $\alpha_2\delta$-3 mRNA, an antisense primer:

```
2021R  5'-ATCGCTTCCAGTTGAGAGAGATGG-  (SEQ ID NO:20)
       3'
``` was made to the rat brain $\alpha_2\delta$-3 cDNA and a sense primer to the rat atrial $\alpha_2\delta$-3 cDNA sequence (AF486278, SEQ. ID. NO:4):

```
1F  5-'ATGGCCGGGCCGGGCTCGCTGTGCT-3'  (SEQ ID NO:21)
``` and used in One-Step RT-PCR to amplify a 2,018 bp cDNA fragment.

The PCR products were cloned into pGEM-T easy and two clones were completely sequenced and identified to be rat $\alpha_2\delta$-3. These clones extended from the start codon (ATG) to position 2,018 bp. A full-length rat $\alpha_2\delta$-3 cDNA was constructed using the PCR 5' fragment (clone 1) and the two clones 7-2-1-4 and 7-3-1-1. Clone 1 was digested with Not I/Sac I and the lambda clone 7-2-1-4 digested with Sac I/Kpn I. These two cDNA fragments were three way ligated into pBK/RSV at the Not I/Kpn I sites. The full-length rat $\alpha_2\delta$-3 cDNA was constructed in the mammalian expression vector pBud CE4 (Not I/Kpn I) using a three way ligation of a Not I/Ban I digested fragment of pBK/RSV clone 1/7-2-1-4 (Ban I cuts at position 3,087 in the cDNA) and a Ban I/Kpn I digested fragment of clone 7-3-1-1.

The full-length rat brain $\alpha_2\delta$-3 cDNA clone (clone 1/7-2-1-4) has SEQ. ID. NO:5: Full-length rat brain $\alpha_2\delta$-3 calcium channel subunit nucleotide sequence (SEQ. ID. NO:5)

```
  1 ATG GCC GGG CCG GGC TCG CTG TGC TGC GCG TCC CGG GGG GCC TCG GCG CTC CTA
    GCC ACC GCG CTT

67 CTC TAC GCC GCG CTG GGG GAC GTG GTG CGC TCC GAG CAG CAG ATC CCG CTC TCC
    GTA GTG AAG CTC
```

-continued

```
 133 TGG GCC TCC GCT TTT GGT GGG GAG ATA AAA TCC ATT GCT GCC AAG TAC TCG GGT
     TCC CAG CTT CTG

199 CAA AAG AAA TAC AAA GAG TAT GAG AAA GAC GTT GCC ATT GAA GAA ATC GAC GGT
     CTC CAA CTG GTG

265 AAA AAG CTG GCC AAG AAC ATG GAA GAG ATG TTT CAC AAG AAG TCC GAG GCA GTG
     CGG CGT CTC GTG

331 GAG GCT GCA GAG GAA GCA CAC CTG AAG CAT GAA TTT GAC GCC GAC TTG CAG TAT
     GAA TAC TTC AAT

397 GCC GTG CTG ATC AAC GAG AGA GAC AAA GAT GGG AAC TTT TTG GAA TTG GGA AAG
     GAG TTC ATC TTG

463 GCC CCC AAT GAC CAT TTT AAT AAT TTG CCT GTG AAC ATC AGT CTG AGT GAT GTC
     CAA GTG CCA ACG

529 AAC ATG TAC AAC AAA GAT CCT GCC ATA GTC AAT GGA GTG TAT TGG TCT GAA TCT
     CTA AAC AAA GTT

595 TTT GTA GAC AAC TTC GAT CGG GAC CCG TCT CTC ATA TGG CAG TAC TTT GGA AGT
     GCA AAG GGC TTT

661 TTC AGA CAG TAC CCA GGG ATT AAA TGG GAA CCA GAC GAG AAT GGA GTC ATT GCC
     TTT GAC TGC AGG

727 AAC AGG AAA TGG TAC ATC CAG GCA GCA ACT TCT CCA AAG GAT GTG GTC ATT TTG
     GTG GAC GTC AGC

793 GGG AGC ATG AAA GGA CTC CGC CTG ACC ATC GCC AAG CAA ACA GTC TCC TCG ATA
     CTG GAC ACC CTG

859 GGC GAT GAT GAC TTC TTC AAC ATC ATC ACG TAT AAC GAA GAG CTT CAC TAT GTG
     GAA CCT TGT CTG

925 AAT GGA ACA CTG GTT CAA GCG GAC AGG ACC AAC AAG GAG CAC TTC AGG GAG CAT
     TTG GAC AAA CTT

991 TTT GCC AAA GGG ATT GGA ATG CTC GAT ATT GCG CTG AAC GAG GCC TTC AAT GTA
     CTG AGC GAT TTC

1057 AAC CAC ACC GGA CAA GGA AGC ATT TGC AGC CAG GCC ATT ATG CTC ATA ACC GAT
     GGG GCA GTG GAC

1123 ACC TAC GAC ACC ATC TTT GCA AAG TAC AAT TGG CCA GAG CGA AAG GTT CGA ATC
     TTC ACT TAC CTC

1189 ATT GGA CGA GAG GCT GCT TTT GCA GAC AAT CTC AAG TGG ATG GCT TGT GCT AAC
     AAA GGA TTT TTC

1255 ACC CAG ATC TCC ACC TTG GCT GAT GTG CAG GAA AAT GTC ATG GAA TAC CTC CAT
     GTA CTC AGT CGA

1321 CCC AAA GTC ATC GAC CAG GAA CAT GAT GTG GTG TGG ACC GAA GCG TAC ATC GAC
     AGC ACT CTC CCT

1387 CAG GCT CAA AAG CTT GCT GAT GAT CAG GGC CTC GTC TTG ATG ACC ACA GTG GCC
     ATG CCT GTG TTT

1453 AGT AAG CAG AAC GAA ACT AGG TCA AAG GGC ATT CTT CTG GGT GTG GTT GGC ACA
     GAT GTC CCA GTA

1519 AAA GAG CTT CTG AAG ACC ATC CCC AAA TAC AAG TTA GGA ATT CAT GGT TAT GCC
     TTT GCC ATC ACG

1585 AAT AAT GGA TAC ATC TTG ACA CAC CCG GAG CTC AGG CCC CTG TAT GAA GAA GGG
     AAA AAG CGA AGG

1651 AAG CCT AAT TAC AGT AGT GTG GAT CTC TCG GAA GTC GAG TGG GAA GAT CGG GAT
     GAT GTG TTA CGA

1717 AAT GCC ATG GTG AAT CGG AAG ACT GGG AAA TTC TCC ATG GAA GTG AAG AAG ACT
     GTG GAC AAA GGG

1783 AAA CGG GTT TTG GTG ATG ACC AAT GAC TAC TAC ACA GAC ATC AAG GGT GCT
     CCT TTC AGT TTA

1849 GGT GTG GCG CTC TCC AGG GGC CAC GGG AAA TAC TTC TTC CGA GGG AAT GTA ACC
     ATT GAA GAA GGG
```

```
-continued
1915 CTC CAT GAC TTA GAA CAT CCT GAC GTG TCC TTG GCA GAT GAA TGG TCC TAC TGC
     AAC ACT GAT CTG 1981 CAC CCA GAG CAC CGC CAT CTC TCT CAA CTG GAA GCG ATT AAG CTC TAC CTC AAA
     GGC AAG GAG CCT 2047 CTG CTT CAA TGT GAC AAA GAA TTG ATT CAA GAA GTC CTT TTT GAT GCT GTG GTA
     AGC GCC CCT ATC 2113 GAA GCC TAT TGG ACC AGC CTG GCC CTC AAC AAA TCT GAG AAT TCT GAC AAG GGT
     GTA GAG GTC GCC 2179 TTC CTC GGC ACT CGC ACA GGC CTC TCA AGA ATC AAC CTG TTT GTG GGG GCT GAA
     CAG CTC ACC AAT 2245 CAG GAC TTT CTG AAG GCT AGA GAC AAA GAG AAC ATT TTC AAC GCA GAT CAT TTC
     CCT CTC TGG TAC 2311 AGA AGA GCT GCC GAG CAG ATT CCA GGA AGT TTT GTC TAC TCC ATC CCC TTC AGC
     ACA GGA ACG GTC 2377 AAC AAA AGC AAT GTG GTG ACA GCA AGT ACC TCC ATC CAA CTC CTG GAT GAG CGA
     AAA TCT CCT GTG 2443 GTG GCA GCT GTA GGC ATT CAG ATG AAA CTT GAA TTC TTC CAA AGG AAG TTC TGG
     ATG GCC AGC AGA 2509 CAG TGT GCC TCC CTG GAT GGT AAA TGC TCC ATA AGC TGC GAC GAT GAG ACT GTG
     AAC TGT TAC CTC 2575 ATA GAC AAT AAC GGG TTC ATT CTG GTG TCT GAA GAC TAC ACA CAG ACT GGA GAT
     TTT TTT GGT GAG 2641 GTC GAA GGA GCT GTC ATG AAC AAG TTG TTA ACA ATG GGC TCC TTT AAA AGA ATA
     ACC TTG TAT GAC 2707 TAC CAA GCC ATG TGT AGA GCC AAC AAG GAG AGT AGT GAC AGT GCC CAC GGA CTC
     CTG GAC CCC TAT 2773 AAG GCC TTC CTC TCT GCA GCC AAG TGG ATA GTG ACG AAA CTT GTC TTG TTC CTG
     GTG GAG TTT AAC 2839 CTT TGC AGT TGG TGG CAC TCT GAC ATG ACA GCT AAA GCC CAG AAA CTG AAA CAG
     ACC CTG GAG CCT 2905 TGT GAT ACT GAA TAC CCA GCC TTT GTT TCC GAA CGC ACC ATC AAG GAG ACC ACA
     GGG AAC ATT GCT 2971 TGT GAA GAC TGC TCC AAG TCC TTT GTC ATC CAG CAA ATC CCA AGT AGC AAT CTG
     TTC ATG GTG GTG 3037 GTG GAC AGT AGC TGT CTC TGT GAG TCT GTG GCT CCT ATC ACC ATG GCA CCC ATT
     GAA ATC AGG TAT 3103 AAT GAA TCC CTT AAG TGT GAA CGG TTA AAG GCT CAG AAG ATC AGA CGA CGT CCG
     GAA TCC TGC CAC 3169 GGC TTC ATC CCT GAG GAG AAT GCG AGA GAG TGT GGG GGT GCA TCA AGT CTC CAG
     GCC CAG GTG GCC 3235 TTG CTG CTC CTC CCC CTG GTT TCG AGT CTC TTC TCA AGG TGA CAC TAA CTA ATG
     GGA TGT TCT TTT 3301 GGC ATG CTA TAA ATC ATG GAT AAA CTG TGA ACC CAA CTA TGG TGC GAC ATA GAA
     GAC ATA AGC ATA 3367 GCC CAG CCA TCA GCA TCT CAT GAT TTT AAA CTG TGT GTG ATA GAA ACT CTA ACA
     GGT ACA CTG ACC 3433 AAA AGT TCT CTT TTT ACT TTG CCA ATC ATG CAA ATG TGA GTG CCA CAT GAC CAC
     CCT TCA TCA GAA 3499 ATG GGG CTG TAC TGG GTA GGC AGT GGC CTT CTG CTT GAA AAC CAT GGA AAC CAA
     TTT AAA ACT GTG

3565 TAC TTT TTA AAT AAA GTA TAT TAA AAT CAT AAA A
``` and the deduced amino acid sequence of full-length rat brain α₂δ-3 subunit is SEQ. ID. NO:6.

Translated full-length rat brain α₂δ-3 amino acid sequence (SEQ. ID. NO:6)

```
   1 MAGPGSLCCA SRGASALLAT ALLYAALGDV VRSEQQIPLS VVKLWASAFG
  51 GEIKSIAAKY SGSQLLQKKY KEYEKDVAIE EIDGLQLVKK LAKNMEEMFH
 101 KKSEAVRRLV EAAEEAHLKH EFDADLQYEY FNAVLINERD KDGNFLELGK
 151 EFILAPNDHF NNLPVNISLS DVQVPTNMYN KDPAIVNGVY WSESLNKVFV
 201 DNFDRDPSLI WQYFGSAKGF FRQYPGIKWE PDENGVIAFD CRNRKWYIQA
 251 ATSPKDVVIL VDVSGSMKGL RLTIAKQTVS SILDTLGDDD FFNIITYNEE
 301 LHYVEPCLNG TLVQADRTNK EHFREHLDKL FAKGIGMLDI ALNEAFNVLS
 351 DFNHTGQGSI CSQAIMLITD GAVDTYDTIF AKYNWPERKV RIFTYLIGRE
 401 AAFADNLKWM ACANKGFFTQ ISTLADVQEN VMEYLHVLSR PKVIDQEHDV
 451 VWTEAYIDST LPQAQKLADD QGLVLMTTVA MPVFSKQNET RSKGILLGVV
 501 GTDVPVKELL KTIPKYKLGI HGYAFAITNN GYILTHPELR PLYEEGKKRR
 551 KPNYSSVDLS EVEWEDRDDV LRNAMVNRKT GKFSMEVKKT VDKGKRVLVM
 601 TNDYYYTDIK GAPFSLGVAL SRGHGKYFFR GNVTIEEGLH DLEHPDVSLA
 651 DEWSYCNTDL HPEHRHLSQL EAIKLYLKGK EPLLQCDKEL IQEVLFDAVV
 701 SAPIEAYWTS LALNKSENSD KGVEVAFLGT RTGLSRINLF VGAEQLTNQD
 751 FLKARDKENI FNADHFPLWY RRAAEQIPGS FVYSIPFSTG TVNKSNVVTA
 801 STSIQLLDER KSPVVAAVGI QMKLEFFQRK FWMASRQCAS LDGKCSISCD
 851 DETVNCYLID NNGFILVSED YTQTGDFFGE VEGAVMNKLL TMGSFKRITL
 901 YDYQAMCRAN KESSDSAHGL LDPYKAFLSA AKWIVTELVL FLVEFNLCSW
 951 WHSDMTAKAQ KLKQTLEPCD TEYPAFVSER TIKETTGNIA CEDCSKSFVI
1001 QQIPSSNLFM VVVDSSCLCE SVAPITMAPI EIRYNESLKC ERLKAQKIRR
1051 RPESCHGFHP EENARECGGA SSLQAQVALL LLPLVSSLFS R*
```

The rat brain α₂δ-3 truncated variant cDNA clone (clone 1/7-3-1-1) has SEQ. ID. NO:8: Truncated rat brain α₂δ-3 variant calcium channel subunit nucleotide sequence (SEQ ID NO:8)

```
  1 ATGGCCGGGC CGGGCTCGCT GTGCTGCGCG TCCCGGGGGG CCTCGGCGCT
 51 CCTAGCCACC GCGCTTCTCT ACGCCGCGCT GGGGGACGTG GTGCGCTCCG
101 AGCAGCAGAT CCCGCTCTCC GTAGTGAAGC TCTGGGCCTC CGCTTTTGGT
151 GGGGAGATAA AATCCATTGC TGCCAAGTAC TCGGGTTCCC AGCTTCTGCA
201 AAAGAAATAC AAAGAGTATG AGAAAGACGT TGCCATTGAA GAAATCGACG
251 GTCTCCAACT GGTGAAAAAG CTGGCCAAGA ACATGGAAGA GATGTTTCAC
301 AAGAAGTCCG AGGCAGTGCG GCGTCTCGTG GAGGCTGCAG AGGAAGCACA
351 CCTGAAGCAT GAATTTGACG CCGACTTGCA GTATGAATAC TTCAATGCCG
401 TGCTGATCAA CGAGAGAGAC AAAGATGGGA ACTTTTTGGA ATTGGGAAAG
451 GAGTTCATCT TGGCCCCCAA TGACCATTTT AATAATTTGC CTGTGAACAT
501 CAGTCTGAGT GATGTCCAAG TGCCAACGAA CATGTACAAC AAAGATCCTG
```

-continued

```
 551 CCATAGTCAA TGGAGTGTAT TGGTCTGAAT CTCTAAACAA AGTTTTTGTA

601 GACAACTTCG ATCGGGACCC GTCTCTCATA TGGCAGTACT TTGGAAGTGC

651 AAAGGGCTTT TTCAGACAGT ACCCAGGGAT TAAATGGGAA CCAGACGAGA

701 ATGGAGTCAT TGCCTTTGAC TGCAGGAACA GGAAATGGTA CATCCAGGCA

751 GCAACTTCTC CAAAGGATGT GGTCATTTTG GTGGACGTCA GCGGGAGCAT

801 GAAAGGACTC CGCCTGACCA TCGCCAAGCA AACAGTCTCC TCGATACTGG

851 ACACCCTGGG CGATGATGAC TTCTTCAACA TCATCACGTA TAACGAAGAG

901 CTTCACTATG TGGAACCTTG TCTGAATGGA ACACTGGTTC AAGCGGACAG

951 GACCAACAAG GAGCACTTCA GGGAGCATTT GGACAAACTT TTTGCCAAAG

1001 GGATTGGAAT GCTCGATATT GCGCTGAACG AGGCCTTCAA TGTACTGAGC

1051 GATTTCAACC ACACCGGACA AGGAAGCATT TGCAGCCAGG CCATTATGCT

1101 CATAACCGAT GGGGCAGTGG ACACCTACGA CACCATCTTT GCAAAGTACA

1151 ATTGGCCAGA GCGAAAGGTT CGAATCTTCA CTTACCTCAT TGGACGAGAG

1201 GCTGCTTTTG CAGACAATCT CAAGTGGATG GCTTGTGCTA ACAAAGGATT

1251 TTTCACCCAG ATCTCCACCT TGGCTGATGT GCAGGAAAAT GTCATGGAAT

1301 ACCTCCATGT ACTCAGTCGA CCCAAAGTCA TCGACCAGGA ACATGATGTG

1351 GTGTGGACCG AAGCGTACAT CGACAGCACT CTCCCTCAGG CTCAAAAGCT

1401 TGCTGATGAT CAGGGCCTCG TCTTGATGAC CACAGTGGCC ATGCCTGTGT

1451 TTAGTAAGCA GAACGAAACT AGGTCAAAGG GCATTCTTCT GGGTGTGGTT

1501 GGCACAGATG TCCCAGTAAA AGAGCTTCTG AAGACCATCC CCAAATACAA

1551 GTTAGGAATT CATGGTTATG CCTTTGCCAT CACGAATAAT GGATACATCT

1601 TGACACACCC GGAGCTCAGG CCCCTGTATG AAGAAGGGAA AAAGCGAAGG

1651 AAGCCTAATT ACAGTAGTGT GGATCTCTCG GAAGTCGAGT GGGAAGATCG

1701 GGATGATGTG TTACGAAATG CCATGGTGAA TCGGAAGACT GGGAAATTCT

1751 CCATGGAAGT GAAGAAGACT GTGGACAAAG GGAAACGGGT TTTGGTGATG

1801 ACCAATGACT ACTACTACAC AGACATCAAG GGTGCTCCTT TCAGTTTAGG

1851 TGTGGCGCTC TCCAGGGGCC ACGGGAAATA CTTCTTCCGA GGGAATGTAA

1901 CCATTGAAGA AGGGCTCCAT GACTTAGAAC ATCCTGACGT GTCCTTGGCA

1951 GATGAATGGT CCTACTGCAA CACTGATCTG CACCCAGAGC ACCGCCATCT

2001 CTCTCAACTG GAAGCGATTA AGCTCTACCT CAAAGGCAAG GAGCCTCTGC

2051 TTCAATGTGA CAAAGAATTG ATTCAAGAAG TCCTTTTTGA TGCTGTGGTA

2101 AGCGCCCCTA TCGAAGCCTA TTGGACCAGC CTGGCCCTCA ACAAATCTGA

2151 GAATTCTGAC AAGGGTGTAG AGGTCGCCTT CCTCGGCACT CGCACAGGCC

2201 TCTCAAGAAT CAACCTGTTT GTGGGGGCTG AACAGCTCAC CAATCAGGAC

2251 TTTCTGAAGG CTAGAGACAA AGAGAACATT TTCAACGCAG ATCATTTCCC

2301 TCTCTGGTAC AGAAGAGCTG CCGAGCAGAT TCCAGGAAGT TTTGTCTACT

2351 CCATCCCCTT CAGCACAGGA ACGGTCAACA AAAGCAATGT GGTGACAGCA

2401 AGTACCTCCA TCCAACTCCT GGATGAGCGA AAATCTCCTG TGGTGGCAGC

2451 CCAGAAACTG AAACAGACCC TGGAGCCTTG TGATACTGAA TACCCAGCCT

2501 TTGTTTCCGA ACGCACCATC AAGGAGACCA CAGGGAACAT TGCTTGTGAA
```

-continued

```
2551 GACTGCTCCA AGTCCTTTGT CATCCAGCAA ATCCCAAGTA GCAATCTGTT

2601 CATGGTGGTG GTGGACAGTA GCTGTCTCTG TGAGTCTGTG GCTCCTATCA

2651 CCATGGCACC CATTGAAATC AGGTATAATG AATCCCTTAA GTGTGAACGG

2701 TTAAAGGCTC AGAAGATCAG ACGACGTCCG GAATCCTGCC ACGGCTTCCA

2751 TCCTGAGGAG AATGCGAGAG AGTGTGGGGG TGCATCAAGT CTCCAGGCCC

2801 AGGTGGCCTT GCTGCTGCTC CCCCTGGTTT CGAGTCTCTT CTCAAGGTGA

2851 CACTAACTAA TGGGATGTTC TTTTGGCATG CTATAAATCA TGGATAAACT

2901 GTGAACCCAA CTATGGTGCG ACATAGAAGA CATAAGCATA GCCCAGCCAT

2951 CAGCATCTCA TGATTTTAAA CTGTGTGTGA TAGAAACTCT AACAGGTACA

3001 CTGACCAAAA GTTCTCTTTT TACTTTGCCA ATCATGCAAA TGTGAGTGCC

3051 ACATGACCAC CCTTCATCAG AAATGGGGCT GTACTGGGTA GGCAGTGGCC

3101 TTCTGCTTGA AAACCATGGA AACCAATTTA AAACTGTGTA CTTTTTAAAT

3151 AAAGTATATT AAAATCATAA AA
``` and the deduced amino acid sequence of rat brain $\alpha_2\delta$-3 truncated variant is SEQ. ID. NO:9:

Translated rat brain $\alpha_2\delta$-3 variant amino acid sequence (SEQ. ID. NO:9)

```
  1 MAGPGSLCCA SRGASALLAT ALLYAALGDV VRSEQQIPLS VVKLWASAFG

51 GEIKSIAAKY SGSQLLQKKY KEYEKDVAIE EIDGLQLVKK LAKNMEEMFH

101 KKSEAVRRLV EAAEEAHLKH EFDADLQYEY FNAVLINERD KDGNFLELGK

151 EFILAPNDHF NNLPVNISLS DVQVPTNMYN KDPAIVNGVY WSESLNKVFV

201 DNFDRDPSLI WQYFGSAKGF FRQYPGIKWE PDENGVIAFD CRNRKWYIQA

251 ATSPKDVVIL VDVSGSMKGL RLTIAKQTVS SILDTLGDDD FFNIITYNEE

301 LHYVEPCLNG TLVQADRTNK EHFREHLDKL FAKGIGMLDI ALNEAFNVLS

351 DFNHTGQGSI CSQAIMLITD GAVDTYDTIF AKYNWPERKV RIFTYLIGRE

401 AAFADNLKWM ACANKGFFTQ ISTLADVQEN VMEYLHVLSR PKVIDQEHDV

451 VWTEAYIDST LPQAQKLADD QGLVLMTTVA MPVFSKQNET RSKGILLGVV

501 GTDVPVKELL KTIPKYKLGI HGYAFAITNN GYILTHPELR PLYEEGKKRR

551 KPNYSSVDLS EVEWEDRDDV LRNAMVNRKT GKFSMEVKKT VDKGKRVLVM

601 TNDYYYTDIK GAPFSLGVAL SRGHGKYFFR GNVTIEEGLH DLEHPDVSLA

651 DEWSYCNTDL HPEHRHLSQL EAIKLYLKGK EPLLQCDKEL IQEVLFDAVV

701 SAPIEAYWTS LALNKSENSD KGVEVAFLGT RTGLSRINLF VGAEQLTNQD

751 FLKARDKENI FNADHFPLWY RRAAEQIPGS FVYSIPFSTG TVNKSNVVTA

801 STSIQLLDER KSPVVAAQKL KQTLEPCDTE YPAFVSERTI KETTGNIACE

851 DCSKSFVIQQ IPSSNLFMVV VDSSCLCESV APITMAPIEI RYNESLKCER

901 LKAQKIRRRP ESCHGFHPEE NARECGGASS LQAQVALLLL PLVSSLFSR*
```

EXAMPLE 5

Screening for Calcium Channel Blockers

The whole-cell patch clamp recording technique used is as described in Example 2 to screen for calcium channel blockers. Test compounds are added daily to the extracellular recording solution from a stock concentration of 1 mM (in DMSO) for each experiment. Compounds are then applied directly onto the HEK cells by means of a custom-made gravity-driven perfusion system, which changes the solution around the cell in less than 1 s. Differences in the mean peak current densities in the absence and presence of compounds are measured to estimate the concentration of compound required to occupy 50% of the channels ($K_d$). The $K_d$ is estimated using the equation $K_d$=a[drug]/1−a.

---

The invention claimed is:

1. An isolated nucleic acid comprising a nucleotide sequence that encodes a calcium channel subunit having the amino acid sequence of SEQ ID NO: 3 or a fragment thereof which encodes a functional $\alpha_2\delta$-2 subunit, wherein the fragment is a truncated form of SEQ ID NO: 3, wherein the truncation involves removing up to 20 amino acids from the $\alpha_2$ and/or $\delta$ portions.

2. A recombinant nucleic acid molecule which comprises a nucleotide sequence as set forth in claim 1, operably linked to control sequences to effect its expression.

3. The nucleic acid of claim 2, wherein said control sequences are operable in vertebrate cells.

4. Recombinant host cells which contain the nucleic acid molecule of claim 2.

5. Vertebrate host cells which contain the nucleic acid molecule of claim 3.

6. The vertebrate host cells of claim 5, wherein said cells further comprise an expression vector which comprises an expression control sequence operably linked to a nucleotide sequence which encodes an $\alpha_1$ calcium channel subunit.

7. A method to prepare cells that display functional calcium ion channel, which method comprises culturing cells which display an $\alpha_1$ subunit and which further comprise the nucleic acid molecule of claim 2.

8. Recombinant cells prepared by the method of claim 7.

9. The isolated nucleic acid of claim 1 wherein 10–15 of the up to 20 amino acids are removed.

10. The isolated nucleic acid of claim 1 which encodes SEQ ID NO:3.

* * * * *

SEQUENCE LISTING

<160> NUMBER OF SEQ ID NOS: 22

<210> SEQ ID NO 1
<211> LENGTH: 1157
<212> TYPE: PRT
<213> ORGANISM: Rattus norvegicus

<400> SEQUENCE: 1

```
Met Ala Val Pro Ala Arg Thr Cys Gly Ala Ser Trp Pro Gly Pro Val
 1               5                  10                  15

Arg Thr Ala Arg Pro Trp Pro Gly Arg Gly Pro Arg Pro Cys Pro Asp
             20                  25                  30

Pro Arg Gly Pro Ala Ser Gly Pro Ala Arg Pro Leu Leu Leu Leu Leu
         35                  40                  45

Pro Pro Leu Leu Leu Leu Pro Leu Leu Thr Ala Pro Gly Ala Ser Ala
 50                  55                  60

Tyr Ser Phe Pro Gln Gln His Thr Met Gln His Trp Ala Arg Arg Leu
 65                  70                  75                  80

Glu Gln Glu Ile Asp Gly Val Met Arg Ile Phe Gly Gly Val Gln Gln
                 85                  90                  95

Leu Arg Glu Ile Tyr Lys Asp Asn Arg Asn Leu Phe Asp Val Gln Glu
            100                 105                 110

Asn Glu Pro Gln Lys Leu Val Glu Lys Val Ala Gly Asp Ile Glu Ser
        115                 120                 125

Leu Leu Asp Arg Lys Val Gln Ala Leu Lys Arg Leu Ala Asp Ala Ala
130                 135                 140

Glu Asn Phe Gln Lys Ala His Arg Trp Gln Asp Asn Ile Lys Glu Glu
145                 150                 155                 160

Asp Ile Met Tyr Tyr Asp Ala Lys Ala Asp Ala Glu Leu Asp Asp Pro
                165                 170                 175

Glu Ser Glu Asp Met Glu Arg Gly Ser Lys Thr Ser Ala Leu Arg Leu
            180                 185                 190

Asp Phe Ile Glu Glu Pro Asn Phe Lys Asn Lys Val Asn Tyr Ser Tyr
        195                 200                 205

Thr Ala Val Gln Ile Pro Thr Asp Ile Tyr Lys Gly Ser Thr Val Ile
    210                 215                 220

Leu Asn Glu Leu Asn Trp Thr Glu Ala Leu Glu Asn Val Phe Ile Glu
225                 230                 235                 240

Asn Arg Arg Gln Asp Pro Thr Leu Leu Trp Gln Val Phe Gly Ser Ala
                245                 250                 255

Thr Gly Val Thr Arg Tyr Tyr Pro Ala Thr Pro Trp Arg Ala Pro Lys
            260                 265                 270

Lys Ile Asp Leu Tyr Asp Val Arg Arg Arg Pro Trp Tyr Ile Gln Gly
        275                 280                 285

Ala Ser Ser Pro Lys Asp Met Val Ile Ile Val Asp Val Ser Gly Ser
    290                 295                 300
```

-continued

```
Val Ser Gly Leu Thr Leu Lys Leu Met Lys Thr Ser Val Cys Glu Met
305                 310                 315                 320

Leu Asp Thr Leu Ser Asp Asp Tyr Val Asn Val Ala Ser Phe Asn
            325                 330                 335

Glu Lys Ala Gln Pro Val Ser Cys Phe Thr His Leu Val Gln Ala Asn
            340                 345                 350

Val Arg Asn Lys Lys Val Phe Lys Glu Ala Val Gln Gly Met Val Ala
            355                 360                 365

Lys Gly Thr Thr Gly Tyr Lys Ala Gly Phe Glu Tyr Ala Phe Asp Gln
            370                 375                 380

Leu Gln Asn Ser Asn Ile Thr Arg Ala Asn Cys Asn Lys Met Ile Met
385                 390                 395                 400

Met Phe Thr Asp Gly Gly Glu Asp Arg Val Gln Asp Val Phe Glu Lys
                405                 410                 415

Tyr Asn Trp Pro Asn Arg Thr Val Arg Val Phe Thr Phe Ser Val Gly
                420                 425                 430

Gln His Asn Tyr Asp Val Thr Pro Leu Gln Trp Met Ala Cys Thr Asn
            435                 440                 445

Lys Gly Tyr Tyr Phe Glu Ile Pro Ser Ile Gly Ala Ile Arg Ile Asn
    450                 455                 460

Thr Gln Glu Tyr Leu Asp Val Leu Gly Arg Pro Met Val Leu Ala Gly
465                 470                 475                 480

Lys Asp Ala Lys Gln Val Gln Trp Thr Asn Val Tyr Glu Asp Ala Leu
            485                 490                 495

Gly Leu Gly Leu Val Val Thr Gly Thr Leu Pro Val Phe Asn Leu Thr
            500                 505                 510

Gln Asp Gly Pro Gly Asp Lys Lys Asn Gln Leu Ile Leu Gly Val Met
            515                 520                 525

Gly Ile Asp Val Ala Leu Asn Asp Ile Lys Arg Leu Thr Pro Asn Tyr
    530                 535                 540

Thr Leu Gly Ala Asn Gly Tyr Val Phe Ala Ile Asp Leu Asn Gly Tyr
545                 550                 555                 560

Val Leu Leu His Pro Asn Leu Lys Pro Gln Ile Thr Asn Phe Arg Glu
            565                 570                 575

Pro Val Thr Leu Asp Phe Leu Asp Ala Glu Leu Glu Asp Glu Asn Lys
            580                 585                 590

Glu Glu Ile Arg Arg Ser Met Ile Asp Gly Asp Lys Gly His Lys Gln
            595                 600                 605

Ile Arg Thr Leu Val Lys Ser Leu Asp Glu Arg Tyr Ile Asp Glu Val
    610                 615                 620

Ile Arg Asn Tyr Thr Trp Val Pro Ile Arg Ser Thr Asn Tyr Ser Leu
625                 630                 635                 640

Gly Leu Val Leu Pro Pro Tyr Ser Thr Tyr Tyr Leu Gln Ala Asn Leu
            645                 650                 655

Ser Asp Gln Ile Leu Gln Val Lys Leu Pro Ile Ser Lys Leu Lys Asp
            660                 665                 670

Phe Glu Phe Leu Leu Pro Ser Ser Phe Glu Ser Glu Gly His Val Phe
            675                 680                 685

Ile Ala Pro Arg Glu Tyr Cys Lys Asp Leu Asn Ala Ser Asp Asn Asn
    690                 695                 700

Thr Glu Phe Leu Lys Asn Phe Ile Glu Leu Met Glu Lys Val Thr Pro
705                 710                 715                 720
```

-continued

```
Asp Ser Lys Gln Cys Asn Asn Phe Leu Leu His Asn Leu Ile Leu Asp
            725                 730                 735
Thr Gly Ile Thr Gln Gln Leu Val Glu Arg Val Trp Arg Asp Gln Asp
            740                 745                 750
Leu Asn Thr Tyr Ser Leu Leu Ala Val Phe Ala Ala Thr Asp Gly Gly
            755                 760                 765
Ile Thr Arg Val Phe Pro Asn Lys Ala Ala Glu Asp Trp Thr Glu Asn
            770                 775                 780
Pro Glu Pro Phe Asn Ala Ser Phe Tyr Arg Arg Ser Leu Asp Asn Arg
785                 790                 795                 800
Gly Tyr Ile Phe Lys Pro Pro His Gln Asp Ser Leu Leu Arg Pro Leu
                    805                 810                 815
Glu Leu Glu Asn Asp Thr Val Gly Val Leu Val Ser Thr Ala Val Glu
                    820                 825                 830
Leu Ser Leu Gly Arg Arg Thr Leu Arg Pro Ala Val Val Gly Val Lys
            835                 840                 845
Leu Asp Leu Glu Ala Trp Ala Glu Lys Phe Lys Val Leu Ala Ser Asn
850                 855                 860
Arg Thr His Gln Asp Gln Pro Gln Lys Gln Cys Gly Pro Ser Ser His
865                 870                 875                 880
Cys Glu Met Asp Cys Glu Val Asn Asn Glu Asp Leu Leu Cys Val Leu
                    885                 890                 895
Ile Asp Asp Gly Gly Phe Leu Val Leu Ser Asn Gln Asn His Gln Trp
                    900                 905                 910
Asp Gln Val Gly Arg Phe Phe Ser Glu Val Asp Ala Asn Leu Met Leu
            915                 920                 925
Ala Leu Tyr Asn Asn Ser Phe Tyr Thr Arg Lys Glu Ser Tyr Asp Tyr
            930                 935                 940
Gln Ala Ala Cys Ala Pro Gln Pro Pro Gly Asn Leu Gly Ala Ala Pro
945                 950                 955                 960
Arg Gly Val Phe Val Pro Thr Ile Ala Asp Phe Leu Asn Leu Ala Trp
                    965                 970                 975
Trp Thr Ser Ala Ala Trp Ser Leu Phe Gln Gln Leu Leu Tyr Gly
                    980                 985                 990
Leu Ile Tyr His Ser Trp Phe Gln Ala Asp Pro Ala Glu Ala Glu Gly
            995                 1000                1005
Ser Pro Glu Thr Arg Glu Ser Ser Cys Val Met Lys Gln Thr Gln Tyr
            1010                1015                1020
Tyr Phe Gly Ser Val Asn Ala Ser Tyr Asn Ala Ile Ile Asp Cys Gly
1025                1030                1035                1040
Asn Cys Ser Arg Leu Phe His Ala Gln Arg Leu Thr Asn Thr Asn Leu
                    1045                1050                1055
Leu Phe Val Val Ala Glu Lys Pro Leu Cys Ser Gln Cys Glu Val Gly
                    1060                1065                1070
Arg Leu Leu Gln Lys Glu Thr His Cys Pro Ala Asp Gly Pro Glu Gln
            1075                1080                1085
Cys Glu Leu Val Gln Arg Pro Arg Tyr Arg Thr Gly Pro His Ile Cys
            1090                1095                1100
Phe Asp Tyr Asn Ala Thr Glu Asp Thr Ser Asp Cys Gly Arg Gly Ala
1105                1110                1115                1120
Ser Phe Pro Pro Ser Leu Gly Val Leu Val Ser Leu Gln Leu Leu Leu
                    1125                1130                1135
```

Leu Leu Gly Leu Pro Pro Arg Pro Gln Pro Gln Ile His Ser Phe Thr
           1140                1145                1150
Pro Ser Arg Arg Leu
        1155

<210> SEQ ID NO 2
<211> LENGTH: 4993
<212> TYPE: DNA
<213> ORGANISM: Rattus norvegicus
<220> FEATURE:
<221> NAME/KEY: misc_feature
<222> LOCATION: 3902
<223> OTHER INFORMATION: n = a, c, g, or t

<400> SEQUENCE: 2

| | | | | | |
|---|---|---|---|---|---|
| cggcgccgca | tcttgaatgg | aaacatggcg | gtgccggctc | ggacctgcgg | cgcttcttgg | 60 |
| cccggcccgg | tgcggaccgc | tcgccctgg | cccggtcgcg | gtccccggcc | ctgccctgac | 120 |
| ccccggggcc | cagcgtccgg | gcccgcacgc | ccgctcttgc | tactgctgcc | gcctctgctg | 180 |
| cttttaccgc | tgctcaccgc | ccccggcgcc | tctgcctaca | gcttccccca | gcagcacacg | 240 |
| atgcagcact | gggcccggcg | cctggagcag | gagattgacg | tgtgatgcg | gattttgga | 300 |
| ggcgtgcagc | agctccgaga | gatctacaag | gacaatcgga | acctgtttga | tgtgcaggag | 360 |
| aatgaaccac | agaaactagt | ggagaaggtg | gcagggaca | ttgagagcct | gctggacaga | 420 |
| aaggtccagg | ccttgaagag | actggctgac | gctgcagaga | atttccagaa | agcccaccgc | 480 |
| tggcaagaca | catcaagga | ggaagacatc | atgtactatg | acgccaaggc | tgacgccgag | 540 |
| ctggatgatc | ctgagagtga | ggatatggag | aggggatcca | agaccagcgc | cttaaggctg | 600 |
| gacttcatcg | aggagccaaa | cttcaagaac | aaagtcaact | attcatacac | ggcggtgcag | 660 |
| atccccacag | atatctacaa | aggctctacc | gtcatcctca | atgagcttaa | ctggacggag | 720 |
| gccctggaga | atgtcttcat | tgagaaccgt | aggcaagacc | ctacactgtt | gtggcaagtc | 780 |
| ttcggcagtg | ccacgggagt | cacccgctat | acccagcca | caccgtggcg | agcccccaag | 840 |
| aagattgacc | tgtacgatgt | cagaagacga | ccctggtata | tacaggggc | ctcatcaccc | 900 |
| aaggacatgg | tcatcattgt | ggatgtgagt | ggcagtgtga | gcggcctgac | gctgaagctg | 960 |
| atgaagacgt | ctgtctgtga | gatgctagac | acactctccg | atgatgacta | tgtgaatgtg | 1020 |
| gcctcattca | acgagaaggc | gcagcctgtg | tcttgcttca | cacacctggt | gcaggccaat | 1080 |
| gtgcggaaca | agaaggtgtt | caaggaagct | gtgcagggca | tggtggccaa | gggcaccaca | 1140 |
| ggctacaagg | ctgcttga | gtatgccttt | gaccagctac | agaattccaa | catcacccgt | 1200 |
| gctaactgca | ataagatgat | catgatgttc | acggacgggg | gagaggatcg | cgtgcaggac | 1260 |
| gtctttgaaa | agtataattg | gcccaatcgg | acggtacgcg | tcttcacgtt | ctccgtagga | 1320 |
| cagcataact | atgatgtcac | acccctgcag | tggatggctt | gtactaacaa | aggttactat | 1380 |
| tttgagatcc | cttccatcgg | agccatccgc | atcaacacac | aggaatacct | ggatgtgctg | 1440 |
| ggtaggccca | tggtcctggc | aggcaaggac | gccaagcaag | tgcaatggac | aaacgtgtat | 1500 |
| gaagatgcgc | tggggctggg | gttggtggta | acagggactc | tccctgtttt | caacctgaca | 1560 |
| caggatggcc | ctgggaaaa | gaagaaccag | ctaatcctgg | gtgtcatggg | catagatgtg | 1620 |
| gccctgaatg | acatcaaaag | gctgactccc | aactacacac | ttgcgccaa | tggctacgtg | 1680 |
| ttcgccatcg | acctgaatgg | ctatgtgttg | ctacatccca | atctcaagcc | ccagactacc | 1740 |
| aacttccggg | agcctgtgac | cttggacttc | ctggatgcag | agctggaaga | tgagaacaag | 1800 |
| gaggagatcc | gtcgtagtat | gattgacgaa | gacaaaggcc | acaagcagat | cagaaccttg | 1860 |

```
gtcaaatccc tggatgagag gtacatagat gaagtgattc ggaactacac ctgggtgcct    1920
ataaggagta ccaactacag cctggggctg gtgctcccac cctacagcac ctactacctc    1980
caagccaacc tcagcgacca gatcctgcag gtcaagtatt ttgagttcct gctccccagc    2040
agctttgagt ctgaaggaca tgttttcatt gctcccagag agtattgcaa ggatttgaat    2100
gcctcagaca acaacaccga gttcctgaaa aacttcattg agctcatgga gaaagtgact    2160
ccggactcca agcagtgcaa taacttcctt ctgcataact tgattttgga cacgggcatt    2220
acgcagcagt tagtggaacg cgtctggcgg gaccaagatc tcaacacgta cagcctgcta    2280
gctgtatttg ctgccactga cggtgcagtc acacgtgtct cccgaacaa ggcagctgaa     2340
gactggacag aaaaccctga acccttcaat gccagcttct accgccgcag cctggataac    2400
cgtggttata tcttcaagcc cccgcaccag gactccctgt taaggccact ggagctggag    2460
aatgacacag taggcgtcct cgtcagcaca gctgtagagc tcagtctggg tcgccgcaca    2520
ctgaggccag cagtggtggg tgtcaaactg gacctagagg cttgggctga aaagttcaag    2580
gtgcttgcca gcaaccgtac ccatcaggac caacctcaga agcagtgcgg ccccagcagc    2640
cactgtgaga tggactgcga ggtaaacaac gaggacctac tctgtgtcct cattgatgac    2700
gggggattcc tggtgctgtc aaaccagaac caccagtggg accaggttgg cagattcttc    2760
agtgaggtgg atgccaacct gatgctggca ctgtacaata actccttcta caccagaaag    2820
gagtcctatg actatcaggc agcttgtgcc cctcagcctc ctggcaacct gggtgctgca    2880
cccaggggtg tctttgtgcc caccattgca gatttcctta acttggcctg gtggaccctct   2940
gctgccgcct ggtccttatt ccagcaacta ctttatggtc tcatctatca cagctggttc    3000
caggcagacc cggcagaagc cgagggcagc cccgagacgc gcgagagcag ctgcgtcatg    3060
aaacaaaccc agtactactt cggctcggtg aacgcgtcct ataacgccat catcgactgc    3120
ggaaactgca gcaggctgtt ccacgcgcag agactgacca acaccaacct tctgttcgtg    3180
gtggcggaga agccgctgtg cagccagtgc gaggtcggcc ggctgctaca aaaggagaca    3240
cactgcccag cggacggccc ggagcagtgt gagctggtgc agagaccgcg ataccgaaga    3300
ggcccgcaca tctgtttttga ctacaatgcg acggaagata cctcagactg tggccgcggc    3360
acgtccttcc ctccgtcgct gggcgtcttg gtttccctgc agctgttgct cctcctaggc    3420
ctgccacctc ggccgcagcc tcaaatccat tccttcgctg cctctcgccg cctctgaact    3480
acccacacac acacatcata gcccccaccc ccaccccgcc ttggcctcct agccttttcg    3540
ctcaccctcc catgccacat tccccaatct agatccttgg ccagtctctc ctgaaggaac    3600
tgggcccctt ccccggagcc tgtgccttgg ggcaggggag ccaaagtaag gtgccatggt    3660
gtttggcact caagatttat ctcaccctgg aactgtccaa gtgcccacag tccctggact    3720
caccctgtg gttgggacag gaggccacta gtaccgatgc caaaccaggc ctccaccaac     3780
ccacctgcct ggagattttc tctatgtagg caaccctgcc actgctgggc gcctctaact    3840
ggcccttttgc cccacccagg cccaaactta ccttctctgg ggaaaaaact aggagagatg   3900
gntagtggtg agagagattc tgggggcacc ccttccccat agcctcgggc cgttccaggc    3960
tacaccacaa acccacacct cggcttgcag gtatcaggac agcctcacga tgacatcagc    4020
ttaggcacac cccacagaca cctggacctc agagagcaga aactggactc tcactagaca    4080
tgcccgagag ggaacacaca aacagacaca caccatgggg gacccacaaa gccttacaca    4140
gggcgagagg tcagtgaagg ggctgacctg tgtgttcctt ctccgctcac ctctgcctcc    4200
actctgagat gcagcctggc aggccctccc atctctagaa ctgaatgtca gaccgtgcca    4260
```

-continued

```
aatgctaggg gaaggcctct gtttcgcccc tagccaccag tgtccccaaa tgcccctcac    4320
cctgccaggt gctcattgta accattgctc actagtgtca ggcccctagt aggaccacat    4380
gtcactgcct gaacccottt ggcagaagaa ccccgccaga cattgtactt tgccttagca    4440
ggggtgactt ggtctctcct ggctgggcca tcccatcccc aatctggttc ttacatactc    4500
aggcctaatt ccctcttcac acacacacac acacacacac acacacacac acacacacag    4560
tccctgcccc taggaggcca tattgcccct cccttgctga acacacactt gcaccaagca    4620
catgtgtagt caaccatact gcacacacag aggctgggcc tgggacacat ctcttcacac    4680
cattcattct gtcatttctc ccaaaggcat cgtaacctgg gggccaggcg gggactgagg    4740
gcagggtggg ggggtgtgtg gccatgaggc tcagatggac tgggaggagg gtgggagggt    4800
ggtacattaa ttaatggctc cgttaattaa tgtcatgttg cgtgttgctt tctcagtgtg    4860
tgtatggtcc atgcccaatg ctggtggcag ggtgggtgtc catgatgtgt gcccagcctg    4920
gatgtcagct gtgtcctgtg ggggcgtgtg tgtaactgta gtgtagtcag gtgctcaacg    4980
gagaatacaa acg                                                       4993
```

<210> SEQ ID NO 3
<211> LENGTH: 1150
<212> TYPE: PRT
<213> ORGANISM: Rattus norvegicus

<400> SEQUENCE: 3

```
Met Ala Val Pro Ala Arg Thr Cys Gly Ala Ser Trp Pro Gly Pro Val
  1               5                  10                  15

Arg Thr Ala Arg Pro Trp Pro Gly Arg Gly Pro Arg Pro Cys Pro Asp
                 20                  25                  30

Pro Arg Gly Pro Ala Ser Gly Pro Ala Arg Pro Leu Leu Leu Leu Leu
             35                  40                  45

Pro Pro Leu Leu Leu Leu Pro Leu Leu Thr Ala Pro Gly Ala Ser Ala
         50                  55                  60

Tyr Ser Phe Pro Gln Gln His Thr Met Gln His Trp Ala Arg Arg Leu
 65                  70                  75                  80

Glu Gln Glu Ile Asp Gly Val Met Arg Ile Phe Gly Gly Val Gln Gln
                 85                  90                  95

Leu Arg Glu Ile Tyr Lys Asp Asn Arg Asn Leu Phe Asp Val Gln Glu
            100                 105                 110

Asn Glu Pro Gln Lys Leu Val Glu Lys Val Ala Gly Asp Ile Glu Ser
        115                 120                 125

Leu Leu Asp Arg Lys Val Gln Ala Leu Lys Arg Leu Ala Asp Ala Ala
    130                 135                 140

Glu Asn Phe Gln Lys Ala His Arg Trp Gln Asp Asn Ile Lys Glu Glu
145                 150                 155                 160

Asp Ile Met Tyr Tyr Asp Ala Lys Ala Asp Ala Glu Leu Asp Asp Pro
                165                 170                 175

Glu Ser Glu Asp Met Glu Arg Gly Ser Lys Thr Ser Ala Leu Arg Leu
            180                 185                 190

Asp Phe Ile Glu Glu Pro Asn Phe Lys Asn Lys Val Asn Tyr Ser Tyr
        195                 200                 205

Thr Ala Val Gln Ile Pro Thr Asp Ile Tyr Lys Gly Ser Thr Val Ile
    210                 215                 220

Leu Asn Glu Leu Asn Trp Thr Glu Ala Leu Glu Asn Val Phe Ile Glu
225                 230                 235                 240
```

```
Asn Arg Arg Gln Asp Pro Thr Leu Leu Trp Gln Val Phe Gly Ser Ala
            245                 250                 255
Thr Gly Val Thr Arg Tyr Tyr Pro Ala Thr Pro Trp Arg Ala Pro Lys
            260                 265                 270
Lys Ile Asp Leu Tyr Asp Val Arg Arg Pro Trp Tyr Ile Gln Gly
            275                 280                 285
Ala Ser Ser Pro Lys Asp Met Val Ile Ile Val Asp Val Ser Gly Ser
290                     295                 300
Val Ser Gly Leu Thr Leu Lys Leu Met Lys Thr Ser Val Cys Glu Met
305                 310                 315                 320
Leu Asp Thr Leu Ser Asp Asp Tyr Val Asn Val Ala Ser Phe Asn
                    325                 330                 335
Glu Lys Ala Gln Pro Val Ser Cys Phe Thr His Leu Val Gln Ala Asn
            340                 345                 350
Val Arg Asn Lys Lys Val Phe Lys Glu Ala Val Gln Gly Met Val Ala
            355                 360                 365
Lys Gly Thr Thr Gly Tyr Lys Ala Gly Phe Glu Tyr Ala Phe Asp Gln
    370                 375                 380
Leu Gln Asn Ser Asn Ile Thr Arg Ala Asn Cys Asn Lys Met Ile Met
385                 390                 395                 400
Met Phe Thr Asp Gly Gly Glu Asp Arg Val Gln Asp Val Phe Glu Lys
                405                 410                 415
Tyr Asn Trp Pro Asn Arg Thr Val Arg Val Phe Thr Phe Ser Val Gly
                420                 425                 430
Gln His Asn Tyr Asp Val Thr Pro Leu Gln Trp Met Ala Cys Thr Asn
            435                 440                 445
Lys Gly Tyr Tyr Phe Glu Ile Pro Ser Ile Gly Ala Ile Arg Ile Asn
    450                 455                 460
Thr Gln Glu Tyr Leu Asp Val Leu Gly Arg Pro Met Val Leu Ala Gly
465                 470                 475                 480
Lys Asp Ala Lys Gln Val Gln Trp Thr Asn Val Tyr Glu Asp Ala Leu
                485                 490                 495
Gly Leu Gly Leu Val Val Thr Gly Thr Leu Pro Val Phe Asn Leu Thr
                500                 505                 510
Gln Asp Gly Pro Gly Glu Lys Lys Asn Gln Leu Ile Leu Gly Val Met
            515                 520                 525
Gly Ile Asp Val Ala Leu Asn Asp Ile Lys Arg Leu Thr Pro Asn Tyr
    530                 535                 540
Thr Leu Gly Ala Asn Gly Tyr Val Phe Ala Ile Asp Leu Asn Gly Tyr
545                 550                 555                 560
Val Leu Leu His Pro Asn Leu Lys Pro Gln Thr Asn Phe Arg Glu
                565                 570                 575
Pro Val Thr Leu Asp Phe Leu Asp Ala Glu Leu Glu Asp Glu Asn Lys
            580                 585                 590
Glu Glu Ile Arg Arg Ser Met Ile Asp Glu Asp Lys Gly His Lys Gln
            595                 600                 605
Ile Arg Thr Leu Val Lys Ser Leu Asp Glu Arg Tyr Ile Asp Glu Val
            610                 615                 620
Ile Arg Asn Tyr Thr Trp Val Pro Ile Arg Ser Thr Asn Tyr Ser Leu
625                 630                 635                 640
Gly Leu Val Leu Pro Pro Tyr Ser Thr Tyr Tyr Leu Gln Ala Asn Leu
                645                 650                 655
```

-continued

```
Ser Asp Gln Ile Leu Gln Val Lys Tyr Phe Glu Phe Leu Leu Pro Ser
            660                 665                 670

Ser Phe Glu Ser Glu Gly His Val Phe Ile Ala Pro Arg Glu Tyr Cys
        675                 680                 685

Lys Asp Leu Asn Ala Ser Asp Asn Thr Glu Phe Leu Lys Asn Phe
    690                 695                 700

Ile Glu Leu Met Glu Lys Val Thr Pro Asp Ser Lys Gln Cys Asn Asn
705                 710                 715                 720

Phe Leu Leu His Asn Leu Ile Leu Asp Thr Gly Ile Thr Gln Gln Leu
                725                 730                 735

Val Glu Arg Val Trp Arg Asp Gln Asp Leu Asn Thr Tyr Ser Leu Leu
            740                 745                 750

Ala Val Phe Ala Ala Thr Asp Gly Ala Val Thr Arg Val Phe Pro Asn
        755                 760                 765

Lys Ala Ala Glu Asp Trp Thr Glu Asn Pro Glu Pro Phe Asn Ala Ser
    770                 775                 780

Phe Tyr Arg Arg Ser Leu Asp Asn Arg Gly Tyr Ile Phe Lys Pro Pro
785                 790                 795                 800

His Gln Asp Ser Leu Leu Arg Pro Leu Glu Leu Glu Asn Asp Thr Val
                805                 810                 815

Gly Val Leu Val Ser Thr Ala Val Glu Leu Ser Leu Gly Arg Arg Thr
            820                 825                 830

Leu Arg Pro Ala Val Val Gly Val Lys Leu Asp Leu Glu Ala Trp Ala
        835                 840                 845

Glu Lys Phe Lys Val Leu Ala Ser Asn Arg Thr His Gln Asp Gln Pro
    850                 855                 860

Gln Lys Gln Cys Gly Pro Ser Ser His Cys Glu Met Asp Cys Glu Val
865                 870                 875                 880

Asn Asn Glu Asp Leu Leu Cys Val Leu Ile Asp Asp Gly Gly Phe Leu
                885                 890                 895

Val Leu Ser Asn Gln Asn His Gln Trp Asp Gln Val Gly Arg Phe Phe
            900                 905                 910

Ser Glu Val Asp Ala Asn Leu Met Leu Ala Leu Tyr Asn Asn Ser Phe
        915                 920                 925

Tyr Thr Arg Lys Glu Ser Tyr Asp Tyr Gln Ala Ala Cys Ala Pro Gln
    930                 935                 940

Pro Pro Gly Asn Leu Gly Ala Ala Pro Arg Gly Val Phe Val Pro Thr
945                 950                 955                 960

Ile Ala Asp Phe Leu Asn Leu Ala Trp Trp Thr Ser Ala Ala Ala Trp
                965                 970                 975

Ser Leu Phe Gln Gln Leu Leu Tyr Gly Leu Ile Tyr His Ser Trp Phe
            980                 985                 990

Gln Ala Asp Pro Ala Glu Ala Glu Gly Ser Pro Glu Thr Arg Glu Ser
        995                 1000                1005

Ser Cys Val Met Lys Gln Thr Gln Tyr Tyr Phe Gly Ser Val Asn Ala
    1010                1015                1020

Ser Tyr Asn Ala Ile Ile Asp Cys Gly Asn Cys Ser Arg Leu Phe His
1025                1030                1035                1040

Ala Gln Arg Leu Thr Asn Thr Asn Leu Leu Phe Val Val Ala Glu Lys
                1045                1050                1055

Pro Leu Cys Ser Gln Cys Glu Val Gly Arg Leu Leu Gln Lys Glu Thr
            1060                1065                1070
```

His Cys Pro Ala Asp Gly Pro Glu Gln Cys Glu Leu Val Gln Arg Pro
        1075                1080                1085

Arg Tyr Arg Arg Gly Pro His Ile Cys Phe Asp Tyr Asn Ala Thr Glu
        1090                1095                1100

Asp Thr Ser Asp Cys Gly Arg Gly Thr Ser Phe Pro Pro Ser Leu Gly
1105                1110                1115                1120

Val Leu Val Ser Leu Gln Leu Leu Leu Leu Gly Leu Pro Pro Arg
            1125                1130                1135

Pro Gln Pro Gln Ile His Ser Phe Ala Ala Ser Arg Arg Leu
        1140                1145                1150

<210> SEQ ID NO 4
<211> LENGTH: 1085
<212> TYPE: PRT
<213> ORGANISM: Rattus norvegicus

<400> SEQUENCE: 4

Met Ala Gly Pro Gly Ser Leu Cys Cys Ala Ser Arg Gly Ala Ser Ala
1               5                   10                  15

Leu Leu Ala Thr Ala Leu Leu Tyr Ala Ala Leu Gly Asp Val Val Arg
            20                  25                  30

Ser Glu Gln Gln Ile Pro Leu Ser Val Val Lys Leu Trp Ala Ser Ala
        35                  40                  45

Phe Gly Gly Glu Ile Lys Ser Ile Ala Ala Lys Tyr Ser Gly Ser Gln
    50                  55                  60

Leu Leu Gln Lys Lys Tyr Lys Glu Tyr Glu Lys Asp Val Ala Ile Glu
65                  70                  75                  80

Glu Ile Asp Gly Leu Gln Leu Val Lys Lys Leu Ala Lys Asn Met Glu
                85                  90                  95

Glu Met Phe His Lys Lys Ser Glu Ala Val Arg Arg Leu Val Glu Ala
            100                 105                 110

Ala Glu Ala His Leu Lys His Glu Phe Asp Ala Asp Leu Gln Tyr
        115                 120                 125

Glu Tyr Phe Asn Ala Val Leu Ile Asn Glu Arg Asp Lys Asp Gly Asn
    130                 135                 140

Phe Leu Glu Leu Gly Lys Glu Phe Ile Leu Ala Pro Asn Asp His Phe
145                 150                 155                 160

Asn Asn Leu Pro Val Asn Ile Ser Leu Ser Asp Val Gln Val Pro Thr
                165                 170                 175

Asn Met Tyr Asn Lys Asp Pro Ala Ile Val Asn Gly Val Tyr Trp Ser
            180                 185                 190

Glu Ser Leu Asn Lys Val Phe Val Asp Asn Phe Asp Arg Asp Pro Ser
        195                 200                 205

Leu Ile Trp Gln Tyr Phe Gly Ser Ala Lys Gly Phe Phe Arg Gln Tyr
    210                 215                 220

Pro Gly Ile Lys Trp Glu Pro Asp Glu Asn Gly Val Ile Ala Phe Asp
225                 230                 235                 240

Cys Arg Asn Arg Lys Trp Tyr Ile Gln Ala Ala Thr Ser Pro Lys Asp
                245                 250                 255

Val Val Ile Leu Val Asp Val Ser Gly Ser Met Lys Gly Leu Arg Leu
            260                 265                 270

Thr Ile Ala Lys Gln Thr Val Ser Ser Ile Leu Asp Thr Leu Gly Asp
        275                 280                 285

Asp Asp Phe Phe Asn Ile Ile Thr Tyr Asn Glu Glu Leu His Tyr Val
    290                 295                 300

-continued

```
Glu Pro Cys Leu Asn Gly Thr Leu Val Gln Ala Asp Arg Thr Asn Lys
305                 310                 315                 320

Glu His Phe Arg Glu His Leu Asp Lys Leu Phe Ala Lys Gly Ile Gly
                325                 330                 335

Met Leu Asp Ile Ala Leu Asn Glu Ala Phe Asn Val Leu Ser Asp Phe
            340                 345                 350

Asn His Thr Gly Gln Gly Ser Ile Cys Ser Gln Ala Ile Met Leu Ile
        355                 360                 365

Thr Asp Gly Ala Val Asp Thr Tyr Asp Thr Ile Phe Ala Lys Tyr Asn
    370                 375                 380

Trp Pro Glu Arg Lys Val Arg Ile Phe Thr Tyr Leu Ile Gly Arg Glu
385                 390                 395                 400

Ala Ala Phe Ala Asp Asn Leu Lys Trp Met Ala Cys Ala Asn Lys Gly
                405                 410                 415

Phe Phe Thr Gln Ile Ser Thr Leu Ala Asp Val Gln Glu Asn Val Met
            420                 425                 430

Glu Tyr Leu His Val Leu Ser Arg Pro Lys Val Ile Asp Gln Glu His
        435                 440                 445

Asp Val Val Trp Thr Glu Ala Tyr Ile Asp Ser Thr Leu Ala Asp Asp
    450                 455                 460

Gln Gly Leu Val Leu Met Thr Thr Val Ala Met Pro Val Phe Ser Lys
465                 470                 475                 480

Gln Asn Glu Thr Arg Ser Lys Gly Ile Leu Leu Gly Val Val Gly Thr
                485                 490                 495

Asp Val Pro Val Lys Glu Leu Leu Lys Thr Ile Pro Lys Tyr Lys Leu
            500                 505                 510

Gly Ile His Gly Tyr Ala Phe Ala Ile Thr Asn Asn Gly Tyr Ile Leu
        515                 520                 525

Thr His Pro Glu Leu Arg Pro Leu Tyr Glu Glu Gly Lys Lys Arg Arg
    530                 535                 540

Lys Pro Asn Tyr Ser Ser Val Asp Leu Ser Glu Val Glu Trp Glu Asp
545                 550                 555                 560

Arg Asp Asp Val Leu Arg Asn Ala Met Val Asn Arg Lys Thr Gly Lys
                565                 570                 575

Phe Ser Met Glu Val Lys Lys Thr Val Asp Lys Gly Lys Arg Val Leu
            580                 585                 590

Val Met Thr Asn Asp Tyr Tyr Tyr Thr Asp Ile Lys Gly Ala Pro Phe
        595                 600                 605

Ser Leu Gly Val Ala Leu Ser Arg Gly His Gly Lys Tyr Phe Phe Arg
    610                 615                 620

Gly Asn Val Thr Ile Glu Glu Gly Leu His Asp Leu Glu His Pro Asp
625                 630                 635                 640

Val Ser Leu Ala Asp Glu Trp Ser Tyr Cys Asn Thr Asp Leu His Pro
                645                 650                 655

Glu His Arg His Leu Ser Gln Leu Glu Ala Ile Lys Leu Tyr Leu Lys
            660                 665                 670

Gly Lys Glu Pro Leu Leu Gln Cys Asp Lys Glu Leu Ile Gln Glu Val
        675                 680                 685

Leu Phe Asp Ala Val Val Ser Ala Pro Ile Glu Ala Tyr Trp Thr Ser
    690                 695                 700

Leu Ala Leu Asn Lys Ser Glu Asn Ser Asp Lys Gly Val Glu Val Ala
705                 710                 715                 720
```

```
Phe Leu Gly Thr Arg Thr Gly Leu Ser Arg Ile Asn Leu Phe Val Gly
            725                 730                 735

Ala Glu Gln Leu Thr Asn Gln Asp Phe Leu Lys Ala Arg Asp Lys Glu
            740                 745                 750

Asn Ile Phe Asn Ala Asp His Phe Pro Leu Trp Tyr Arg Arg Ala Ala
            755                 760                 765

Glu Gln Ile Pro Gly Ser Phe Val Tyr Ser Ile Pro Phe Ser Thr Gly
            770                 775                 780

Thr Val Asn Lys Ser Asn Val Val Thr Ala Ser Thr Ser Ile Gln Leu
785                 790                 795                 800

Leu Asp Glu Arg Lys Ser Pro Val Val Ala Val Gly Ile Gln Met
            805                 810                 815

Lys Leu Glu Phe Phe Gln Arg Lys Phe Trp Thr Ala Ser Arg Gln Cys
            820                 825                 830

Ala Ser Leu Asp Gly Lys Cys Ser Ile Ser Cys Asp Asp Glu Thr Val
            835                 840                 845

Asn Cys Tyr Leu Ile Asp Asn Asn Gly Phe Ile Leu Val Ser Glu Asp
            850                 855                 860

Tyr Thr Gln Thr Gly Asp Phe Phe Gly Glu Val Glu Gly Ala Val Met
865                 870                 875                 880

Asn Lys Leu Leu Thr Met Gly Ser Phe Lys Arg Ile Thr Leu Tyr Asp
            885                 890                 895

Tyr Gln Ala Met Cys Arg Ala Asn Lys Glu Ser Ser Asp Ser Ala His
            900                 905                 910

Gly Leu Leu Asp Pro Tyr Lys Ala Phe Leu Ser Ala Ala Lys Trp Ile
            915                 920                 925

Val Thr Glu Leu Val Leu Phe Leu Val Glu Phe Asn Leu Cys Ser Trp
            930                 935                 940

Trp His Ser Asp Met Thr Ala Lys Ala Gln Lys Leu Lys Gln Thr Leu
945                 950                 955                 960

Glu Pro Cys Asp Thr Glu Tyr Pro Ala Phe Val Ser Glu Arg Thr Ile
            965                 970                 975

Lys Glu Thr Thr Gly Asn Ile Ala Cys Glu Asp Cys Ser Lys Ser Phe
            980                 985                 990

Val Ile Gln Gln Ile Pro Ser Ser Asn Leu Phe Met Val Val Val Asp
            995                 1000                1005

Ser Ser Cys Leu Cys Glu Ser Val Ala Pro Ile Thr Met Ala Pro Ile
1010                1015                1020

Glu Ile Arg Tyr Asn Glu Ser Leu Lys Cys Glu Arg Leu Lys Ala Gln
1025                1030                1035                1040

Lys Ile Arg Arg Arg Pro Glu Ser Cys His Gly Phe His Pro Glu Glu
                1045                1050                1055

Asn Ala Arg Glu Cys Gly Gly Ala Ser Ser Leu Gln Ala Gln Val Ala
                1060                1065                1070

Leu Leu Leu Leu Pro Leu Val Ser Ser Leu Phe Ser Arg
                1075                1080                1085

<210> SEQ ID NO 5
<211> LENGTH: 3598
<212> TYPE: DNA
<213> ORGANISM: Rattus norvegicus
```

<400> SEQUENCE: 5

| | | | | | |
|---|---|---|---|---|---|
| atggccgggc | cgggctcgct | gtgctgcgcg | tcccgggggg | cctcggcgct | cctagccacc | 60 |
| gcgcttctct | acgccgcgct | gggggacgtg | gtgcgctccg | agcagcagat | cccgctctcc | 120 |
| gtagtgaagc | tctgggcctc | cgcttttggt | ggggagataa | aatccattgc | tgccaagtac | 180 |
| tcgggttccc | agcttctgca | aaagaaatac | aaagagtatg | agaaagacgt | tgccattgaa | 240 |
| gaaatcgacg | gtctccaact | ggtgaaaaag | ctggccaaga | acatggaaga | gatgtttcac | 300 |
| aagaagtccg | aggcagtgcg | gcgtctcgtg | gaggctgcag | aggaagcaca | cctgaagcat | 360 |
| gaatttgacg | ccgacttgca | gtatgaatac | ttcaatgccg | tgctgatcaa | cgagagagac | 420 |
| aaagatggga | acttttttgga | attgggaaag | gagttcatct | tggcccccaa | tgaccatttt | 480 |
| aataatttgc | ctgtgaacat | cagtctgagt | gatgtccaag | tgccaacgaa | catgtacaac | 540 |
| aaagatcctg | ccatagtcaa | tggagtgtat | tggtctgaat | ctctaaacaa | agttttttgta | 600 |
| gacaacttcg | atcgggaccc | gtctctcata | tggcagtact | ttggaagtgc | aaagggcttt | 660 |
| ttcagacagt | acccagggat | taaatgggaa | ccagacgaga | atggagtcat | tgcctttgac | 720 |
| tgcaggaaca | ggaaatggta | catccaggca | gcaacttctc | caaggatgt | ggtcattttg | 780 |
| gtggacgtca | gcgggagcat | gaaaggactc | cgcctgacca | tcgccaagca | aacagtctcc | 840 |
| tcgatactgg | acaccctggg | cgatgatgac | ttcttcaaca | tcatcacgta | taacgaagag | 900 |
| cttcactatg | tggaaccttg | tctgaatgga | acactggttc | aagcggacag | gaccaacaag | 960 |
| gagcacttca | gggagcattt | ggacaaactt | tttgccaaag | ggattggaat | gctcgatatt | 1020 |
| gcgctgaacg | aggccttcaa | tgtactgagc | gatttcaacc | acaccggaca | aggaagcatt | 1080 |
| tgcagccagg | ccattatgct | cataaccgat | ggggcagtgg | acacctacga | caccatcttt | 1140 |
| gcaaagtaca | attggccaga | gcgaaaggtt | cgaatcttca | cttacctcat | tggacgagag | 1200 |
| gctgcttttg | cagacaatct | caagtggatg | gcttgtgcta | acaaaggatt | tttcacccag | 1260 |
| atctccacct | tggctgatgt | gcaggaaaat | gtcatggaat | acctccatgt | actcagtcga | 1320 |
| cccaaagtca | tcgaccagga | acatgatgtg | gtgtggaccg | aagcgtacat | cgacagcact | 1380 |
| ctccctcagg | ctcaaaagct | tgctgatgat | cagggcctcg | tcttgatgac | cacagtggcc | 1440 |
| atgcctgtgt | ttagtaagca | gaacgaaact | aggtcaaagg | gcattcttct | gggtgtggtt | 1500 |
| ggcacagatg | tcccagtaaa | agagcttctg | aagaccatcc | ccaaatacaa | gttaggaatt | 1560 |
| catggttatg | cctttgccat | cacgaataat | ggatacatct | tgacacaccc | ggagctcagg | 1620 |
| cccctgtatg | aagaagggaa | aaagcgaagg | aagcctaatt | acagtagtgt | ggatctctcg | 1680 |
| gaagtcgagt | gggaagatcg | ggatgatgtg | ttacgaaatg | ccatggtgaa | tcggaagact | 1740 |
| gggaaattct | ccatggaagt | gaagaagact | gtggacaaag | ggaaacgggt | tttggtgatg | 1800 |
| accaatgact | actactacac | agacatcaag | ggtgctcctt | tcagtttagg | tgtggcgctc | 1860 |
| tccaggggcc | acgggaaata | cttcttccga | gggaatgtaa | ccattgaaga | agggctccat | 1920 |
| gacttagaac | atcctgacgt | gtccttggca | gatgaatggt | cctactgcaa | cactgatctg | 1980 |
| cacccagagc | accgccatct | ctctcaactg | gaagcgatta | agctctacct | caaaggcaag | 2040 |
| gagcctctgc | ttcaatgtga | caaagaattg | attcaagaag | tccttttttga | tgctgtggta | 2100 |
| agcgcccta | tcgaagccta | ttggaccagc | ctggccctca | acaaatctga | gaattctgac | 2160 |
| aagggtgtag | aggtcgcctt | cctcggcact | cgcacaggcc | tctcaagaat | caacctgttt | 2220 |
| gtgggggctg | aacagctcac | caatcaggac | tttctgaagg | ctagagacaa | agagaacatt | 2280 |
| ttcaacgcag | atcatttccc | tctctggtac | agaagagctg | ccgagcagat | tccaggaagt | 2340 |

-continued

```
tttgtctact ccatcccctt cagcacagga acggtcaaca aaagcaatgt ggtgacagca   2400
agtacctcca tccaactcct ggatgagcga aaatctcctg tggtggcagc tgtaggcatt   2460
cagatgaaac ttgaattctt ccaaaggaag ttctggatgg ccagcagaca gtgtgcctcc   2520
ctggatggta aatgctccat aagctgcgac gatgagactg tgaactgtta cctcatagac   2580
aataacgggt tcattctggt gtctgaagac tacacacaga ctggagattt ttttggtgag   2640
gtcgaaggag ctgtcatgaa caagttgtta acaatgggct cctttaaaag aataaccttg   2700
tatgactacc aagccatgtg tagagccaac aaggagagta gtgacagtgc ccacggactc   2760
ctggacccct ataaggcctt cctctctgca gccaagtgga tagtgacgga acttgtcttg   2820
ttcctggtgg agtttaacct ttgcagttgg tggcactctg acatgacagc taaagcccag   2880
aaactgaaac agaccctgga gccttgtgat actgaatacc cagcctttgt ttccgaacgc   2940
accatcaagg agaccacagg gaacattgct tgtgaagact gctccaagtc ctttgtcatc   3000
cagcaaatcc caagtagcaa tctgttcatg gtggtggtgg acagtagctg tctctgtgag   3060
tctgtggctc ctatcaccat ggcacccatt gaaatcaggt ataatgaatc ccttaagtgt   3120
gaacggttaa aggctcagaa gatcagacga cgtccggaat cctgccacgg cttccatcct   3180
gaggagaatg cgagagagtg tgggggtgca tcaagtctcc aggcccaggt ggccttgctg   3240
ctgctccccc tggtttcgag tctcttctca aggtgacact aactaatggg atgttctttt   3300
ggcatgctat aaatcatgga taaactgtga acccaactat ggtgcgacat agaagacata   3360
agcatagccc agccatcagc atctcatgat tttaaactgt gtgtgataga aactctaaca   3420
ggtacactga ccaaaagttc tcttttttact ttgccaatca tgcaaatgtg agtgccacat   3480
gaccacccctt catcagaaat ggggctgtac tgggtaggca gtggccttct gcttgaaaac   3540
catggaaacc aatttaaaac tgtgtacttt ttaaataaag tatattaaaa tcataaaa     3598
```

<210> SEQ ID NO 6
<211> LENGTH: 1091
<212> TYPE: PRT
<213> ORGANISM: Rattus norvegicus

<400> SEQUENCE: 6

```
Met Ala Gly Pro Gly Ser Leu Cys Cys Ala Ser Arg Gly Ala Ser Ala
1               5                   10                  15

Leu Leu Ala Thr Ala Leu Leu Tyr Ala Ala Leu Gly Asp Val Val Arg
            20                  25                  30

Ser Glu Gln Gln Ile Pro Leu Ser Val Val Lys Leu Trp Ala Ser Ala
        35                  40                  45

Phe Gly Gly Glu Ile Lys Ser Ile Ala Ala Lys Tyr Ser Gly Ser Gln
    50                  55                  60

Leu Leu Gln Lys Lys Tyr Lys Glu Tyr Glu Lys Asp Val Ala Ile Glu
65                  70                  75                  80

Glu Ile Asp Gly Leu Gln Leu Val Lys Lys Leu Ala Lys Asn Met Glu
                85                  90                  95

Glu Met Phe His Lys Lys Ser Glu Ala Val Arg Arg Leu Val Glu Ala
            100                 105                 110

Ala Glu Glu Ala His Leu Lys His Glu Phe Asp Ala Asp Leu Gln Tyr
        115                 120                 125

Glu Tyr Phe Asn Ala Val Leu Ile Asn Glu Arg Asp Lys Asp Gly Asn
    130                 135                 140

Phe Leu Glu Leu Gly Lys Glu Phe Ile Leu Ala Pro Asn Asp His Phe
145                 150                 155                 160
```

```
Asn Asn Leu Pro Val Asn Ile Ser Leu Ser Asp Val Gln Val Pro Thr
                165                 170                 175

Asn Met Tyr Asn Lys Asp Pro Ala Ile Val Asn Gly Val Tyr Trp Ser
            180                 185                 190

Glu Ser Leu Asn Lys Val Phe Val Asp Asn Phe Asp Arg Asp Pro Ser
                195                 200                 205

Leu Ile Trp Gln Tyr Phe Gly Ser Ala Lys Gly Phe Phe Arg Gln Tyr
        210                 215                 220

Pro Gly Ile Lys Trp Glu Pro Asp Glu Asn Gly Val Ile Ala Phe Asp
225                 230                 235                 240

Cys Arg Asn Arg Lys Trp Tyr Ile Gln Ala Ala Thr Ser Pro Lys Asp
                245                 250                 255

Val Val Ile Leu Val Asp Val Ser Gly Ser Met Lys Gly Leu Arg Leu
            260                 265                 270

Thr Ile Ala Lys Gln Thr Val Ser Ser Ile Leu Asp Thr Leu Gly Asp
        275                 280                 285

Asp Asp Phe Phe Asn Ile Ile Thr Tyr Asn Glu Glu Leu His Tyr Val
    290                 295                 300

Glu Pro Cys Leu Asn Gly Thr Leu Val Gln Ala Asp Arg Thr Asn Lys
305                 310                 315                 320

Glu His Phe Arg Glu His Leu Asp Lys Leu Phe Ala Lys Gly Ile Gly
                325                 330                 335

Met Leu Asp Ile Ala Leu Asn Glu Ala Phe Asn Val Leu Ser Asp Phe
            340                 345                 350

Asn His Thr Gly Gln Gly Ser Ile Cys Ser Gln Ala Ile Met Leu Ile
        355                 360                 365

Thr Asp Gly Ala Val Asp Thr Tyr Asp Thr Ile Phe Ala Lys Tyr Asn
    370                 375                 380

Trp Pro Glu Arg Lys Val Arg Ile Phe Thr Tyr Leu Ile Gly Arg Glu
385                 390                 395                 400

Ala Ala Phe Ala Asp Asn Leu Lys Trp Met Ala Cys Ala Asn Lys Gly
                405                 410                 415

Phe Phe Thr Gln Ile Ser Thr Leu Ala Asp Val Gln Glu Asn Val Met
            420                 425                 430

Glu Tyr Leu His Val Leu Ser Arg Pro Lys Val Ile Asp Gln Glu His
        435                 440                 445

Asp Val Val Trp Thr Glu Ala Tyr Ile Asp Ser Thr Leu Pro Gln Ala
    450                 455                 460

Gln Lys Leu Ala Asp Asp Gln Gly Leu Val Leu Met Thr Thr Val Ala
465                 470                 475                 480

Met Pro Val Phe Ser Lys Gln Asn Glu Thr Arg Ser Lys Gly Ile Leu
                485                 490                 495

Leu Gly Val Val Gly Thr Asp Val Pro Val Lys Glu Leu Leu Lys Thr
            500                 505                 510

Ile Pro Lys Tyr Lys Leu Gly Ile His Gly Tyr Ala Phe Ala Ile Thr
        515                 520                 525

Asn Asn Gly Tyr Ile Leu Thr His Pro Glu Leu Arg Pro Leu Tyr Glu
    530                 535                 540

Glu Gly Lys Lys Arg Arg Lys Pro Asn Tyr Ser Ser Val Asp Leu Ser
545                 550                 555                 560

Glu Val Glu Trp Glu Asp Arg Asp Asp Val Leu Arg Asn Ala Met Val
                565                 570                 575
```

-continued

```
Asn Arg Lys Thr Gly Lys Phe Ser Met Glu Val Lys Lys Thr Val Asp
            580                 585                 590
Lys Gly Lys Arg Val Leu Val Met Thr Asn Asp Tyr Tyr Tyr Thr Asp
        595                 600                 605
Ile Lys Gly Ala Pro Phe Ser Leu Gly Val Ala Leu Ser Arg Gly His
610                 615                 620
Gly Lys Tyr Phe Phe Arg Gly Asn Val Thr Ile Glu Glu Gly Leu His
625                 630                 635                 640
Asp Leu Glu His Pro Asp Val Ser Leu Ala Asp Glu Trp Ser Tyr Cys
                645                 650                 655
Asn Thr Asp Leu His Pro Glu His Arg His Leu Ser Gln Leu Glu Ala
            660                 665                 670
Ile Lys Leu Tyr Leu Lys Gly Lys Glu Pro Leu Leu Gln Cys Asp Lys
        675                 680                 685
Glu Leu Ile Gln Glu Val Leu Phe Asp Ala Val Ser Ala Pro Ile
    690                 695                 700
Glu Ala Tyr Trp Thr Ser Leu Ala Leu Asn Lys Ser Glu Asn Ser Asp
705                 710                 715                 720
Lys Gly Val Glu Val Ala Phe Leu Gly Thr Arg Thr Gly Leu Ser Arg
                725                 730                 735
Ile Asn Leu Phe Val Gly Ala Glu Gln Leu Thr Asn Gln Asp Phe Leu
            740                 745                 750
Lys Ala Arg Asp Lys Glu Asn Ile Phe Asn Ala Asp His Phe Pro Leu
        755                 760                 765
Trp Tyr Arg Arg Ala Ala Glu Gln Ile Pro Gly Ser Phe Val Tyr Ser
770                 775                 780
Ile Pro Phe Ser Thr Gly Thr Val Asn Lys Ser Asn Val Val Thr Ala
785                 790                 795                 800
Ser Thr Ser Ile Gln Leu Leu Asp Glu Arg Lys Ser Pro Val Val Ala
                805                 810                 815
Ala Val Gly Ile Gln Met Lys Leu Glu Phe Phe Gln Arg Lys Phe Trp
            820                 825                 830
Met Ala Ser Arg Gln Cys Ala Ser Leu Asp Gly Lys Cys Ser Ile Ser
        835                 840                 845
Cys Asp Asp Glu Thr Val Asn Cys Tyr Leu Ile Asp Asn Asn Gly Phe
850                 855                 860
Ile Leu Val Ser Glu Asp Tyr Thr Gln Thr Gly Asp Phe Phe Gly Glu
865                 870                 875                 880
Val Glu Gly Ala Val Met Asn Lys Leu Leu Thr Met Gly Ser Phe Lys
                885                 890                 895
Arg Ile Thr Leu Tyr Asp Tyr Gln Ala Met Cys Arg Ala Asn Lys Glu
            900                 905                 910
Ser Ser Asp Ser Ala His Gly Leu Leu Asp Pro Tyr Lys Ala Phe Leu
        915                 920                 925
Ser Ala Ala Lys Trp Ile Val Thr Glu Leu Val Leu Phe Leu Val Glu
930                 935                 940
Phe Asn Leu Cys Ser Trp Trp His Ser Asp Met Thr Ala Lys Ala Gln
945                 950                 955                 960
Lys Leu Lys Gln Thr Leu Glu Pro Cys Asp Thr Glu Tyr Pro Ala Phe
                965                 970                 975
Val Ser Glu Arg Thr Ile Lys Glu Thr Thr Gly Asn Ile Ala Cys Glu
            980                 985                 990
```

```
Asp Cys Ser Lys Ser Phe Val Ile Gln Gln Ile Pro Ser Ser Asn Leu
        995                 1000                1005

Phe Met Val Val Asp Ser Ser Cys Leu Cys Glu Ser Val Ala Pro
    1010                1015                1020

Ile Thr Met Ala Pro Ile Glu Ile Arg Tyr Asn Glu Ser Leu Lys Cys
1025                1030                1035                1040

Glu Arg Leu Lys Ala Gln Lys Ile Arg Arg Pro Glu Ser Cys His
            1045                1050                1055

Gly Phe His Pro Glu Glu Asn Ala Arg Glu Cys Gly Gly Ala Ser Ser
            1060                1065                1070

Leu Gln Ala Gln Val Ala Leu Leu Leu Pro Leu Val Ser Ser Leu
    1075                1080                1085

Phe Ser Arg
    1090

<210> SEQ ID NO 7
<211> LENGTH: 8
<212> TYPE: PRT
<213> ORGANISM: Rattus norvegicus

<400> SEQUENCE: 7

Leu Pro Ile Ser Lys Leu Lys Asp
  1               5

<210> SEQ ID NO 8
<211> LENGTH: 3172
<212> TYPE: DNA
<213> ORGANISM: Rattus norvegicus

<400> SEQUENCE: 8
```

| | | | | | |
|---|---|---|---|---|---|
| atggccgggc | cgggctcgct | gtgctgcgcg | tcccgggggg | cctcggcgct | cctagccacc | 60 |
| gcgcttctct | acgccgcgct | gggggacgtg | gtgcgctccg | agcagcagat | ccgctctcc | 120 |
| gtagtgaagc | tctgggcctc | cgcttttggt | ggggagataa | aatccattgc | tgccaagtac | 180 |
| tcgggttccc | agcttctgca | aaagaaatac | aaagagtatg | agaaagacgt | tgccattgaa | 240 |
| gaaatcgacg | gtctccaact | ggtgaaaaag | ctggccaaga | catggaaga | gatgtttcac | 300 |
| aagaagtccg | aggcagtgcg | cgtctcgtg | gaggctgcag | aggaagcaca | cctgaagcat | 360 |
| gaatttgacg | ccgacttgca | gtatgaatac | ttcaatgccg | tgctgatcaa | cgagagagac | 420 |
| aaagatggga | acttttttgga | attgggaaag | gagttcatct | tggcccccaa | tgaccatttt | 480 |
| aataatttgc | ctgtgaacat | cagtctgagt | gatgtccaag | tgccaacgaa | catgtacaac | 540 |
| aaagatcctg | ccatagtcaa | tggagtgtat | tggtctgaat | ctctaaacaa | agttttttgta | 600 |
| gacaacttcg | atcgggaccc | gtctctcata | tggcagtact | ttggaagtgc | aaagggcttt | 660 |
| ttcagacagt | acccagggat | taaatgggaa | ccagacgaga | atggagtcat | tgcctttgac | 720 |
| tgcaggaaca | ggaaatggta | catccaggca | gcaacttctc | caaggatgt | ggtcattttg | 780 |
| gtggacgtca | gcgggagcat | gaaaggactc | cgcctgacca | tcgccaagca | aacagtctcc | 840 |
| tcgatactgg | acaccctggg | cgatgatgac | ttcttcaaca | tcatcactgta | taacgaagag | 900 |
| cttcactatg | tggaaccttg | tctgaatgga | acactggttc | aagcggacag | gaccaacaag | 960 |
| gagcacttca | gggagcattt | ggacaaactt | tttgccaaag | ggattggaat | gctcgatatt | 1020 |
| gcgctgaacg | aggccttcaa | tgtactgagc | gatttcaacc | acaccggaca | aggaagcatt | 1080 |
| tgcagccagg | ccattatgct | cataaccgat | ggggcagtgg | acacctacga | caccatcttt | 1140 |
| gcaaagtaca | attggccaga | gcgaaaggtt | cgaatcttca | cttacctcat | tggacgagag | 1200 |

-continued

```
gctgcttttg cagacaatct caagtggatg gcttgtgcta acaaaggatt tttcacccag    1260
atctccacct tggctgatgt gcaggaaaat gtcatggaat acctccatgt actcagtcga    1320
cccaaagtca tcgaccagga acatgatgtg gtgtggaccg aagcgtacat cgacagcact    1380
ctccctcagg ctcaaaagct tgctgatgat cagggcctcg tcttgatgac cacagtggcc    1440
atgcctgtgt ttagtaagca aacgaaaact aggtcaaagg gcattcttct gggtgtggtt    1500
ggcacagatg tcccagtaaa agagcttctg aagaccatcc ccaaatacaa gttaggaatt    1560
catggttatg cctttgccat cacgaataat ggatacatct tgacacaccc ggagctcagg    1620
cccctgtatg aagaagggaa aaagcgaagg aagcctaatt acagtagtgt ggatctctcg    1680
gaagtcgagt gggaagatcg ggatgatgtg ttacgaaatg ccatggtgaa tcggaagact    1740
gggaaattct ccatggaagt gaagaagact gtggacaaag gaaacgggt tttggtgatg    1800 accaatgact actactacac agacatcaag ggtgctcctt tcagtttagg tgtggcgctc    1860
tccaggggcc acgggaaata cttcttccga gggaatgtaa ccattgaaga agggctccat    1920
gacttagaac atcctgacgt gtccttggca gatgaatggt cctactgcaa cactgatctg    1980
cacccagagc accgccatct ctctcaactg gaagcgatta agctctacct caaaggcaag    2040
gagcctctgc ttcaatgtga caaagaattg attcaagaag tccttttttga tgctgtggta    2100 agcgccccta tcgaagccta ttggaccagc ctggccctca caaatctga gaattctgac    2160 aagggtgtag aggtcgcctt cctcggcact cgcacaggcc tctcaagaat caacctgttt    2220 gtggggctg aacagctcac caatcaggac tttctgaagg ctagagacaa agagaacatt    2280
ttcaacgcag atcatttccc tctctggtac agaagagctg ccgagcagat tccaggaagt    2340
tttgtctact ccatcccctt cagcacagga acggtcaaca aaagcaatgt ggtgacagca    2400
agtacctcca tccaactcct ggatgagcga aaatctcctg tggtggcagc ccagaaactg    2460
aaacagaccc tggagccttg tgatactgaa tacccagcct tgtttccga acgcaccatc    2520 aaggagacca cagggaacat tgcttgtgaa gactgctcca gtcctttgt catccagcaa    2580 atcccaagta gcaatctgtt catggtggtg gtggacagta gctgtctctg tgagtctgtg    2640
gctcctatca ccatggcacc cattgaaatc aggtataatg aatcccttaa gtgtgaacgg    2700
ttaaaggctc agaagatcag acgacgtccg gaatcctgcc acggcttcca tcctgaggag    2760
aatgcgagag agtgtggggg tgcatcaagt ctccaggccc aggtggcctt gctgctgctc    2820
cccctggttt cgagtctctt ctcaaggtga cactaactaa tgggatgttc ttttggcatg    2880
ctataaatca tggataaact gtgaacccaa ctatggtgcg acatagaaga cataagcata    2940
gcccagccat cagcatctca tgattttaaa ctgtgtgtga tagaaactct aacaggtaca    3000
ctgaccaaaa gttctctttt tactttgcca atcatgcaaa tgtgagtgcc acatgaccac    3060
ccttcatcag aaatggggct gtactgggta ggcagtggcc ttctgcttga aaaccatgga    3120
aaccaattta aaactgtgta cttttttaaat aaagtatatt aaaatcataa aa            3172
```

<210> SEQ ID NO 9
<211> LENGTH: 949
<212> TYPE: PRT
<213> ORGANISM: Rattus norvegicus

<400> SEQUENCE: 9

Met Ala Gly Pro Gly Ser Leu Cys Cys Ala Ser Arg Gly Ala Ser Ala
1               5                   10                  15

Leu Leu Ala Thr Ala Leu Leu Tyr Ala Ala Leu Gly Asp Val Val Arg
            20                  25                  30

-continued

```
Ser Glu Gln Gln Ile Pro Leu Ser Val Val Lys Leu Trp Ala Ser Ala
         35                  40                  45

Phe Gly Gly Glu Ile Lys Ser Ile Ala Ala Lys Tyr Ser Gly Ser Gln
 50                  55                  60

Leu Leu Gln Lys Lys Tyr Lys Glu Tyr Glu Lys Asp Val Ala Ile Glu
 65                  70                  75                  80

Glu Ile Asp Gly Leu Gln Leu Val Lys Lys Leu Ala Lys Asn Met Glu
                 85                  90                  95

Glu Met Phe His Lys Lys Ser Glu Ala Val Arg Arg Leu Val Glu Ala
                100                 105                 110

Ala Glu Glu Ala His Leu Lys His Glu Phe Asp Ala Asp Leu Gln Tyr
            115                 120                 125

Glu Tyr Phe Asn Ala Val Leu Ile Asn Glu Arg Asp Lys Asp Gly Asn
130                 135                 140

Phe Leu Glu Leu Gly Lys Glu Phe Ile Leu Ala Pro Asn Asp His Phe
145                 150                 155                 160

Asn Asn Leu Pro Val Asn Ile Ser Leu Ser Asp Val Gln Val Pro Thr
                165                 170                 175

Asn Met Tyr Asn Lys Asp Pro Ala Ile Val Asn Gly Val Tyr Trp Ser
            180                 185                 190

Glu Ser Leu Asn Lys Val Phe Val Asp Asn Phe Asp Arg Asp Pro Ser
        195                 200                 205

Leu Ile Trp Gln Tyr Phe Gly Ser Ala Lys Gly Phe Phe Arg Gln Tyr
        210                 215                 220

Pro Gly Ile Lys Trp Glu Pro Asp Glu Asn Gly Val Ile Ala Phe Asp
225                 230                 235                 240

Cys Arg Asn Arg Lys Trp Tyr Ile Gln Ala Ala Thr Ser Pro Lys Asp
                245                 250                 255

Val Val Ile Leu Val Asp Val Ser Gly Ser Met Lys Gly Leu Arg Leu
                260                 265                 270

Thr Ile Ala Lys Gln Thr Val Ser Ser Ile Leu Asp Thr Leu Gly Asp
            275                 280                 285

Asp Asp Phe Phe Asn Ile Ile Thr Tyr Asn Glu Glu Leu His Tyr Val
        290                 295                 300

Glu Pro Cys Leu Asn Gly Thr Leu Val Gln Ala Asp Arg Thr Asn Lys
305                 310                 315                 320

Glu His Phe Arg Glu His Leu Asp Lys Leu Phe Ala Lys Gly Ile Gly
                325                 330                 335

Met Leu Asp Ile Ala Leu Asn Glu Ala Phe Asn Val Leu Ser Asp Phe
            340                 345                 350

Asn His Thr Gly Gln Gly Ser Ile Cys Ser Gln Ala Ile Met Leu Ile
        355                 360                 365

Thr Asp Gly Ala Val Asp Thr Tyr Asp Thr Ile Phe Ala Lys Tyr Asn
        370                 375                 380

Trp Pro Glu Arg Lys Val Arg Ile Phe Thr Tyr Leu Ile Gly Arg Glu
385                 390                 395                 400

Ala Ala Phe Ala Asp Asn Leu Lys Trp Met Ala Cys Ala Asn Lys Gly
                405                 410                 415

Phe Phe Thr Gln Ile Ser Thr Leu Ala Asp Val Gln Glu Asn Val Met
            420                 425                 430

Glu Tyr Leu His Val Leu Ser Arg Pro Lys Val Ile Asp Gln Glu His
        435                 440                 445
```

-continued

```
Asp Val Val Trp Thr Glu Ala Tyr Ile Asp Ser Thr Leu Pro Gln Ala
450                     455                 460

Gln Lys Leu Ala Asp Asp Gln Gly Leu Val Leu Met Thr Thr Val Ala
465                 470                 475                 480

Met Pro Val Phe Ser Lys Gln Asn Glu Thr Arg Ser Lys Gly Ile Leu
                485                 490                 495

Leu Gly Val Val Gly Thr Asp Val Pro Val Lys Glu Leu Leu Lys Thr
            500                 505                 510

Ile Pro Lys Tyr Lys Leu Gly Ile His Gly Tyr Ala Phe Ala Ile Thr
        515                 520                 525

Asn Asn Gly Tyr Ile Leu Thr His Pro Glu Leu Arg Pro Leu Tyr Glu
    530                 535                 540

Glu Gly Lys Lys Arg Lys Pro Asn Tyr Ser Ser Val Asp Leu Ser
545                 550                 555                 560

Glu Val Glu Trp Glu Asp Arg Asp Val Leu Arg Asn Ala Met Val
                565                 570                 575

Asn Arg Lys Thr Gly Lys Phe Ser Met Glu Val Lys Lys Thr Val Asp
                580                 585                 590

Lys Gly Lys Arg Val Leu Val Met Thr Asn Asp Tyr Tyr Tyr Thr Asp
            595                 600                 605

Ile Lys Gly Ala Pro Phe Ser Leu Gly Val Ala Leu Ser Arg Gly His
        610                 615                 620

Gly Lys Tyr Phe Phe Arg Gly Asn Val Thr Ile Glu Glu Gly Leu His
625                 630                 635                 640

Asp Leu Glu His Pro Asp Val Ser Leu Ala Asp Glu Trp Ser Tyr Cys
                645                 650                 655

Asn Thr Asp Leu His Pro Glu His Arg His Leu Ser Gln Leu Glu Ala
                660                 665                 670

Ile Lys Leu Tyr Leu Lys Gly Lys Glu Pro Leu Leu Gln Cys Asp Lys
        675                 680                 685

Glu Leu Ile Gln Glu Val Leu Phe Asp Ala Val Val Ser Ala Pro Ile
690                 695                 700

Glu Ala Tyr Trp Thr Ser Leu Ala Leu Asn Lys Ser Glu Asn Ser Asp
705                 710                 715                 720

Lys Gly Val Glu Val Ala Phe Leu Gly Thr Arg Thr Gly Leu Ser Arg
                725                 730                 735

Ile Asn Leu Phe Val Gly Ala Glu Gln Leu Thr Asn Gln Asp Phe Leu
                740                 745                 750

Lys Ala Arg Asp Lys Glu Asn Ile Phe Asn Ala Asp His Phe Pro Leu
            755                 760                 765

Trp Tyr Arg Arg Ala Ala Glu Gln Ile Pro Gly Ser Phe Val Tyr Ser
        770                 775                 780

Ile Pro Phe Ser Thr Gly Thr Val Asn Lys Ser Asn Val Val Thr Ala
785                 790                 795                 800

Ser Thr Ser Ile Gln Leu Leu Asp Glu Arg Lys Ser Pro Val Val Ala
                805                 810                 815

Ala Gln Lys Leu Lys Gln Thr Leu Glu Pro Cys Asp Thr Glu Tyr Pro
                820                 825                 830

Ala Phe Val Ser Glu Arg Thr Ile Lys Glu Thr Thr Gly Asn Ile Ala
            835                 840                 845

Cys Glu Asp Cys Ser Lys Ser Phe Val Ile Gln Gln Ile Pro Ser Ser
850                 855                 860
```

```
Asn Leu Phe Met Val Val Asp Ser Ser Cys Leu Cys Glu Ser Val
865                 870                 875                 880

Ala Pro Ile Thr Met Ala Pro Ile Glu Ile Arg Tyr Asn Glu Ser Leu
            885                 890                 895

Lys Cys Glu Arg Leu Lys Ala Gln Lys Ile Arg Arg Pro Glu Ser
                900                 905                 910

Cys His Gly Phe His Pro Glu Glu Asn Ala Arg Glu Cys Gly Gly Ala
            915                 920                 925

Ser Ser Leu Gln Ala Gln Val Ala Leu Leu Leu Pro Leu Val Ser
    930                 935                 940

Ser Leu Phe Ser Arg
945

<210> SEQ ID NO 10
<211> LENGTH: 3474
<212> TYPE: DNA
<213> ORGANISM: Rattus norvegicus

<400> SEQUENCE: 10
```

| | | | | |
|---|---|---|---|---|
| atggcggtgc | cggctcggac | ctgcggcgct | tcttggcccg | gcccggtgcg gaccgctcgc | 60 |
| ccctggcccg | gtcgcggtcc | ccggccctgc | cctgaccccc | ggggcccagc gtccgggccc | 120 |
| gcacgcccgc | tcttgctact | gctgccgcct | ctgctgcttt | taccgctgct caccgccccc | 180 |
| ggcgcctctg | cctacagctt | cccccagcag | cacacgatgc | agcactgggc ccggcgcctg | 240 |
| gagcaggaga | ttgacggtgt | gatgcggatt | tttggaggcg | tgcagcagct ccgagagatc | 300 |
| tacaaggaca | tcggaacct | gtttgatgtg | caggagaatg | aaccacagaa actagtggag | 360 |
| aaggtggcag | ggacattga | gagcctgctg | gacagaaagg | tccaggcctt gaagagactg | 420 |
| gctgacgctg | cagagaattt | ccagaaagcc | caccgctggc | aagacaacat caaggaggaa | 480 |
| gacatcatgt | actatgacgc | caaggctgac | gccgagctgg | atgatcctga gagtgaggat | 540 |
| atggagaggg | gatccaagac | cagcgcctta | aggctggact | tcatcgagga gccaaacttc | 600 |
| aagaacaaag | tcaactattc | atacacggcg | gtgcagatcc | ccacagatat ctacaaaggc | 660 |
| tctaccgtca | tcctcaatga | gcttaactgg | acggaggccc | tggagaatgt cttcattgag | 720 |
| aaccgtaggc | aagaccctac | actgttgtgg | caagtcttcg | gcagtgccac gggagtcacc | 780 |
| cgctattacc | cagccacacc | gtggcgagcc | cccaagaaga | ttgacctgta cgatgtcaga | 840 |
| agacgaccct | ggtatataca | gggggcctca | tcacccaagg | acatggtcat cattgtggat | 900 |
| gtgagtggca | gtgtgagcgg | cctgacgctg | aagctgatga | gacgtctgt ctgtgagatg | 960 |
| ctagacacac | tctccgatga | tgactatgtg | aatgtggcct | cattcaacga gaaggcgcag | 1020 |
| cctgtgtctt | gcttcacaca | cctggtgcag | gccaatgtgc | ggaacaagaa ggtgttcaag | 1080 |
| gaagctgtgc | agggcatggt | ggccaagggc | accacaggct | acaaggctgg cttgagtat | 1140 |
| gcctttgacc | agctacagaa | ttccaacatc | acccgtgcta | actgcaataa gatgatcatg | 1200 |
| atgttcacgg | acggggaga | ggatcgcgtg | caggacgtct | ttgaaaagta taattggccc | 1260 |
| aatcggacgg | tacgcgtctt | cacgttctcc | gtaggacagc | ataactatga tgtcacaccc | 1320 |
| ctgcagtgga | tggcttgtac | taacaaaggt | tactattttg | agatcccttc catcggagcc | 1380 |
| atccgcatca | acacacagga | atacctggat | gtgctgggta | ggcccatggt cctggcaggc | 1440 |
| aaggacgcca | agcaagtgca | atggacaaac | gtgtatgaag | atgcgctggg gctgggggttg | 1500 |
| gtggtaacag | ggactctccc | tgttttcaac | ctgacacagg | atggccctgg ggaaaagaag | 1560 |
| aaccagctaa | tcctgggtgt | catgggcata | gatgtggccc | tgaatgacat caaaaggctg | 1620 |

-continued

```
actcccaact acacacttgg cgccaatggc tacgtgttcg ccatcgacct gaatggctat    1680
gtgttgctac atcccaatct caagccccag actaccaact tccgggagcc tgtgaccttg    1740
gacttcctgg atgcagagct ggaagatgag aacaaggagg agatccgtcg tagtatgatt    1800
gacgaagaca aaggccacaa gcagatcaga accttggtca atccctgga tgagaggtac     1860 atagatgaag tgattcggaa ctacacctgg gtgcctataa ggagtaccaa ctacagcctg    1920
gggctggtgc tcccacccta cagcacctac tacctccaag ccaacctcag cgaccagatc    1980
ctgcaggtca agttgccaat cagcaaactg aaggattttg agttcctgct ccccagcagc    2040
tttgagtctg aaggacatgt tttcattgct cccagagagt attgcaagga tttgaatgcc    2100
tcagacaaca acaccgagtt cctgaaaaac ttcattgagc tcatggagaa agtgactccg    2160
gactccaagc agtgcaataa cttccttctg cataacttga ttttggacac gggcattacg    2220
cagcagttag tggaacgcgt ctggcgggac caagatctca acacgtacag cctgctagct    2280
gtatttgctg ccactgacgg tgcagtcaca cgtgtcttcc gaacaaggc agctgaagac     2340 tggacagaaa accctgaacc cttcaatgcc agcttctacc gccgcagcct ggataaccgt    2400
ggttatatct tcaagccccc gcaccaggac tccctgttaa ggccactgga gctggagaat    2460
gacacagtag gcgtcctcgt cagcacagct gtagagctca gtctgggtcg ccgcacactg    2520
aggccagcag tggtgggtgt caaactggac ctagaggctt gggctgaaaa gttcaaggtg    2580
cttgccagca accgtaccca tcaggaccaa cctcagaagc agtgcggccc cagcagccac    2640
tgtgagatgg actgcgaggt aaacaacgag gacctactct gtgtcctcat tgatgacggg    2700
ggattcctgg tgctgtcaaa ccagaaccac cagtgggacc aggttggcag attcttcagt    2760
gaggtggatg ccaacctgat gctggcactg tacaataact ccttctacac cagaaaggag    2820
tcctatgact atcaggcagc ttgtgcccct cagcctcctg gcaacctggg tgctgcaccc    2880
aggggtgtct ttgtgcccac cattgcagat ttccttaact tggcctggtg gacctctgct    2940
gccgcctggt ccttattcca gcaactactt tatggtctca tctatcacag ctggttccag    3000
gcagacccgg cagaagccga gggcagcccc gagacgcgcg agagcagctg cgtcatgaaa    3060
caaacccagt actacttcgg ctcggtgaac gcgtcctata cgccatcat cgactgcgga    3120 aactgcagca ggctgttcca cgcgcagaga ctgaccaaca ccaaccttct gttcgtggtg    3180
gcggagaagc cgctgtgcag ccagtgcgag gtcggccggc tgctacaaaa ggagacacac    3240
tgcccagcgg acggcccgga gcagtgtgag ctggtgcaga gaccgcgata ccgaagaggc    3300
ccgcacatct gttttgacta caatgcgacg gaagatacct cagactgtgg ccgcggcacg    3360
tccttccctc cgtcgctggg cgtcttggtt tccctgcagc tgttgctcct cctaggcctg    3420
ccacctcggc cgcagcctca aatccattcc ttcgctgcct ctcgccgcct ctga          3474
```

<210> SEQ ID NO 11
<211> LENGTH: 1157
<212> TYPE: PRT
<213> ORGANISM: Rattus norvegicus

<400> SEQUENCE: 11

```
Met Ala Val Pro Ala Arg Thr Cys Gly Ala Ser Trp Pro Gly Pro Val
 1               5                  10                  15

Arg Thr Ala Arg Pro Trp Pro Gly Arg Gly Pro Arg Pro Cys Pro Asp
            20                  25                  30

Pro Arg Gly Pro Ala Ser Gly Pro Ala Arg Pro Leu Leu Leu Leu Leu
        35                  40                  45
```

```
Pro Pro Leu Leu Leu Pro Leu Leu Thr Ala Pro Gly Ala Ser Ala
 50                  55                  60

Tyr Ser Phe Pro Gln Gln His Thr Met Gln His Trp Ala Arg Arg Leu
 65                  70                  75                  80

Glu Gln Glu Ile Asp Gly Val Met Arg Ile Phe Gly Gly Val Gln Gln
                 85                  90                  95

Leu Arg Glu Ile Tyr Lys Asp Asn Arg Asn Leu Phe Asp Val Gln Glu
                100                 105                 110

Asn Glu Pro Gln Lys Leu Val Glu Lys Val Ala Gly Asp Ile Glu Ser
                115                 120                 125

Leu Leu Asp Arg Lys Val Gln Ala Leu Lys Arg Leu Ala Asp Ala Ala
130                 135                 140

Glu Asn Phe Gln Lys Ala His Arg Trp Gln Asp Asn Ile Lys Glu Glu
145                 150                 155                 160

Asp Ile Met Tyr Tyr Asp Ala Lys Ala Asp Ala Glu Leu Asp Asp Pro
                165                 170                 175

Glu Ser Glu Asp Met Glu Arg Gly Ser Lys Thr Ser Ala Leu Arg Leu
                180                 185                 190

Asp Phe Ile Glu Glu Pro Asn Phe Lys Asn Lys Val Asn Tyr Ser Tyr
                195                 200                 205

Thr Ala Val Gln Ile Pro Thr Asp Ile Tyr Lys Gly Ser Thr Val Ile
                210                 215                 220

Leu Asn Glu Leu Asn Trp Thr Glu Ala Leu Glu Asn Val Phe Ile Glu
225                 230                 235                 240

Asn Arg Arg Gln Asp Pro Thr Leu Leu Trp Gln Val Phe Gly Ser Ala
                245                 250                 255

Thr Gly Val Thr Arg Tyr Tyr Pro Ala Thr Pro Trp Arg Ala Pro Lys
                260                 265                 270

Lys Ile Asp Leu Tyr Asp Val Arg Arg Pro Trp Tyr Ile Gln Gly
                275                 280                 285

Ala Ser Ser Pro Lys Asp Met Val Ile Val Asp Val Ser Gly Ser
                290                 295                 300

Val Ser Gly Leu Thr Leu Lys Leu Met Lys Thr Ser Val Cys Glu Met
305                 310                 315                 320

Leu Asp Thr Leu Ser Asp Asp Tyr Val Asn Val Ala Ser Phe Asn
                325                 330                 335

Glu Lys Ala Gln Pro Val Ser Cys Phe Thr His Leu Val Gln Ala Asn
                340                 345                 350

Val Arg Asn Lys Lys Val Phe Lys Glu Ala Val Gln Gly Met Val Ala
                355                 360                 365

Lys Gly Thr Thr Gly Tyr Lys Ala Gly Phe Glu Tyr Ala Phe Asp Gln
                370                 375                 380

Leu Gln Asn Ser Asn Ile Thr Arg Ala Asn Cys Asn Lys Met Ile Met
385                 390                 395                 400

Met Phe Thr Asp Gly Gly Glu Asp Arg Val Gln Asp Val Phe Glu Lys
                405                 410                 415

Tyr Asn Trp Pro Asn Arg Thr Val Arg Val Phe Thr Phe Ser Val Gly
                420                 425                 430

Gln His Asn Tyr Asp Val Thr Pro Leu Gln Trp Met Ala Cys Thr Asn
                435                 440                 445

Lys Gly Tyr Tyr Phe Glu Ile Pro Ser Ile Gly Ala Ile Arg Ile Asn
450                 455                 460
```

-continued

```
Thr Gln Glu Tyr Leu Asp Val Leu Gly Arg Pro Met Val Leu Ala Gly
465                 470                 475                 480

Lys Asp Ala Lys Gln Val Gln Trp Thr Asn Val Tyr Glu Asp Ala Leu
            485                 490                 495

Gly Leu Gly Leu Val Val Thr Gly Thr Leu Pro Val Phe Asn Leu Thr
            500                 505                 510

Gln Asp Gly Pro Gly Glu Lys Lys Asn Gln Leu Ile Leu Gly Val Met
            515                 520                 525

Gly Ile Asp Val Ala Leu Asn Asp Ile Lys Arg Leu Thr Pro Asn Tyr
            530                 535                 540

Thr Leu Gly Ala Asn Gly Tyr Val Phe Ala Ile Asp Leu Asn Gly Tyr
545                 550                 555                 560

Val Leu Leu His Pro Asn Leu Lys Pro Gln Thr Thr Asn Phe Arg Glu
                565                 570                 575

Pro Val Thr Leu Asp Phe Leu Asp Ala Glu Leu Glu Asp Glu Asn Lys
                580                 585                 590

Glu Glu Ile Arg Arg Ser Met Ile Asp Glu Asp Lys Gly His Lys Gln
                595                 600                 605

Ile Arg Thr Leu Val Lys Ser Leu Asp Glu Arg Tyr Ile Asp Glu Val
610                 615                 620

Ile Arg Asn Tyr Thr Trp Val Pro Ile Arg Ser Thr Asn Tyr Ser Leu
625                 630                 635                 640

Gly Leu Val Leu Pro Pro Tyr Ser Thr Tyr Tyr Leu Gln Ala Asn Leu
                645                 650                 655

Ser Asp Gln Ile Leu Gln Val Lys Leu Pro Ile Ser Lys Leu Lys Asp
                660                 665                 670

Phe Glu Phe Leu Leu Pro Ser Ser Phe Glu Ser Glu Gly His Val Phe
                675                 680                 685

Ile Ala Pro Arg Glu Tyr Cys Lys Asp Leu Asn Ala Ser Asp Asn Asn
                690                 695                 700

Thr Glu Phe Leu Lys Asn Phe Ile Glu Leu Met Glu Lys Val Thr Pro
705                 710                 715                 720

Asp Ser Lys Gln Cys Asn Asn Phe Leu Leu His Asn Leu Ile Leu Asp
                725                 730                 735

Thr Gly Ile Thr Gln Gln Leu Val Glu Arg Val Trp Arg Asp Gln Asp
                740                 745                 750

Leu Asn Thr Tyr Ser Leu Leu Ala Val Phe Ala Ala Thr Asp Gly Ala
                755                 760                 765

Val Thr Arg Val Phe Pro Asn Lys Ala Ala Glu Asp Trp Thr Glu Asn
770                 775                 780

Pro Glu Pro Phe Asn Ala Ser Phe Tyr Arg Arg Ser Leu Asp Asn Arg
785                 790                 795                 800

Gly Tyr Ile Phe Lys Pro Pro His Gln Asp Ser Leu Leu Arg Pro Leu
                805                 810                 815

Glu Leu Glu Asn Asp Thr Val Gly Val Leu Val Ser Thr Ala Val Glu
                820                 825                 830

Leu Ser Leu Gly Arg Arg Thr Leu Arg Pro Ala Val Val Gly Val Lys
                835                 840                 845

Leu Asp Leu Glu Ala Trp Ala Glu Lys Phe Lys Val Leu Ala Ser Asn
                850                 855                 860

Arg Thr His Gln Asp Gln Pro Gln Lys Gln Cys Gly Pro Ser Ser His
865                 870                 875                 880
```

Cys Glu Met Asp Cys Glu Val Asn Asn Glu Asp Leu Leu Cys Val Leu
                885                 890                 895

Ile Asp Asp Gly Gly Phe Leu Val Leu Ser Asn Gln Asn His Gln Trp
            900                 905                 910

Asp Gln Val Gly Arg Phe Phe Ser Glu Val Asp Ala Asn Leu Met Leu
        915                 920                 925

Ala Leu Tyr Asn Asn Ser Phe Tyr Thr Arg Lys Glu Ser Tyr Asp Tyr
    930                 935                 940

Gln Ala Ala Cys Ala Pro Gln Pro Pro Gly Asn Leu Gly Ala Ala Pro
945                 950                 955                 960

Arg Gly Val Phe Val Pro Thr Ile Ala Asp Phe Leu Asn Leu Ala Trp
                965                 970                 975

Trp Thr Ser Ala Ala Trp Ser Leu Phe Gln Gln Leu Leu Tyr Gly
            980                 985                 990

Leu Ile Tyr His Ser Trp Phe Gln Ala Asp Pro Ala Glu Ala Glu Gly
        995                 1000                1005

Ser Pro Glu Thr Arg Glu Ser Ser Cys Val Met Lys Gln Thr Gln Tyr
    1010                1015                1020

Tyr Phe Gly Ser Val Asn Ala Ser Tyr Asn Ala Ile Ile Asp Cys Gly
1025                1030                1035                1040

Asn Cys Ser Arg Leu Phe His Ala Gln Arg Leu Thr Asn Thr Asn Leu
                1045                1050                1055

Leu Phe Val Val Ala Glu Lys Pro Leu Cys Ser Gln Cys Glu Val Gly
            1060                1065                1070

Arg Leu Leu Gln Lys Glu Thr His Cys Pro Ala Asp Gly Pro Glu Gln
        1075                1080                1085

Cys Glu Leu Val Gln Arg Pro Arg Tyr Arg Arg Gly Pro His Ile Cys
    1090                1095                1100

Phe Asp Tyr Asn Ala Thr Glu Asp Thr Ser Asp Cys Gly Arg Gly Thr
1105                1110                1115                1120

Ser Phe Pro Pro Ser Leu Gly Val Leu Val Ser Leu Gln Leu Leu Leu
                1125                1130                1135

Leu Leu Gly Leu Pro Pro Arg Pro Gln Pro Gln Ile His Ser Phe Ala
            1140                1145                1150

Ala Ser Arg Arg Leu
        1155

<210> SEQ ID NO 12
<211> LENGTH: 22
<212> TYPE: DNA
<213> ORGANISM: Rattus norvegicus

<400> SEQUENCE: 12
agccatccgc atcaacacac ag                                          22

<210> SEQ ID NO 13
<211> LENGTH: 23
<212> TYPE: DNA
<213> ORGANISM: Rattus norvegicus

<400> SEQUENCE: 13
agcaacacgt agccgttcag gtc                                         23

<210> SEQ ID NO 14
<211> LENGTH: 24
<212> TYPE: DNA
<213> ORGANISM: Rattus norvegicus

```
<400> SEQUENCE: 14
gctcctcgat gaagtccagc ctta                                              24

<210> SEQ ID NO 15
<211> LENGTH: 24
<212> TYPE: DNA
<213> ORGANISM: Rattus norvegicus

<400> SEQUENCE: 15
cggcgccgca tcttgaatgg aaac                                              24

<210> SEQ ID NO 16
<211> LENGTH: 24
<212> TYPE: DNA
<213> ORGANISM: Rattus norvegicus

<400> SEQUENCE: 16
gcgaagcttg aaacatggcg gtgc                                              24

<210> SEQ ID NO 17
<211> LENGTH: 26
<212> TYPE: DNA
<213> ORGANISM: Rattus norvegicus

<400> SEQUENCE: 17
tggatcccct ctccatatcc tcactc                                            26

<210> SEQ ID NO 18
<211> LENGTH: 27
<212> TYPE: DNA
<213> ORGANISM: Rattus norvegicus

<400> SEQUENCE: 18
gtgtccttgg cagatgaatg gtcctac                                           27

<210> SEQ ID NO 19
<211> LENGTH: 26
<212> TYPE: DNA
<213> ORGANISM: Rattus norvegicus

<400> SEQUENCE: 19
gatgtacttg ctgtcaccac attgct                                            26

<210> SEQ ID NO 20
<211> LENGTH: 24
<212> TYPE: DNA
<213> ORGANISM: Rattus norvegicus

<400> SEQUENCE: 20
atcgcttcca gttgagagag atgg                                              24

<210> SEQ ID NO 21
<211> LENGTH: 25
<212> TYPE: DNA
<213> ORGANISM: Rattus norvegicus

<400> SEQUENCE: 21
atggccgggc cgggctcgct gtgct                                             25

<210> SEQ ID NO 22
<211> LENGTH: 6
<212> TYPE: PRT
<213> ORGANISM: Rattus norvegicus
```

```
-continued

<400> SEQUENCE: 22

Leu Pro Gln Ala Gln Lys
 1               5
```